United States Patent [19]

Engvall et al.

[11] Patent Number: 5,837,496
[45] Date of Patent: Nov. 17, 1998

[54] MEROSIN FRAGMENTS AND USES THEREOF

[75] Inventors: Eva Engvall, Escondido, Calif.; Ilmo Leivo, Helsinki, Finland

[73] Assignee: La Jolla Cancer Research Foundation, La Jolla, Calif.

[21] Appl. No.: 460,309

[22] Filed: Jun. 2, 1995

Related U.S. Application Data

[60] Division of Ser. No. 125,077, Sep. 22, 1993, which is a continuation-in-part of Ser. No. 919,951, Jul. 27, 1992, abandoned, which is a continuation of Ser. No. 472,319, Jan. 30, 1990, abandoned.

[51] Int. Cl.$^6$ .............................. C12P 21/06; C07K 1/00
[52] U.S. Cl. ........................................... 435/69.3; 530/350
[58] Field of Search ............................ 530/350; 435/69.3

[56] References Cited

U.S. PATENT DOCUMENTS 5,444,158  8/1995  Engvall et al. ........................ 530/395

FOREIGN PATENT DOCUMENTS 204 302    3/1986  European Pat. Off. ........ C12N 15/00
91/11462   8/1991  WIPO ............................ C07K 13/00

OTHER PUBLICATIONS

Cornbrooks et al., "In vivo and in vitro observations on laminin production by Schwann cells," *Proc. Natl. Acad. Sci. USA* 80:3850–3854 (1983).

Davis et al., "Isolation and characterization of rat Schwannoma neurite–promoting factor: evidence that the factor contains laminin," *J. Neurosci.* 5:2662–2671 (1985).

Deutzmann et al., "Structural study of long arm fragments of laminin: evidence for repetitive C–terminal sequences in the A–chain, not present in the B–chains," *Eur. J. Biochem.* 177:35–45 (1988).

Edgar et al., "Structural requirements for the stimulation of neurite outgrowth by two variants of laminin and their inhibition by antibodies," *J. Cell. Biol.* 106:1299–1306 (1988).

Engvall et al., "Distribution and isolation of four laminin variants: tissues restricted distribution of heterotrimers assembled from five different subunits," *Cell. Regul.* 1(10):731–740 (1990).

Engvall et al., "Merosin is a tissue–restricted basement membrane component and a member of a family of laminin like protein," *J. Cell. Biol.* 109:4 part 2 (1989), (New York US), Twenty–Ninth Annual Meeting of the American Society for Cell Biology, Houston, TX, 5–9, Nov. 1989, Minisymposium 1, Abstract 3.

Engvall et al., "Merosin promotes cell attachment and neurite outgrowth and is a component of the neurite–promoting factor of RN22 Schwannoma cells," *E. Cell. Res.* 198:115–123 (1992).

Hagg et al., "Merosin is associated with neurons of the adult mammalian central nervous system," *J. Cell. Biol.* 111, 5 part 2 (1990), Abstract 2227.

Hassell et al., "Isolation of two forms of basement membrane proteoglycans," *J. Biol. Chem.* 260:8098–8105 (1984).

Hunter et al., "A laminin–like adhesive protein concentrated in the synaptic cleft of the neuromuscular junction," *Nature* 338:229–233 (1989).

Lander et al., "Laminin is associated with the neurite outgrowth–promoting factors found in conditioned media," *Proc. Natl. Acad. Sci. USA* 82:2183–2187 (1985).

Leivo et al., "Distribution of merosin, a laminin–related, tissue–specific basement membrane protein, in human schwann cell neoplasms," *Laboratory Invest.* 61:426–432 (1989).

Leivo et al., "Merosin, a protein specific for basement membranes of Schwann cells, striated muscle, and trophoblast, is expressed late in nerve and muscle development," *Proc. Natl. Acad. Sci. USA* 85:1544–1548 (1988).

Manthorpe et al., "A dissection of tissue culture," *Manual of the Nervous System*, pp. 322–326 (1989).

Martin and Timpl, "Laminin and other basement membrane components," *Ann. Rev. Cell. Biol.* 3:57–85 (1987).

Ohno et al., "Isolation of laminin from human placental basement membranes: amnion, chorion and chorionic microvessels", *Biochem. Biophys. Res. Commun.* 112(3):1091–1098 (1983).

Paulsson and Saladin, "Mouse heart laminin," *J. Biol. Chem.* 264:18726–18732 (1989).

Sandrock and Matthew, "Identification of a peripheral nerve neurite growth–promoting activity by development and use of an in vitro bioassay," *Proc. Natl. Acad. Sci. USA* 84:6934–6938 (1987).

Steele and Hoffman, "Neurite–promoting activity from fetal skeletal muscle: partial purification of a high–molecular–weight form," *J. Neurosci. Res.* 15:323–339 (1986).

Terranova et al., "Laminin promotes rabbit neutrophil motility and attachment," *J. Clin. Invest.* 77:1180–1186 (1986).

Palm and Furcht, "Production of Laminin and Fibronectin by Schwannoma Cells: Cell–Protein Interactions In Vitro and Protein Localization in Peripheral Nerve In Vivo" *J. Cell Biol.* 96:1218–1226 (1983).

Hayashi and Miki, "Purification and Characterization of a Neurite Outgrowth Factor from Chicken Gizzard Smooth Muscle" *J. Biol. Chem.* 260:14269–14278 (1985).

(List continued on next page.)

*Primary Examiner*—Susan A. Loring
*Attorney, Agent, or Firm*—Campbell & Flores LLP

[57] ABSTRACT

This invention provides an isolated nucleic acid molecule encoding a subunit of a protein, the protein having an apparent molecular weight of about 800 kD, designated merosin. Also provided are isolated nucleic acid molecules which encode merosin fragments. Anti-merosin antibodies, vectors for the recombinant production of merosin, and the expression of recombinant proteins by use of a host vector system also are provided. The invention further provides the use of merosin to promote neurite growth and for certain diagnostic applications.

3 Claims, 30 Drawing Sheets

OTHER PUBLICATIONS

Wewer et al., "Human Laminin Isolated in a Nearly Intact, Biologically Active Form from Placenta by Limited Proteolysis" *J. Biol. Chem.* 258:12654–12660 (1983).

Paulsson et al., "Structure of Laminin Variants—The 300–kDa chains of murine and bovine heart laminin are related to the human placenta merosin heavy chain and replace the A chain in some laminin variants" *J. Biol. Chem.* 266:17545–17551 (1991).

Ohno et al., "Laminin M is found in placental basement membranes, but not in basement membranes of neoplastic origin" *Conn. Tissue Res.* 15:199–207 (1986).

Maniates et al., *Molecular Cloning a Laboratory Manual*, Chapter 6, pp. 98–106 and 224–246. (1982).

Ehrig et al. Proc. Natl. Acad Sci 87:3264–3268, 1990.

Ehrig et al. Annals of the New York Academy of Sciences 580:276–280 (Paper present 1989).

```
AAA AAA GCC GAC ATC CTG GAT GTC GTG GGA ATG CTG TAT GTT GGG TTA CCC ATC AAC TAC ACT CGA AGA ATT GGT CCA ACC TAT AGC        2784
 K   K   A   D   I   L   D   V   V   G   M   L   Y   V   G   L   P   I   N   Y   T   R   R   I   G   P   V   T   Y   S      925

ATT GAT GGC GTC ACA GGA ACA ATG GCA GAG GCC CCT GCC GAT CTG GAA CAA CCC ACC TCC AGC TTC CAT GTT GGG ACA GTG TTT GCA AAT    2880
 I   D   G   V   T   G   T   M   A   E   A   P   A   D   L   E   Q   P   T   S   S   F   H   V   G   T   V   F   A   N      957

GCT CAG AGG ACA ACT GGA GTT CTT GGG ATC AGT GAT CTG GAT CTT GAC GTT GGT GCA ATG GAT GGA ATT GAA GAG TTT GAA TTC CGC        2976
 A   Q   R   T   T   G   V   L   G   I   S   D   L   D   L   D   V   G   A   M   D   G   I   E   E   F   E   F   R          989

ACA ACT ACA ACT GGA GTT CTT GGG ATC AGT GAT GCT GGG GTT CCA GGG CAT TTG AAT GGT GAT GAA AAG TTG ATG TTT CAT GTG            3072
 T   T   T   T   G   V   L   G   I   S   D   A   G   V   P   G   H   L   N   G   D   E   K   L   M   F   H   V             1021

GAC AAT GGT GCG AGA GAC CTC ACA GTC TAT GAT GGG AAC CAG GTG GAA ATG CAA TGG CAT AAA GTC ACT GCC AAC AAG ATC                3168
 D   N   G   A   R   D   L   T   V   Y   D   G   N   Q   V   E   M   Q   W   H   K   V   T   A   N   K   I                 1053

AAA CAC CGC ATT GAG CTC ACA CGA TTC GAT GTC GAT CAG TTT GGC CTA ACA TCA GCT GAC TCT GAC ACA AAT GAC CCT GTG                3264
 K   H   R   I   E   L   T   R   F   D   V   D   Q   F   G   L   T   S   A   D   S   D   T   N   D   P   V                 1085

GTT GGA GGC TTC CCA GAT GAC CTC AAG GAT TTG CCA AGG GGG ATC AGA TCC CGA GGT TGC ATC AGA TCC CTG AAG CTC ACC AAA GGC ACA    3360
 V   G   G   F   P   D   D   L   K   D   L   P   R   G   I   R   S   R   G   C   I   R   S   L   K   L   T   K   G   T     1117

GCA AGC CAC TGG AGG TTG CCA AGG CCC TGG AAC TGA GGG GCG TTC AAC CTG TAT CAT GCC CAG CCA ACT AAT AAA ATT AAG TGT AAC CCC    3456
 A   S   H   W   R   L   P   R   P   W   N    *

AGG AAG AGT CTG TCA AAA CAA GTA TAT CAA GTA TAT CAA CAA ACA AAT ATA TTT TAC CTA TAT ATG TTA ATT AAA CTA ATT TGT GCA TGT ACA TAG AAT    3552

TC                                                                                                                         3554
```

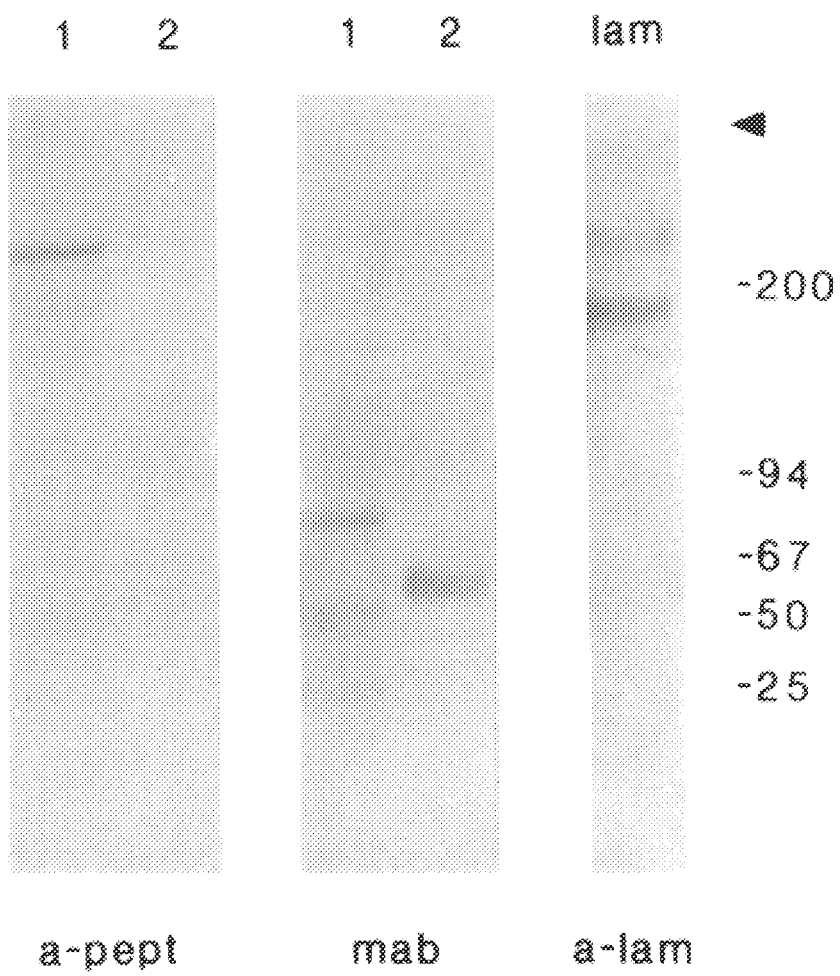

```
   1                                            CAGCGACTCCTCTGGCTCCCGAGAAGTGGATCCGGTCGCGGCCACTACG
  50  ATGCCGGGAGCCGCCGGGGTCCTCCTCCTTCTGCTGCTCTCCGGAGGCCTCGGGGGCGTACAGGCGCAGCGGCCG
   1   M  P  G  A  A  G  V  L  L  L  L  L  L  S  G  G  L  G  G  V  Q  A  Q  R  P
                                                                         △
      CAGCAGCAGCGGCAGTCACAGGCACATCAGCAAAGAGGTTTATTCCCTGCTGTCCTGAATCTTGCTTCTAATGCT
       Q  Q  Q  R  Q  S  Q  A  H  Q  Q  R  G  L  F  P  A  V  L  N  L  A  S  N  A
 200  CTTATCACGACCAATGCAACATGTGGAGAAAAAGGACCTGAAATGTACTGCAAATTGGTAGAACATGTCCCTGGG
  51   L  I  T  T |N  A  T|©  G  E  K  G  P  E  M  Y ©  K  L  V  E  H  V  P  G
      CAGCCTGTGAGGAACCCGCAGTGTCGAATCTGCAATCAAAACAGCAGCAATCCAAACCAGAGACACCCGATTACA
       Q  P  V  R  N  P  Q ©  R  I ©  N  Q |N  S  S| N  P  N  Q  R  H  P  I  T
 350  AATGCTATTGATGGAAAGAACACTTGGTGGCAGAGTCCCAGTATTAAGAATGGAATCGAATACCATTATGTGACA
 101   N  A  I  D  G  K  N  T  W  W  Q  S  P  S  I  K  N  G  I  E  Y  H  Y  V  T
      ATTACACTGGATTTACAGCAGGTGTTCCAGATCGCGTATGTGATTGTGAAGGCAGCTAACTCCCCCCGGCCTGGA
       I  T  L  D  L  Q  Q  V  F  Q  I  A  Y  V  I  V  K  A  A  N  S  P  R  P  G
 500  AACTGGATTTTGGAACGCTCTCTTGATGATGTTGAATACAAGCCCTGGCAGTATCATGCTGTGACAGACACGGAG
 151   N  W  I  L  E  R  S  L  D  D  V  E  Y  K  P  W  Q  Y  H  A  V  T  D  T  E
      TGCCTAACGCTTTACAATATTTATCCCCGCACTGGGCCACCGTCATATGCCAAAGATGATGAGGTCATCTGCACT
      ©  L  T  L  Y  N  I  Y  P  R  T  G  P  P  S  Y  A  K  D  D  E  V  I ©  T
 650  TCATTTTACTCCAAGATACACCCCTTAGAAAATGGAGAGATTCACATCTCTTTAATCAATGGGAGACCAAGTGCC
 201   S  F  Y  S  K  I  H  P  L  E  N  G  E  I  H  I  S  L  I  N  G  R  P  S  A
      GATGATCCTTCTCCAGAACTGCTAGAATTTACCTCCGCTCGCTATATTCGCCTGAGATTTCAGAGGATCCGCACA
       D  D  P  S  P  E  L  L  E  F  T  S  A  R  Y  I  R  L  R  F  Q  R  I  R  T
 800  CTGAATGCTGACTTGATGATGTTTGCTCACAAAGACCCAAGAGAAATTGACCCCATTGTCACCAGAAGATATTAC
 251   L  N  A  D  L  M  M  F  A  H  K  D  P  R  E  I  D  P  I  V  T  R  R  Y  Y
      TACTCGGTCAAGGATATTTCAGTTGGAGGGATGTGCATCTGCTATGGTCATGCCAGGGCTTGTCCACTTGATCCA
       Y  S  V  K  D  I  S  V  G  G  M ©  I ©  Y  G  H  A  R  A ©  P  L  D  P
 950  GCGACAAATAAATCTCGCTGTGAGTGTGAGCATAACACATGTGGCGATAGCTGTGATCAGTGCTGTCCAGGATTC
 301   A  T |N  K  S| R ©  E ©  E  H  N  T ©  G  D  S ©  D  Q © ©  P  G  F
      CATCAGAAACCCTGGAGAGCTGGAACTTTTCTAACTAAAACTGAATGTGAAGCATGCAATTGTCATGGAAAAGCT
       H  Q  K  P  W  R  A  G  T  F  L  T  K  T  E ©  E  A ©  N ©  H  G  K  A
1100  GAAGAATGCTATTATGATGAAAATGTTGCCAGAAGAAATCTGAGTTTGAATATACGTGGAAAGTACATTGGAGGG
 351   E  E ©  Y  Y  D  E  N  V  A  R  R |N  L  S| L  N  I  R  G  K  Y  I  G  G
      GGTGTCTGCATTAATTGTACCCAAAACACTGCTGGTATAAACTGCGAGACATGTACAGATGGCTTCTTCAGACCC
       G  V ©  I |N ©  T| Q  N  T  A  G  I  N ©  E  T ©  T  D  G  F  F  R  P
1250  AAAGGGGTATCTCCAAATTATCCAAGGCCATGCCAGCCATGTCATTGCGATCCAATTGGTTCCTTAAATGAAGTC
 401   K  G  V  S  P  N  Y  P  R  P ©  Q  P ©  H ©  D  P  I  G  S  L  N  E  V
      TGTGTCAAGGATGAGAAACATGCTCGACGAGGTTTGGCACCTGGATCCTGTCATTGCAAAACTGGTTTTGGAGGT
      ©  V  K  D  E  K  H  A  R  R  G  L  A  P  G  S ©  H ©  K  T  G  F  G  G
1400  GTGAGCTGTGATCGGTGTGCCAGGGGCTACACTGGCTACCCGGACTGCAAAGCCTGTAACTGCAGTGGGTTAGGG
 451   V  S ©  D  R ©  A  R  G  Y  T  G  Y  P  D ©  K  A ©|N ©  S| G  L  G
      AGCAAAAATGAGGATCCTTGTTTTGGCCCCTGTATCTGCAAGGAAAATGTTGAAGGAGGAGACTGTAGTCGTTGC
       S  K  N  E  D  P ©  F  G  P ©  I ©  K  E  N  V  E  G  G  D ©  S  R ©
1550  AAATCCGGCTTCTTCAATTTGCAAGAGGATAATTGGAAAGGCTGCGATGAGTGTTTCTGTTCAGGGGTTTCAAAC
 501   K  S  G  F  F  N  L  Q  E  D  N  W  K  G ©  D  E ©  F ©  S  G  V  S  N
      AGATGTCAGAGTTCCTACTGGACCTATGGCAAAATACAAGATATGAGTGGCTGGTATCTGACTGACCTTCCTGGC
       R ©  Q  S  S  Y  W  T  Y  G  K  I  Q  D  M  S  G  W  Y  L  T  D  L  P  G
1700  CGCATTCGAGTGGCTCCCCAGCAGGACGACTTGGACTCACCTCAGCAGATCAGCATCAGTAACGCGGAGGCCCGG
 551   R  I  R  V  A  P  Q  Q  D  D  L  D  S  P  Q  Q  I  S  I  S  N  A  E  A  R
      CAAGCCCTGCCGCACAGCTACTACTGGAGCGCGCCGGCTCCCTATCTGGGAAACAAACTCCCAGCAGTAGGAGGA
       Q  A  L  P  H  S  Y  Y  W  S  A  P  A  P  Y  L  G  N  K  L  P  A  V  G  G
```

FIG. 6A

```
1850  CAGTTGACATTTACCATATCATATGACCTTGAAGAAGAGGAAGAAGATACAGAACGTGTTCTCCAGCTTATGATT
 601   Q  L  T  F  T  I  S  Y  D  L  E  E  E  E  E  D  T  E  R  V  L  Q  L  M  I
      ATCTTAGAGGGTAATGACTTGAGCATCAGCACAGCCCAAGATGAGGTGTACCTGCACCCATCTGAAGAACATACT
       I  L  E  G  N  D  L  S  I  S  T  A  Q  D  E  V  Y  L  H  P  S  E  E  H  T
2000  AATGTATTGTTACTTAAAGAAGAATCATTTACCATACATGGCACACATTTTCCAGTCCGTAGAAAGGAATTTATG
 651   N  V  L  L  L  K  E  E  S  F  T  I  H  G  T  H  F  P  V  R  R  K  E  F  M
      ACAGTGCTTGCGAATTTGAAGAGAGTCCTCCTACAAATCACATACAGCTTTGGGATGGATGCCATCTTCAGGTTG
       T  V  L  A  N  L  K  R  V  L  L  Q  I  T  Y  S  F  G  M  D  A  I  F  R  L
2150  AGCTCTGTTAACCTTGAATCCGCTGTCTCCTATCCTACTGATGGAAGCATTGCAGCAGCTGTAGAAGTGTGTCAG
 701   S  S  V  N  L  E  S  A  V  S  Y  P  T  D  G  S  I  A  A  A  V  E  V  Ⓒ  Q
      TGCCCACCAGGGTATACTGGCTCCTCTTGTGAATCTTGTTGGCCTAGGCACAGGCGAGTTAACGGCACTATTTTT
       Ⓒ  P  P  G  Y  T  G  S  S  Ⓒ  E  S  Ⓒ  W  P  R  H  R  R  V │N  G  T│ I  F
2300  GGTGGCATCTGTGAGCCATGTCAGTGCTTTGGTCATGCGGAGTCCTGTGATGACGTCACTGGAGAATGCCTGAAC
 751   G  G  I  Ⓒ  E  P  Ⓒ  Q  Ⓒ  F  G  H  A  E  S  Ⓒ  D  D  V  T  G  E  Ⓒ  L  N
      TGTAAGGATCACACAGGTGGCCCATATTGTGATAAATGTCTTCCTGGTTTCTATGGCGAGCCTACTAAAGGAACC
       Ⓒ  K  D  H  T  G  G  P  Y  Ⓒ  D  K  Ⓒ  L  P  G  F  Y  G  E  P  T  K  G  T
2450  TCTGAAGACTGTCAACCCTGTGCCTGTCCACTCAATATCCCATCCAATAACTTTAGCCCAACGTGCCATTTAGAC
 801   S  E  D  Ⓒ  Q  P  Ⓒ  A  Ⓒ  P  L  N  I  P  S  N  N  F  S  P  T  Ⓒ  H  L  D
      CGGAGTCTTGGATTGATCTGTGATGGATGCCCTGTCGGGTACACAGGACCACGCTGTGAGAGGTGTGCAGAAGGC
       R  S  L  G  L  I  Ⓒ  D  G  Ⓒ  P  V  G  Y  T  G  P  R  Ⓒ  E  R  Ⓒ  A  E  G
2600  TATTTTGGACAACCCTCTGTACCTGGAGGATCATGTCAGCCATGCCAATGCAATGACAACCTTGACTTCTCCATC
 851   Y  F  G  Q  P  S  V  P  G  G  S  Ⓒ  Q  P  Ⓒ  Q  Ⓒ  N  D  N  L  D  F  S  I
      CCTGGCAGCTGTGACAGCTTGTCTGGCTCCTGTCTGATATGTAAACCAGGTACAACAGGCCGGTACTGTGAGCTC
       P  G  S  Ⓒ  D  S  L  S  G  S  Ⓒ  L  I  Ⓒ  K  P  G  T  T  G  R  Y  Ⓒ  E  L
2750  TGTGCTGATGGATATTTTGGAGATGCAGTTGATGCGAAGAACTGTCAGCCCTGTCGCTGTAATGCCGGTGGCTCT
 901   Ⓒ  A  D  G  Y  F  G  D  A  V  D  A  K  N  Ⓒ  Q  P  Ⓒ  R  Ⓒ  N  A  G  G  S
      TTCTCTGAGGTTTGCCACAGTCAAACTGGACAGTGTGAGTGCAGAGCCAACGTTCAGGGTCAGAGATGTGACAAA
       F  S  E  V  Ⓒ  H  S  Q  T  G  Q  Ⓒ  E  Ⓒ  R  A  N  V  Q  G  Q  R  Ⓒ  D  K
2900  TGCAAGGCTGGGACCTTTGGCCTACAATCAGCAAGGGGCTGTGTTCCCTGCAACTGCAATTCTTTTGGGTCTAAG
 951   Ⓒ  K  A  G  T  F  G  L  Q  S  A  R  G  Ⓒ  V  P  Ⓒ  N  Ⓒ  N  S  F  G  S  K
      TCATTCGACTGTGAAGAGAGTGGACAATGTTGGTGCCAACCTGGAGTCACAGGGAAGAAATGTGACCGCTGTGCC
       S  F  D  Ⓒ  E  E  S  G  Q  Ⓒ  W  Ⓒ  Q  P  G  V  T  G  K  K  Ⓒ  D  R  Ⓒ  A
3050  CACGGCTATTTCAACTTCCAAGAAGGAGGCTGCACAGCTTGTGAATGTTCTCATCTGGGTAATAATTGTGACCCA
1001   H  G  Y  F  N  F  Q  E  G  G  Ⓒ  T  A  Ⓒ  E  Ⓒ  S  H  L  G  N  N  Ⓒ  D  P
      AAGACTGGGCGATGCATTTGCCCACCCAATACCATTGGAGAGAAATGTTCTAAATGTGCACCCAATACCTGGGGC
       K  T  G  R  Ⓒ  I  Ⓒ  P  P  N  T  I  G  E  K  Ⓒ  S  K  Ⓒ  A  P  N  T  W  G
3200  CACAGCATTACCACTGGTTGTAAGGCTTGTAACTGCAGCACAGTGGGATCCTTGGATTTCCAATGCAATGTAAAT
1051   H  S  I  T  T  G  Ⓒ  K  A  Ⓒ │N  Ⓒ  S│ T  V  G  S  L  D  F  Q  Ⓒ  N  V  N
      ACAGGCAATGCAACTGTCATCCAAAATTCTCTGGTGCAAAATGTACAGAGTGCAGTCGAGGTCACTGGAACTAC
       T  G  Q  Ⓒ  N  Ⓒ  H  P  K  F  S  G  A  K  Ⓒ  T  E  Ⓒ  S  R  G  H  W  N  Y
3350  CCTCGCTGCAATCTCTGTGACTGCTTCCTCCCTGGGACAGATGCCACAACCTGTGATTCAGAGACTAAAAAATGC
1101   P  R  Ⓒ  N  L  Ⓒ  D  Ⓒ  F  L  P  G  T  D  A  T  T  Ⓒ  D  S  E  T  K  K  Ⓒ
      TCCTGTAGTGATCAAACTGGGCAGTGCACTTGTAAGGTGAATGTGGAAGGCATCCACTGTGACAGATGCCGGCCT
       S  Ⓒ  S  D  Q  T  G  Q  Ⓒ  T  Ⓒ  K  V  N  V  E  G  I  H  Ⓒ  D  R  Ⓒ  R  P
3500  GGCAAATTCGGACTCGATGCCAAGAATCCACTTGGCTGCAGCAGCTGCTATTGCTTCGGCACTACTACCCAGTGC
1151   G  K  F  G  L  D  A  K  N  P  L  G  Ⓒ  S  S  Ⓒ  Y  Ⓒ  F  G  T  T  T  Q  Ⓒ
      TCTGAAGCAAAAGGACTGATCCGGACGTGGGTGACTCTGAAGGCTGAGCAGACCATTCTACCCCTGGTAGATGAG
       S  E  A  K  G  L  I  R  T  W  V  T  L  K  A  E  Q  T  I  L  P  L  V  D  E
```

FIG. 6B

```
3650  GCTCTGCAGCACACGACCACCAAGGGCATTGTTTTTCAACATCCAGAGATTGTTGCCCACATGGACCTGATGAGA
1201   A  L  Q  H  T  T  T  K  G  I  V  F  Q  H  P  E  I  V  A  H  M  D  L  M  R
      GAAGATCTCCATTTGGAACCTTTTTATTGGAAACTTCCAGAACAATTTGAAGGAAAGAAGTTGATGGCCTATGGG
       E  D  L  H  L  E  P  F  Y  W  K  L  P  E  Q  F  E  G  K  K  L  M  A  Y  G
3800  GGCAAACTCAAGTATGCAATCTATTTCGAGGCTCGGGAAGAAACAGGTTTCTCTACATATAATCCTCAAGTGATC
1251   G  K  L  K  Y  A  I  Y  F  E  A  R  E  E  T  G  F  S  T  Y  N  P  Q  V  I
      ATTCGAGGTGGGACACCTACTCATGCTAGAATTATCGTCAGGCATATGGCTGCTCCTCTGATTGGCCAATTGACA
       I  R  G  G  T  P  T  H  A  R  I  I  V  R  H  M  A  A  P  L  I  G  Q  L  T
3950  AGGCATGAAATTGAAATGACAGAGAAAGAATGGAAATATTATGGGGATGATCCTCGAGTCCATAGAACTGTGACC
1301   R  H  E  I  E  M  T  E  K  E  W  K  Y  Y  G  D  D  P  R  V  H  R  T  V  T
      CGAGAAGACTTCTTGGATATACTATATGATATTCATTACATTCTTATCAAAGCTACTTATGGAAATTTCATGCGA
       R  E  D  F  L  D  I  L  Y  D  I  H  Y  I  L  I  K  A  T  Y  G  N  F  M  R
4100  CAAAGCAGGATTTCTGAAATCTCAATGGAGGTAGCTGAACAAGGACGTGGAACAACAATGACTCCTCCAGCTGAC
1351   Q  S  R  I  S  E  I  S  M  E  V  A  E  Q  G  R  G  T  T  M  T  P  P  A  D
      TTGATTGAAAAATGTGATTGTCCCCTGGGCTATTCTGGCCTGTCCTGTGAGGCATGCTTGCCGGGATTTTATCGA
       L  I  E  K Ⓒ D Ⓒ P  L  G  Y  S  G  L  S Ⓒ E  A Ⓒ L  P  G  F  Y  R
4250  CTGCGTTCTCAACCAGGTGGCCGCACCCCTGGACCAACCCTGGGCACCTGTGTTCCATGTCAATGTAATGGACAC
1401   L  R  S  Q  P  G  G  R  T  P  G  P  L  G  T Ⓒ V  P Ⓒ Q Ⓒ N  G  H
      AGCAGCCTGTGTGACCCTGAAACATCGATATGCCAGAATTGTCAACATCACACTGCTGGTGACTTCTGTGAACGA
       S  S  L Ⓒ D  P  E  T  S  I Ⓒ Q  N Ⓒ Q  H  H  T  A  G  D  F Ⓒ E  R
4400  TGTGCTCTTGGATACTATGGAATTGTCAAGGGATTGCCAAATGACTGTCAGCAATGTGCCTGCCCTCTGATTTCT
1451  Ⓒ A  L  G  Y  Y  G  I  V  K  G  L  P  N  D Ⓒ Q  Q Ⓒ A Ⓒ P  L  I  S
      TCCAGTAACAATTTCAGCCCCTCTTGTGTCGCAGAAGGACTTGACGACTACCGCTGCACGGCTTGTCCACGGGGA
       S  S  N  N  F  S  P  S Ⓒ V  A  E  G  L  D  D  Y  R Ⓒ T  A Ⓒ P  R  G
4550  TATGAAGGCCAGTACTGTGAAAGGTGTGCCCCTGGCTATACTGGCAGTCCAGGCAACCCTGGAGGCTCCTGCCAA
1501   Y  E  G  Q  Y Ⓒ E  R Ⓒ A  P  G  Y  T  G  S  P  G  N  P  G  G  S Ⓒ Q
      GAATGTGAGTGTGATCCCTATGGCTCACTGCCTGTGCCCTGTGACCCTGTCACAGGATTCTGCACGTGCCGACCT
       E Ⓒ E Ⓒ D  P  Y  G  S  L  P  V  P Ⓒ D  P  V  T  G  F Ⓒ T Ⓒ R  P
4700  GGAGCCACGGGAAGGAAGTGTGACGGCTGCAAGCACTGGCATGCACGCGAGGGCTGGGAGTGTGTTTTTTGTGGA
1551   G  A  T  G  R  K Ⓒ D  G Ⓒ K  H  W  H  A  R  E  G  W  E Ⓒ V  F Ⓒ G
      GATGAGTGCACTGGCCTTCTTCTCGGTGACTTGGCTCGCCTGGAGCAGATGGTCATGAGCATCAACCTCACTGGT
       D  E Ⓒ T  G  L  L  L  G  D  L  A  R  L  E  Q  M  V  M  S  I │N  L  T│G
4850  CCGCTGCCCTGCGCCATATAAAATGCTGTATGGTCTTGAAAATATGACTCAGGAGCTAAAGCACTTGCTGTCACCT
1601   P  L  P  A  P  Y  K  M  L  Y  G  L  E │N  M  T│Q  E  L  K  H  L  L  S  P
      CAGCGGGCCCCAGAGAGGCTTATTCAGCTGGCAGAGGGCAATCTGAATACACTCGTGACCGAAATGAACGAGCTG
       Q  R  A  P  E  R  L  I  Q  L  A  E  G  N  L  N  T  L  V  T  E  M  N  E  L
5000  CTGACCAGGGCTACCAAAGTGACAGCAGATGGCGAGCAGACCGGACAGGATGCTGAGAGGACCAACACAAGAGCA
1651   L  T  R  A  T  K  V  T  A  D  G  E  Q  T  G  Q  D  A  E  R  T  N  T  R  A
      AAGTCCCTGGGAGAATTCATTAAGGAGCTTGCCCGGGATGCAGAAGCTGTAAATGAAAAAGCTATAAAACTAAAT
       K  S  L  G  E  F  I  K  E  L  A  R  D  A  E  A  V  N  E  K  A  I  K  L │N
5150  GAAACTCTAGGAACTCGAGACGAGGCCTTTGAGAGAAATTTGGAAGGGCTTCAGAAAGAGATTGACCAGATGATT
1701   E  T│L  G  T  R  D  E  A  F  E  R  N  L  E  G  L  Q  K  E  I  D  Q  M  I
      AAAGAACTGAGGAGGAAAAATCTAGAGACACAAAAGGAAATTGCTGAAGATGAGTTGGTAGCTGCAGAAGCCCTT
       K  E  L  R  R  K  N  L  E  T  Q  K  E  I  A  E  D  E  L  V  A  A  E  A  L
5300  CTGAAAAAAGTGAAGAAGCTGTTTGGAGAGTCCCGGGGGGAAAATGAAGAAATGGAGAAGGATCTCCGGGAAAAA
1751   L  K  K  V  K  K  L  F  G  E  S  R  G  E  N  E  E  M  E  K  D  L  R  E  K
      CTGGCTGACTACAAAAACAAAGTTGATGATGCTTGGGACCTTTTGAGAGAAGCCACAGATAAAATCAGAGAAGCT
       L  A  D  Y  K  N  K  V  D  D  A  W  D  L  L  R  E  A  T  D  K  I  R  E  A
5450  AATCGCCTATTTGCAGTAAATCAGAAAAACATGACTGCATTGGAGAAAAAGAAGGAGGCTGTTGAGAGCGGCAAA
1801   N  R  L  F  A  V  N  Q  K │N  M  T│A  L  E  K  K  K  E  A  V  E  S  G  K
      CGACAAATTGAGAACACTTTAAAAGAAGGCAATGACATACTCGATGAAGCCAACCGTCTTGCAGATGAAATCAAC
       R  Q  I  E  N  T  L  K  E  G  N  D  I  L  D  E  A  N  R  L  A  D  E  I  N
```

FIG. 6C

```
5600  TCCATCATAGACTATGTTGAAGACATCCAAACTAAATTGCCACCTATGTCTGAGGAGCTTAATGATAAAATAGAT
1851   S  I  I  D  Y  V  E  D  I  Q  T  K  L  P  P  M  S  E  E  L  N  D  K  I  D
      GACCTCTCCCAAGAAATAAAGGACAGGAAGCTTGCTGAGAAGGTGTCCCAGGCTGAGAGCCACGCAGCTCAGTTG
       D  L  S  Q  E  I  K  D  R  K  L  A  E  K  V  S  Q  A  E  S  H  A  A  Q  L
5750  AATGACTCATCTGCTGTCCTTGATGGAATCCTTGATGAGGCTAAAAACATCTCCTTCAATGCCACTGCAGCCTTC
1901   N  D  S  S  A  V  L  D  G  I  L  D  E  A  K  N  I  S  F  N  A  T  A  A  F
      AAAGCTTACAGCAATATTAAGGACTATATTGATGAAGCTGAGAAAGTTGCCAAAGAAGCCAAAGATCTTGCACAT
       K  A  Y  S  N  I  K  D  Y  I  D  E  A  E  K  V  A  K  E  A  K  D  L  A  H
5900  GAAGCTACAAAACTGGCAACAGGTCCTCGGGGTTTATTAAAGGAAGATGCCAAAGGCTGTCTTCAGAAAAGCTTC
1951   E  A  T  K  L  A  T  G  P  R  G  L  L  K  E  D  A  K  G  C  L  Q  K  S  F
      AGGATTCTTAACGAAGCCAAGAAGTTAGCAAATGATGTAAAAGAAAATGAAGACCATCTAAATGGCTTAAAAACC
       R  I  L  N  E  A  K  K  L  A  N  D  V  K  E  N  E  D  H  L  N  G  L  K  T
6050  AGGATAGAAAATGCTGATGCTAGAAATGGGGATCTCTTGAGAACTTTGAATGACACTTTGGGAAAGTTATCAGCT
2001   R  I  E  N  A  D  A  R  N  G  D  L  L  R  T  L  N  D  T  L  G  K  L  S  A
      ATTCCAAATGATACAGCTGCTAAACTGCAAGCTGTTAAGGACAAAGCCAGACAAGCCAACGACACAGCTAAAGAT
       I  P  N  D  T  A  A  K  L  Q  A  V  K  D  K  A  R  Q  N  D  T  A  K  D
6200  GTACTGGCACAGATTACAGAGCTCCACCAGAACCTCGATGGCCTGAAGAAGAATTACAATAAACTAGCAGACAGC
2051   V  L  A  Q  I  T  E  L  H  Q  N  L  D  G  L  K  K  N  Y  N  K  L  A  D  S
      GTCGCCAAAACGAATGCTGTGGTTAAAGATCCTTCCAAGAACAAAATCATTGCCGATGCAGATGCCACTGTCAAA
       V  A  K  T  N  A  V  V  K  D  P  S  K  N  K  I  I  A  D  A  D  A  T  V  K
6350  AATTTAGAACAGGAAGCTGACCGGCTAATAGATAAACTCAAACCCATCAAGGAACTTGAGGATAACCTAAAGAAA
2101   N  L  E  Q  E  A  D  R  L  I  D  K  L  K  P  I  K  E  L  E  D  N  L  K  K
      AACATCTCTGAGATAAAGGAATTGATAAACCAAGCTCGGAAACAAGCCAATTCTATCAAAGTATCTGTGTCTTCA
       N  I  S  E  I  K  E  L  I  N  Q  A  R  K  Q  A  N  S  I  K  V  S  V  S  S
6500  GGAGGTGACTGCATTCGAACATACAAACCAGAAATCAAGAAAGGAAGTTACAATAATATTGTTGTCAACGTAAAG
2151   G  G  D  C  I  R  T  Y  K  P  E  I  K  K  G  S  Y  N  N  I  V  V  N  V  K
      ACAGCTGTTGCTGATAACCTCCTCTTTTATCTTGGAAGTGCCAAATTTATTGACTTTCTGGCTATAGAAATGCGT
       T  A  V  A  D  N  L  L  F  Y  L  G  S  A  K  F  I  D  F  L  A  I  E  M  R
6650  AAAGGCAAAGTCAGCTTCCTCTGGGATGTTGGATCTGGAGTTGGACGTGTAGAGTACCCAGATTTGACTATTGAT
2201   K  G  K  V  S  F  L  W  D  V  G  S  G  V  G  R  V  E  Y  P  D  L  T  I  D
      GACTCATATTGGTACCGTATCGTAGCATCAAGAACTGGGAGAAATGGAACTATTTCTGTGAGAGCCCTGGATGGA
       D  S  Y  W  Y  R  I  V  A  S  R  T  G  R  N  G  T  I  S  V  R  A  L  D  G
6800  CCCAAAGCCAGCATTGTGCCCAGCACACACCATTCGACGTCTCCTCCAGGGTACACGATTCTAGATGTGGATGCA
2251   P  K  A  S  I  V  P  S  T  H  H  S  T  P  P  G  Y  T  I  L  D  V  D  A
      AATGCAATGCTGTTTGTTGGTGGCCTGACTGGGAAATTAAAGAAGGCTGATGCTGTACGTGTGATTAC
       N  A  M  L  F  V  G  G  L  T  G  K  L  K  K  A  D  A  V  R  V  I  T  F  T

E G N D L S I S T A Q D E     V Y L H P S E E H T N V L L L K
     | |   |   : : | |   |   |       :     |   |   | |       | | :   | IVb
     K G N G L T L S T     Q A E G L S L Q P Y E E Y L N V V R L V

W C Q P G V T G K K C D R C A H G Y F N F Q E G G C T A C E
      |         | | | : : | | |   | | | | |   | | : :   : | |   | |
    H C V P G V A G K R C D R C A H G F Y A Y Q D G S C T P C D   IIIb

E D L H L E P F Y W K L P E Q F E G K K L M A Y G G K L K Y
      : :     | | | | | : | |   | | |   | | | | | | | | | | |   IVa
      Q H I R A E P F Y W R L P Q Q F Q G D Q L M A Y G G K L K Y

1256  A I Y F E A R E E T G F S T Y N P Q V I I R G G T P T H A
      : :   |   :   :   | |   : | | | : | : | |             :
1240  S V A F Y S L D G V G T S N F E P Q V L I K G G       R I

R I I V R H M A A P L I G Q L T R H E I E     M T E K E W K Y
      |   |   | |   :     | |   |   |     | |           | | |
      R K Q V I Y M D A P A P E N G V R Q E Q E V A M R E N F W K Y
                                                                IVa
1314  Y G D D P R V H R T V T R E D F L D I L Y D I H Y I L I K
              :           | | | | | | :   : |   | |   | | | |
1297          F N S V S E K P V T R E D F M S V L S D I E Y I L I K

1432  E T S I C Q N C Q H H T A G D F C E R C A L G Y Y G I V K
            |   | |   | |   | | | | | |   : | |   : | | | | |
1415  N T G K C L N C G D N T A G D H C D V C T S G Y Y G K V T
                                                                    IIIa
      G L P N D C Q Q C A C P L I S S S N N F S P S C V A E G L D D
      |       | |   | | | | | |       |           : | |   | |     |
      G S A S D C A L C A C P   H S P P A S F S P T C V L E G D H D

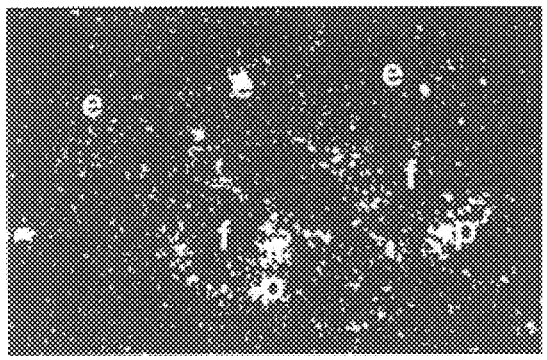
FIG. IOE
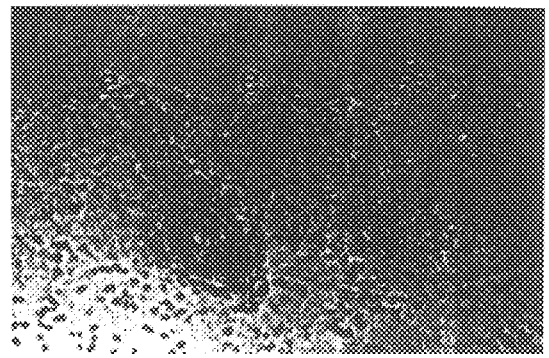
FIG. IOF
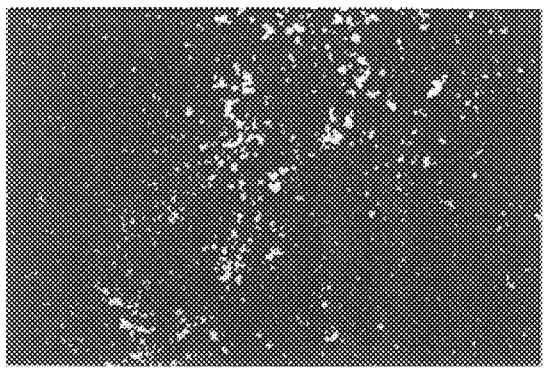
FIG. IOG
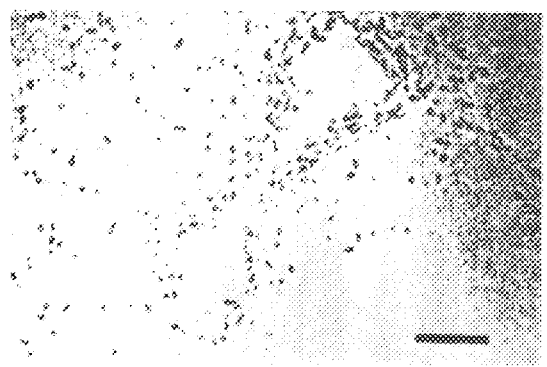
FIG. IOH

```
B1  QEPEFSY GCAEGSCYPATGDLLIGRAQKLSVTSTCGL  HKPEPYCIVS                      HLQEDKKCFICNSQDPYHETLNPDSHLIENVTTFAPNRLKI
S   QVPSLDVPGCSRGSCYPATGDLLVGRADRLTASSTCGL  HSPQPYCIVS                      HLQDEKKCFLCDSRRPFSARDNPNSHRIQNVVTSFAPQRRTA
A                RQRGLFPAILNLASNAHISTNA     TCGE KGPEMPCKLV  EHVPGRPVRNPQCRICDGNSANPRERHPI                SHAIDGTNN
mA               QQRGLFPAILNLATNAHISANA     TCGE KGPEMPCKLV  EHVPGRPVRHAQCRVCDGNSTNPRERHPI                SHAIDGTNN
M   QRPQQQRQSQAHQQRGLFPAVLNLASNALITTNA      TCGE KGPEMYCKLV  EHVPGQPVRNPQCRICNQNSSNPNQRHPI                TNAIDGKNT
dA                 ELTPPYFNLATGRKIYATA      TCGPDTDGPELYCKLVGANTEHDHIDYSVIQGQVCDYCD   PTVPERNHPP        ENAIDGTEA
B2  QAAMDECTDEGGRPQRCMPEFVNAAFNVTVATN        TCG  TPPEEYCVQ                  TGVTGVTKSCHLCDAGQPHLQHGAAF LTDYNNQADTT

B1  WWQS   ENGVEN VTIQLDLEAEFHFTHLIMTF KTFRPAAMLIERSSDFGKTWGVYRYFA    YDCEASFPGISTGPMKKV           DDI ICDSRYSDIEP
S   WWQS   ENGVPM VTIQLDLEAEFHFTHLIMTF KTFRPAAMLVERSADFGRTWRVYRYFS    YDCGADPPGIPLAPPRRW           DDV VCESRYSEIEP
A   WWQSPSIQNGREYH WVTITLDLRQVFQVAYIIKAANAPRPGNWILERSLD GTTFSPWQYYAVSDSECLSRYNITPRRGPPT            YRADDEVICTSYYSRLVP
mA  WWQSPSIQNGREYH WVTVTLDLRQVFQVAYIIIKAANAPRPGNWILERSVD GVKFKPWQYYAVSDTECLTRWKITPRRGPPT           YRADNEVICTSYYSKLVP
M   WWQSPSIKNGIEYH YVTITLDLQQVFQIAYVIVKAANSPRPGNWILERSLD DVEYKPWQYHAVTDTECLTLYNIYPRTGPPS            YAKDDEVICTSFYSKIHP
dA  WWQSPPLSRGMKFN EVNLTINFEQEFHVAYLFIRMGNSPRPGLWTLEKSTDYGKTWTPWQHFSDTPADCETYE   GKDTYKPITRDDVICTTEYSKIVP
B2  WWQSQTMLAGVQYPSSINLTLHLGKAFDITYVRLKF HTSRPESFAIYKRTREDGPWIPYQYYSGS   CENTWSKANR GFIRTGG  DEQQALCTDEFSDISP

B1  STEGEVIFRALDPAFKIEDPY   SPRIQNLLKITNLRIKFVKLHTLGDNLL       DSRMEIREKYYAVYDMVVRGN
S   STEGEVIYRVLDPAIPIPDPY   SSRIQNLLKITNLRLRVNETRLHTLGDNLL      DPRREIREKYYALYELVIRGN
A   LEHGEI HTSLINGRPSADD    LSPKLLEFTSARYIRLRFERIRTLNADLMTLSHREPKELDPML     PRRYYYSIKDISVGGM
mA  LEHGEI HTSLINGRPSADD    PSPQLLEFTSARYIRLRLQRIRTLNADLMTLSHRDLRDLDPIV     TRRYYYSIKDISVGGM
M   LENGEI HISLINGRPSADD    PSPELLEFTSARYIRLRFQRIRTLNADLMFAHKDPREIDPIV      TRRYYVSVKDISVGGM
dA  LENGEI PVMLLNERPSSTNYFNSTVLQEWTRATNVRIRLLRTKNLLGHLMSVARQ    DPTV        TRRYPYSIKDISIGGR
B2  LTGGNV AFSTLEGRPSAYNFDNSPVLQEWVTATDIRVTLNRLNTFGDEVFN        DPKV        LKSYYYAISDFAVGGR

FIG. 11
```

```
B1   CFCYGHASECAPVDGFNEEVEGMVHGHCMCRHNTKGLNCELCMDFYHDLPWRPAEGRNSNACKK
S    CFCYGHASQCAPAPGAPAHAEGMVHGACICKHNTRGLNCEQCQDFYQDLPWHPAEDGHTHACRK
A    CICYGHASSCP    WDE    TTKKLQCQCEHNTCGESCNRCCPGYHQQPWRPGTVSSGNTCEA
mA   CICYGHASSCP    WDE    EAKQLQCQCEHNTCGESCDRCCPGYHQQPWRPGTISSGNECEE
M    CICYGHARACP    LDP    ATNKSRCECEHNTCGDSCDQCCPGYHQKPWRAGTFLTKTECEA
B2   CKCNGHASEC     MKN    EFDKLVCNCKHNTYGVDCEKCLPFFNDRPWRRATAESASECLP
dA   CMCNGHADTCD    VKDPKSPVRILACRCQHHTCGIQCNECCPGYEQKKWRQNTNARPFNCEP

B1   CNCNEHSISCHYDMAVY           LATGNVSGGVCDDCQHNTMGRNCEQCKPFYYQHPERDIRDPNFCER
S    CECNGHSHSCHYDMAVY           LASGNVSGGVCDGCQHNTAGRHCELCRPFYYRDPTKDMRDPAAGRP
A    CNCHNKAKDCYYDESVAKQKKSLNTAGQFRGGVCINCLQNTMGINCETCIDGYYRPHKVSPYEDEPCRP
mA   CNCHNKAKDCYYDSSVAKERRSLNTAGQYSGGGVCVNCSQNTTGINCETCIDQYYRPHKVSPYDDHPCRP
M    CNCHGKAEECYYDENVARRNLSLNIRGKYIGGGVCINCTQNTAGINCETCTDGYYRPKGVSPNYPRPCQP
B2   CDCNGRSQECYYDPELYRST        GHGGHCTNCQDNTDGAHCERCRENFFRLG     NNEACSS
B2t  CDCNGKSRQCIYDRELHRQT        GNGFRCLNCNDNTDGIHCEKCKNGYYRHR     ERDRCLP
dA   CNCHGHSNECKYDEEVNRKGLSLDIHGHYDGGGVCQNCQHNTVGINCNKCKPKYYRPKGKHWNETDVCSP
```

FIG. 12-1

```
B1   CTCDPAGSQNEG                                                                         ICDSYT    DFSTGLIAGQ  CRCKLNVEGEHCDVCKEGTYDLSSEDPFGCKS
S    CDCDPMGSQDGG                                                                         RQDSHD    DPVLGLVSGQ  CRCKEHVGTRCQQCRDGFFGLSASNPRGCQR
A    CNCDPVGSLS                                                                           SVCIKDDLHSDLENGKQPGQ  CPCKEGYTGEKCDRCQLGY            KDYPT CVS
mA   CNCDPVGSLS                                                                           SVCIKDDRHADLANGKWPGQ  CPCRKGYAGDKCDRCQFGY            RGFPN CIP
M    CHCDPIGSLN                                                                           EVCVKDEKHAR  RGLAPGS CHCKTGFGGVSCDRCARGY            TGYPD CKA
B2   CHCSPVGSLS                                                                           TQC         DSYGR   CSCKPGVMGDKCDRCQPGTHSLTEA         GCRP
B2t  CNCNSKGSLS                                                                           ARC         DNSGR   CSCKPGVTGARCDRCLPGFHMLTDA         GCTQDQRLLDSK
dA   CQCDYFFSTGHCEEETGNCECRAAFQPPSCDSCAYGYGYPNCRECECNLNGTNGYHCE AESGQQCPCKINFAGAYCKQCAEGYYG        FP ECKA

B1   CACNPLGTIPGGNPCDSETGHCYCKRLVTGQHCDQCLPEHWGLSNDLD       GCRP
S    CQCNSRGTVPGGTPCDSSSGTFCFCKRLVTGDGCDRCLPGHWGLSHDIL      GCRP
A    CGCNPVGSA  SDEPCT      GPCVCKENVEGKACDRCKPGFY          NLKEKNPRGCSE
mA   CDCRTVGS

MEROSIN FRAGMENTS AND USES THEREOF

This application is a divisional of application Ser. No. 08/125,077, filed Sep. 22, 1993 which is a continuation-in-part application of U.S. Ser. No. 919,951, filed on Jul. 27, 1992, now abandoned, which in turn is a continuation application of U.S. Ser. No. 472,319, filed Jan. 30, 1990, now abandoned, the contents of which are hereby incorporated by reference into the present disclosure.

The present invention was supported by grants DK 30051, CA 45546, CA 28896 and Cancer Center Support Grant CA30199 from the National Institute of Health. The United States Government may have certain rights in this invention.

BACKGROUND OF THE INVENTION

This invention relates generally to basement membranes and specifically to a novel tissue-specific basement membrane-associated protein.

Basement membranes are thin sheets of extracellular matrix separating epithelial cells from underlying tissue stroma. They compartmentalize epithelial and endothelial organs and maintain tissue structures. In some tissues the basement membrane is a product of the interaction of several cell types; for example, the glomerular basement membrane is made by both epithelial and endothelial cells. In skeletal muscle, fibroblasts from the endomysium contribute type IV collagen to the assembly of the basement membrane. The formation of the neural basal lamina requires the interaction of Schwann cells and neurons. Further, basement membranes function in development and tissue repair by promoting attachment, migration and proliferation of cells and by mediating signals for tissue interactions.

All basement membranes contain laminin, type IV collagen, entactin and heparan sulfate proteoglycan. Laminin is a large glycoprotein composed of three polypeptide chains, a 400 kD A chain and two B chains of about 200 kD each. The amino-terminal two thirds of the A chain is homologous to the B1 and B2 chains while the carboxy-terminal third has a distinct structure.

Recent studies have revealed that several genetically distinct subunit chains and consequently several laminin isoforms exist. In addition to the EHS laminin chains, A, B1 and B2, merosin (also known as laminin M chain), a homologue of the A chain (Leivo et al., *Proc. Natl. Acad. Sci. USA* 85:1544–1548 (1988); Ehrig et al., *Proc. Natl. Acad. Sci. USA* 87:3264–3268 (1990)), s-laminin (S chain), a homologue of the B1 chain (Hunter et al., *Nature* 338:229–234 (1989)) and B2t, a truncated homologue of the B2 chain (Kallunki et al., *J. Cell Biol.* 119:679–693 (1992)), have been characterized. Recently partial sequence of another B1 chain variant in avian eye was reported (O'Rear et al., *J. Biol. Chem.* 267:20555–20557 (1992)). K-laminin and kalinin are laminin isoforms that are present in epithelial basement membranes. K-laminin contains the B1 and B2 chains and has a third 190 kD chain immunologically distinct from the A chain (Marinkovich et al., *J. Cell Biol.* 119:695–703 (1992)). Kalinin has three subunits of which the largest one is immunologically related to one chain of K-laminin (Rouselle et al., *J. Cell. Biol.* 114:567–576 (1991); Marinkovich et al., *J. Biol. Chem.* 267:17900–17906 (1992)). For terminology of the laminins, see Engvall, 1993, *Kidney International* 43:2–6, which is incorporated herein by reference, and FIG. 13.

Laminin promotes attachment, spreading, motility and growth of a variety of cell types. One of the most striking features of laminin is its capacity to promote outgrowth of neurites from cultured neuronal cells. A major site of cell adhesion and the neurite-promoting activity appear to reside in the globular domain at the end of the long arm of this molecule.

The metastatic propensity of certain tumor cells may also be influenced by laminin. For example, laminin has been shown to mediate the attachment of malignant carcinoma cells to type IV collagen and to increase the metastatic potential of murine melanoma cells. Other basement membrane proteins and their receptors may be involved in the adhesion of metastasizing tumor cells to basement membranes of blood vessels and other epithelial tissues.

Because of the critical role of basement membranes in development, tissue repair, neurite growth and cancer, there exists a need for the identification of new basement membrane components. The present invention satisfies this need.

SUMMARY OF THE INVENTION

This invention provides an isolated nucleic acid molecule encoding a 380–400 KDa subunit of the protein merosin. Also provided are isolated nucleic acid molecules which encode merosin fragments. The invention further provides antibodies, vectors, and the expression of recombinant proteins by use of a host/vector system. The invention also provides the use of merosin to promote neurite growth.

BRIEF DESCRIPTION OF DRAWINGS

FIG. 3 shows immunoblotting of placental extract with antiserum. NaDodSO$_4$ extract of placenta (lanes 1) and the purified fragment of merosin polypeptide from a pepsin digest of placenta (lanes 2) were electrophoresed on a 2–16% gradient acrylamide gel in the presence of NaDodSO$_4$ and transferred to nitrocellulose. The blot in (a) was stained with a peptide antiserum raised to a 13-amino acid peptide corresponding to residues 476–488 of the merosin polypeptide in FIG. 1. The blot in (b) was stained with monoclonal antibody that recognizes COOH-terminal fragments of merosin polypeptide. For comparison, a blot of mouse laminin was stained with anti-laminin (c). Arrowhead shows the position of the top of the separating gel and numbers (KDa) indicated the positions of molecular weight markers.

FIG. 4A: NaDodsO$_4$-polyacrylamide gel electrophoresis of rat laminin (lane 1) and the merosin-containing fraction from human placenta (lane 2). Positions of molecular weight markers are shown on the left. FIG. 4B: Electron microscopy after rotary shadowing of the merosin-containing preparation. FIG. 4C: ELISA in microtiter wells coated with the merosin-containing preparation and in wells coated with the large pepsin fragment of laminin. The antibodies were 3E5 (■; anti-B1), 2E8 (●; anti-B2), 11D5 (Δ; anti-A), and 2G9 (▲; anti-merosin).

FIG. 6 shows the complete nucleotide sequence (SEQ ID NO:3) of human merosin cDNA clones and deduced complete amino acid sequence (SEQ ID NO:4) of the entire protein. First line, nucleotide sequence of cDNA clones characterized in this study. Second line, deduced amino acid sequence from the cDNA clones together with the previously determined carboxyl terminal end amino acid sequence (Ehrig et al., Proc. Natl. Acad. Sci. USA 87:3264–3268 (1990)), incorporated herein by reference. The putative signal peptidase cleavage site is indicated by a triangle. The cysteine residues are circled, and potential attachment sites for asparagine-linked oligosaccharides are boxed.

Figure 7A:
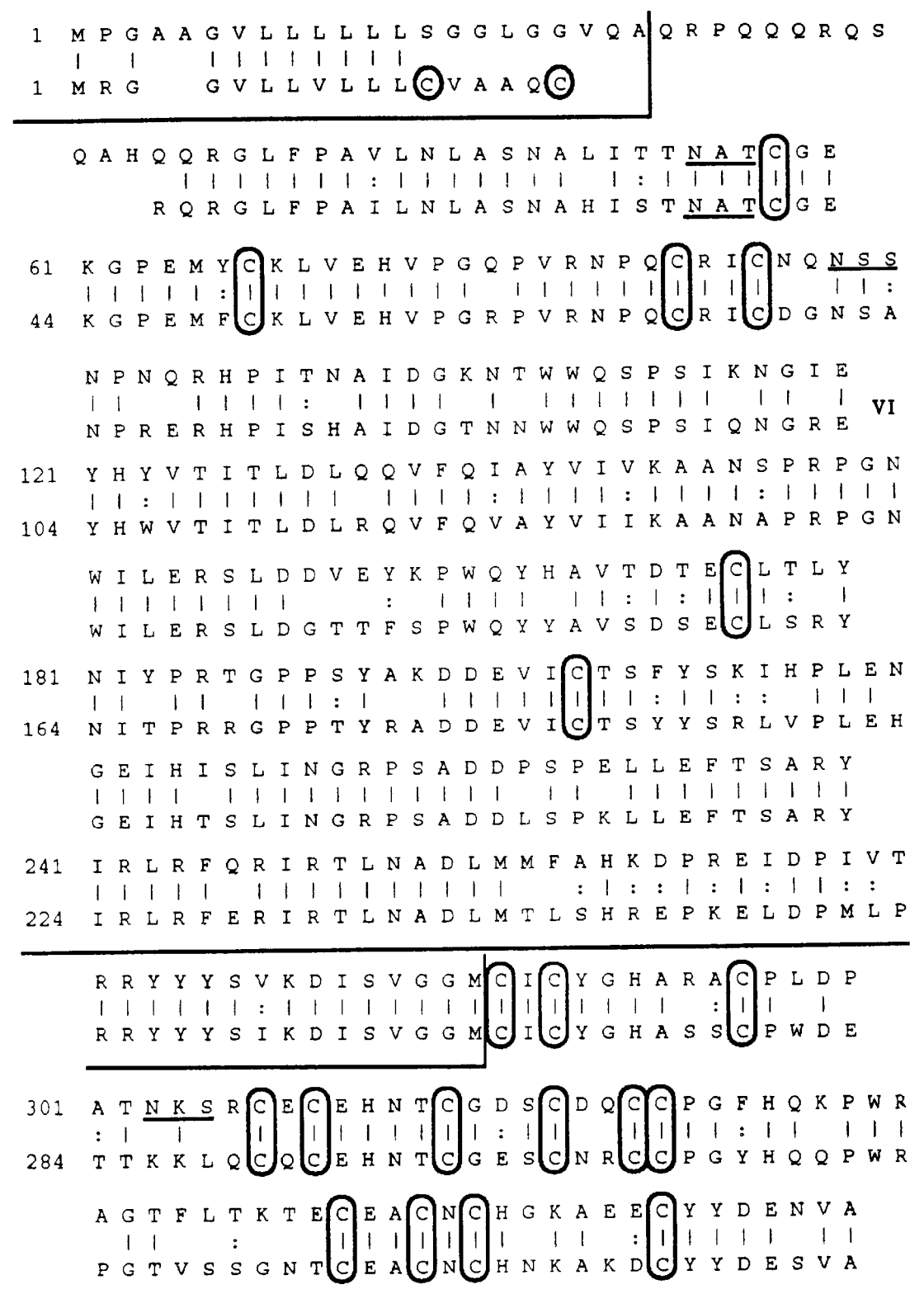
Figure 7B:
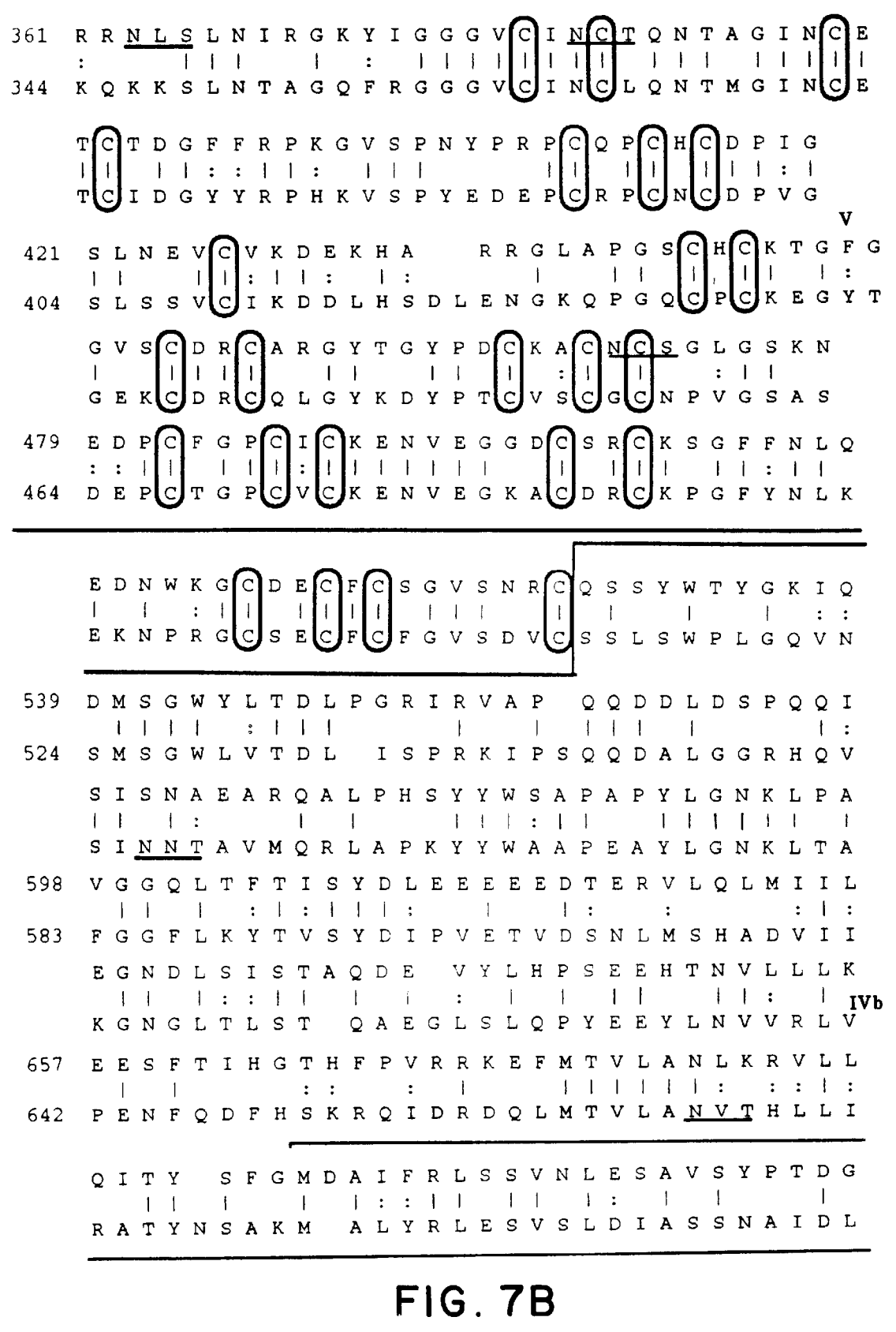
Figure 7C:
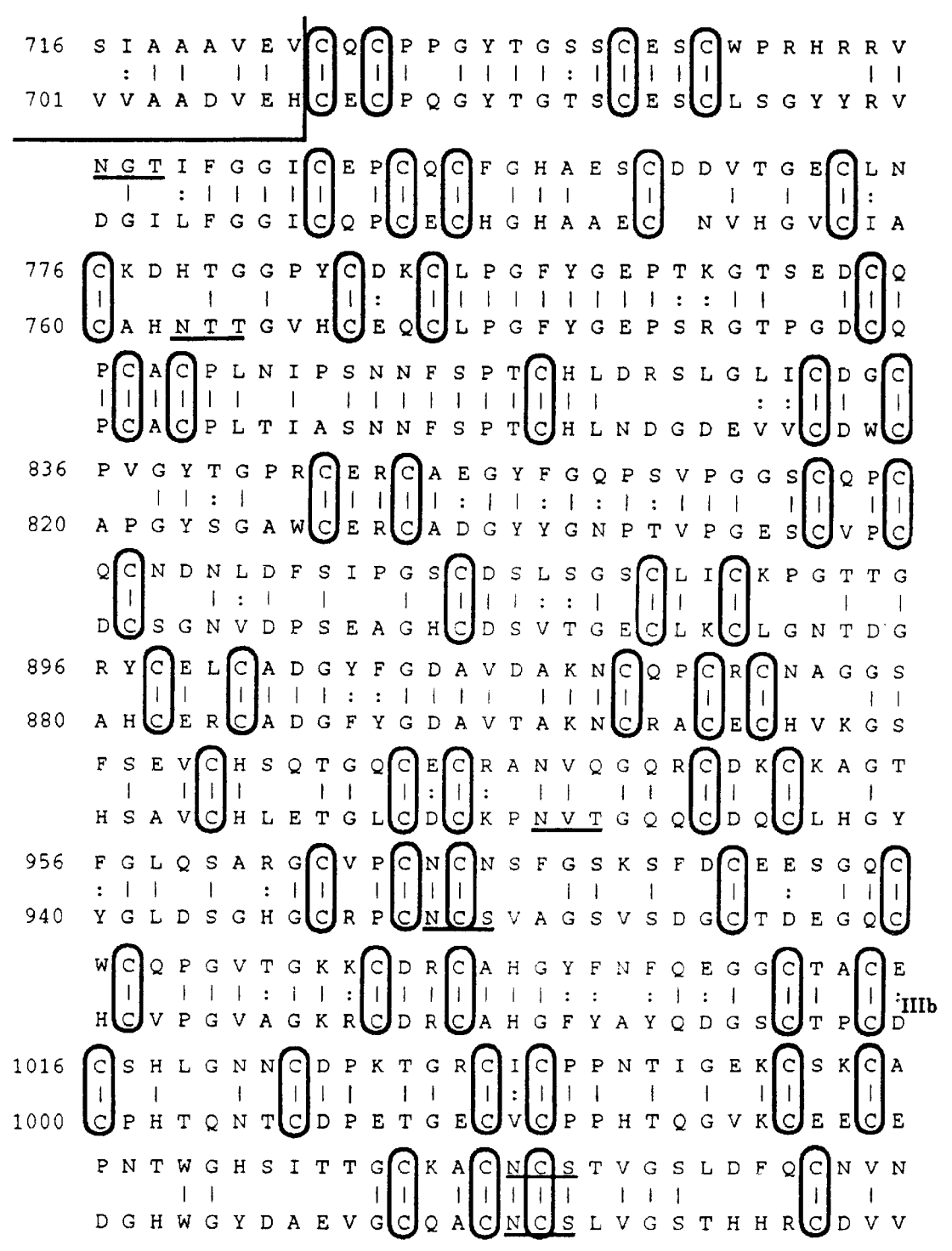
Figure 7D:
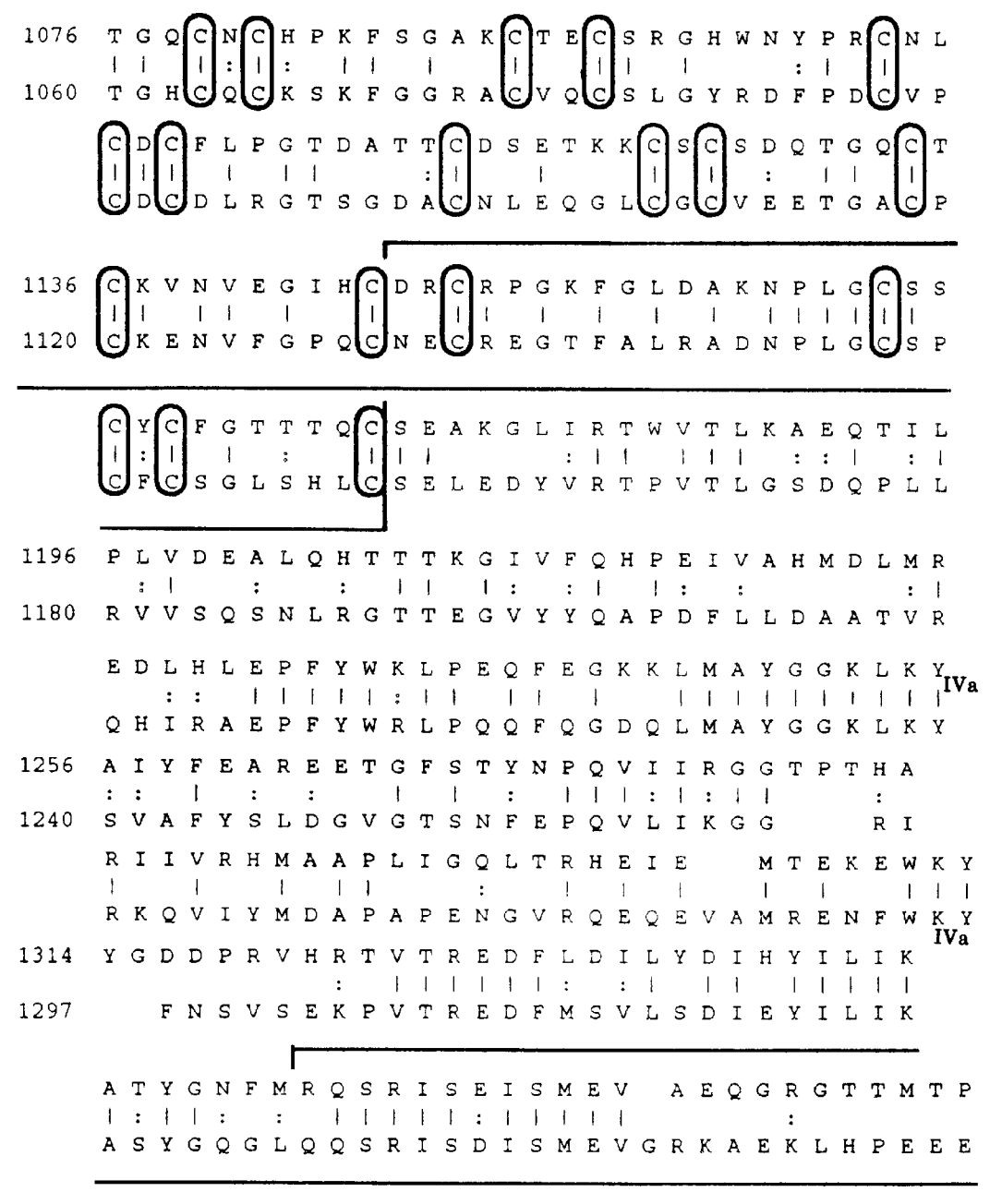
Figure 7E:
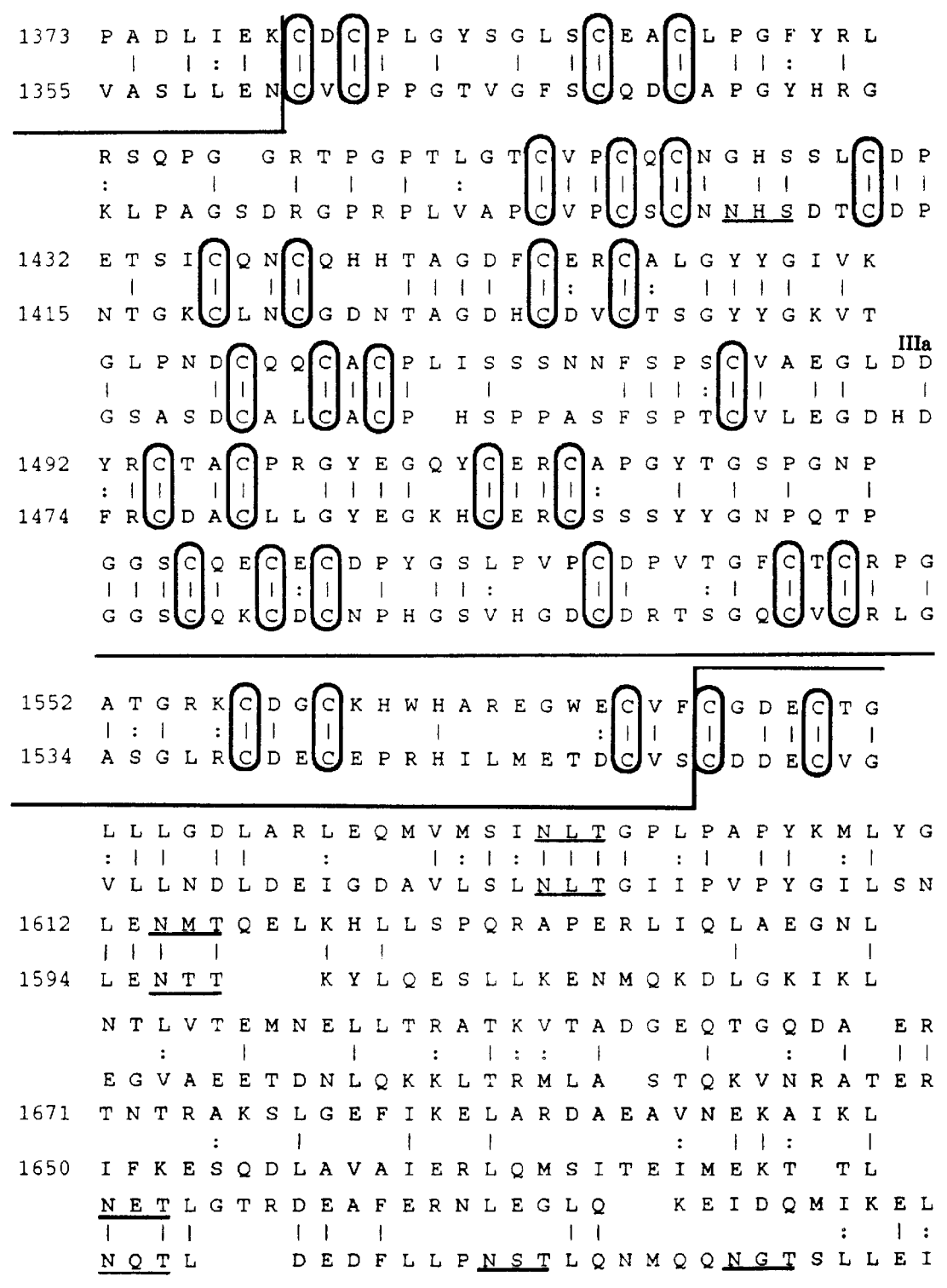
Figure 7F:
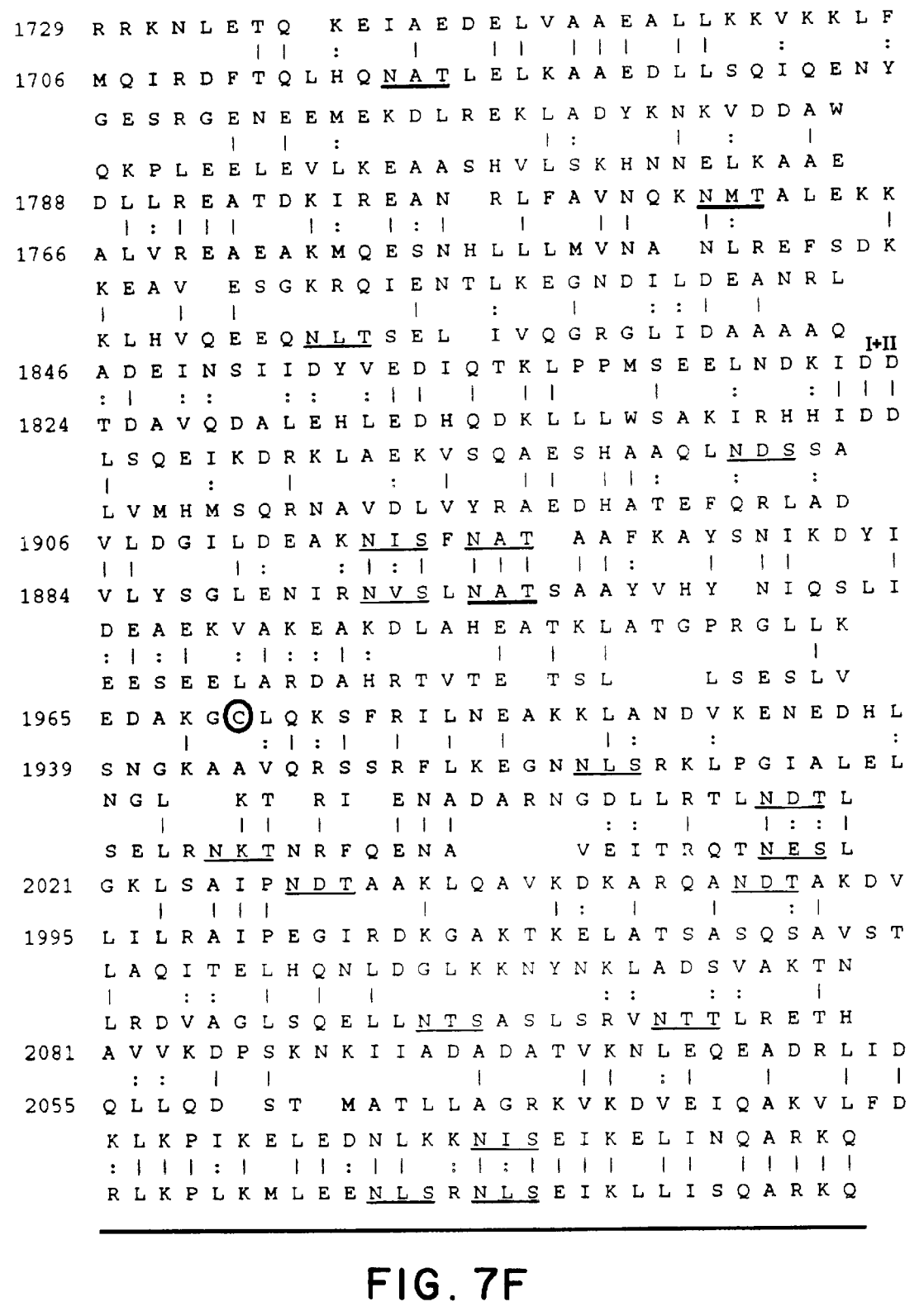
Figure 7G:
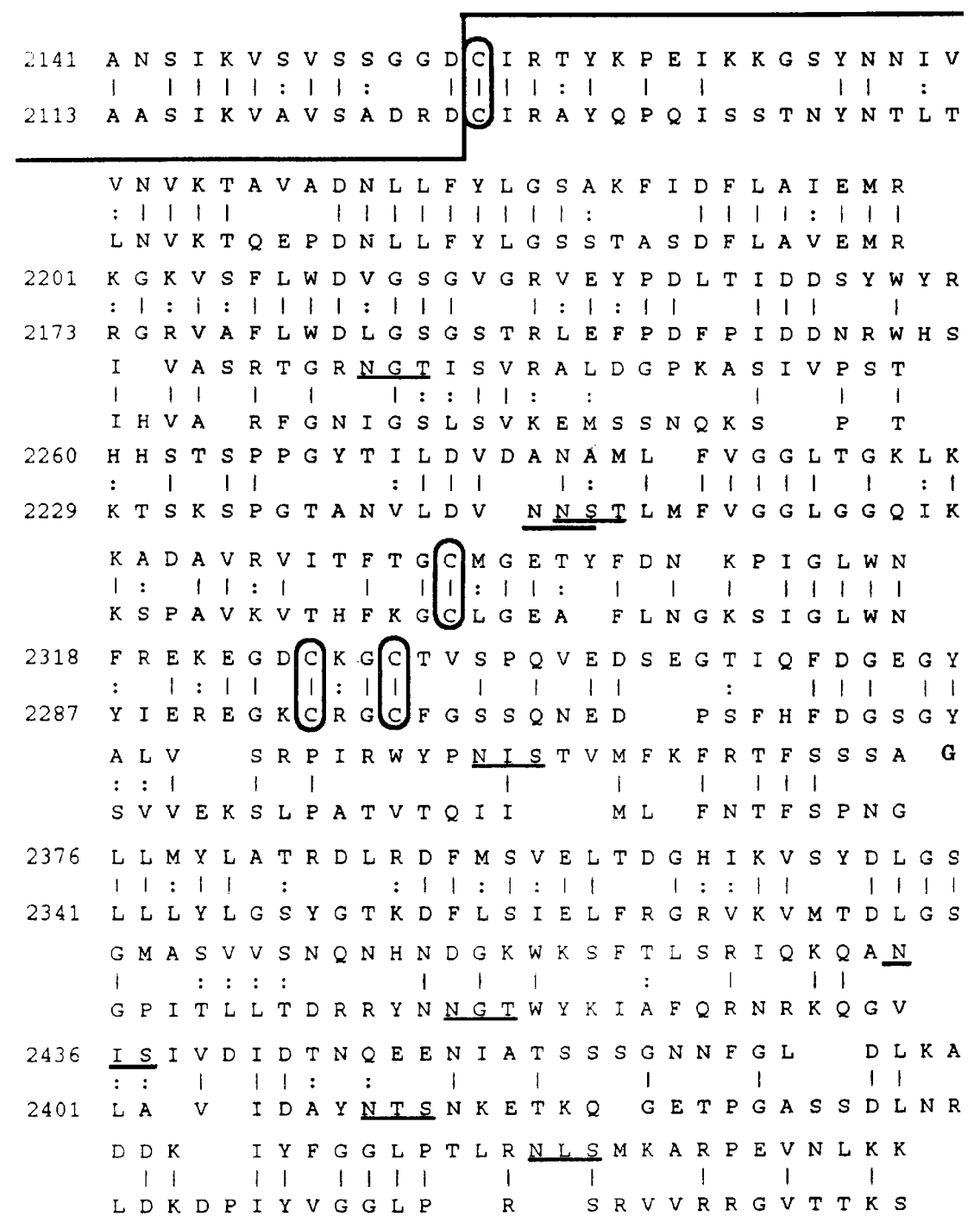
Figure 7H:
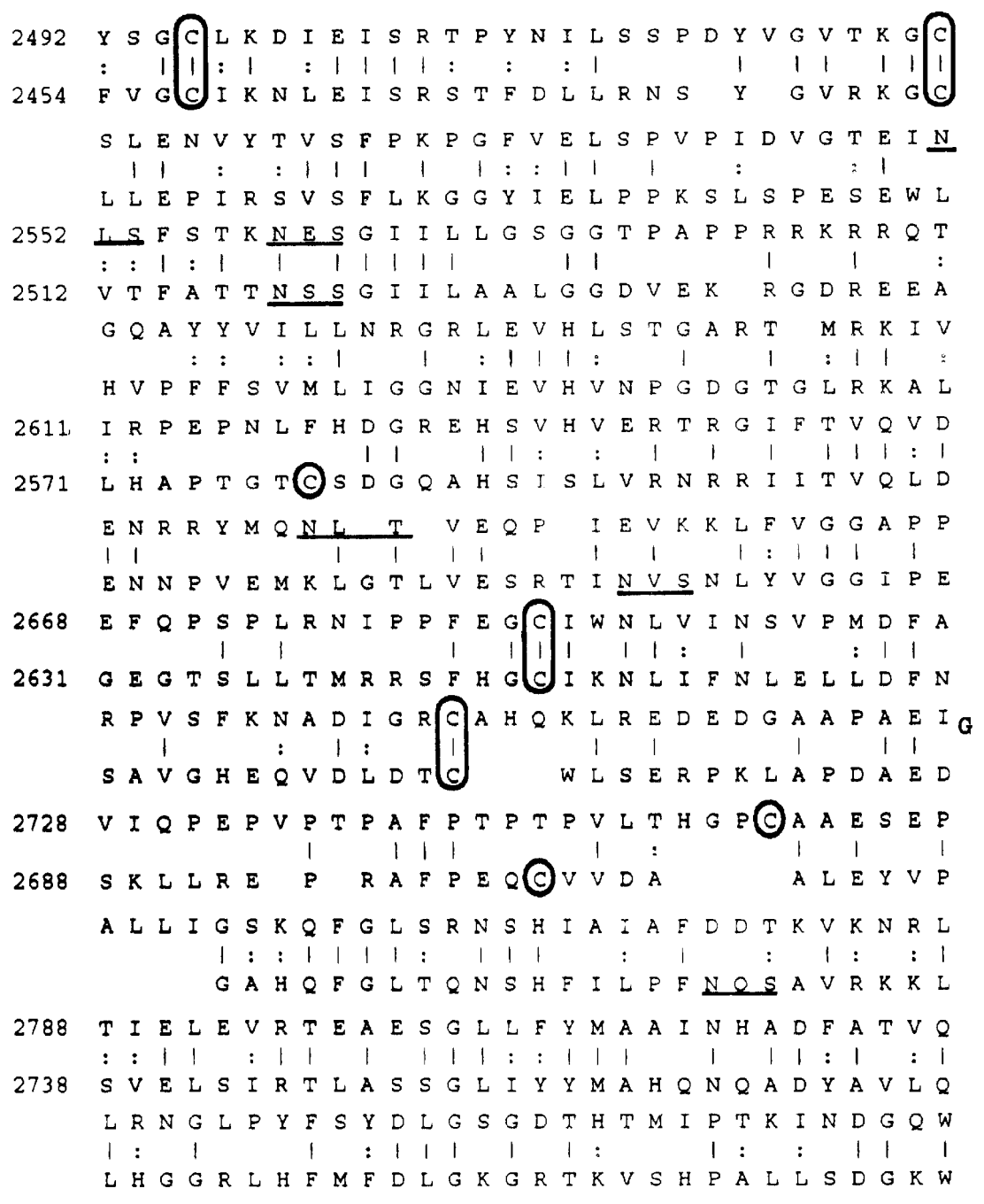

FIG. 7 is an alignment of amino acid sequences of the M (merosin) (SEQ ID NO:4) and A (SEQ ID NO:4) chains of human laminin-type proteins. The upper line shows the amino acid sequence of merosin, and the second line shows the amino acid sequence of the laminin A chain. Both amino acid sequences are numbered from the initiator methionine. All cysteines are circled and N-glycosylation sites are underlined. The structural domains are boxed and indicated by Roman numerals on the right. SP=signal peptide.

FIGS. 10A through 10H show in situ hybridization of merosin MRNA in 17-week-old fetal tissues. In kidney (FIGS. 10A and B) signals are seen in mesenchymal cells adjacent to condensing pretubular cells and ureter-derived tubules (t) in the outer cortex. Secretory tubules of the nephron and blood vessels are negative. In heart muscle (FIGS. 10C and D) signals can be observed in cardiomyocytes throughout the muscle. In sections of skin (FIGS. 10E and F) no grains are seen over the epithelial cells of epidermis (e), while strong signal can be observed in the condensing papillary mesenchymal cells (p) and a developing hair follicles (f). In lung (FIGS. 10G and H) signals are present in smooth muscle cells of the peribronchial arterial wall, but alveolar and bronchial cells are negative. Bar A-D 200 μm and E-H 100 μm.

FIG. 11 is an alignment of domains VI of the known human A - and B-type laminin chains, the rat S chain, the mouse A chain and the Drosophila A chain. Amino acids that are identical in half of the chains are shaded, and dark shading indicates conserved change Phe (F) <-> Tyr (Y). Abbreviations: B1(SEQ ID NO:6), human B1 chain; S, rat S chain (SEQ ID NO:7); A, human A chain (SEQ ID NO:8); mA, mouse A chain (SEQ ID NO:9); M, human M chain (SEQ ID NO:10); B2, human B2 chain (SEQ ID NO:12); dA, Drosophila A chain (SEQ ID NO:11).

FIG. 12 is an alignment of domains V of the known human A- and B-type chains, the rat S chain, the mouse A chain and the Drosophila A chain. Amino acids that are identical in half of the chains are shaded, and dark shading indicates conserved change Phe (F) <-> Tyr (Y). Abbreviations: B1, human B1 chain (SEQ ID NO:13); S, rat S chain; A, human A chain; mA, mouse A chain; M, human M chain; B2, human B2 chain; dA, Drosophila A chain.

DETAILED DESCRIPTION OF THE INVENTION

This invention provides a cDNA molecule encoding the major subunit of human merosin protein which is structurally related to laminin. The merosin protein has an apparent molecular weight of about 800 kd and is composed of four polypeptides having apparent molecular weights of 300, 200, 200 and 80 kD, the 300 kD polypeptide being joined to the 200 kD polypeptides by disulfide bonds, and the 300 kD and 80 kD polypeptides comprising the 380–400 KDa merosin subunit having substantially the amino acid sequence shown in FIG. 6. Merosin is found in placenta, striated muscle, peripheral nerve, trophoblasts and human Schwann cell neoplasms, among other tissues.

Leivo et al., Proc. Natl. Acad. Sci. USA 85:1544–1548 (1988), which is incorporated herein by reference, describes the isolation of a 65-KDa and an 80 KDa segment of the basement-membrane-associated polypeptide merosin. These two precursor segments, the full length merosin polypeptide, fragments of the merosin polypeptide, and proteins comprising any of these segments, polypeptide, or fragments have also been termed merosin. Because the 65 KDa and 80 KDa proteins appear to be segments of the 380–400 KDa merosin polypeptide contained within an 800 KDa protein complex, the term merosin has now also been applied to the 800 KDa protein described herein. The 380–400 KDa subunit is designated merosin polypeptide, merosin subunit, M chain, or laminin M chain.

Figure 1A:
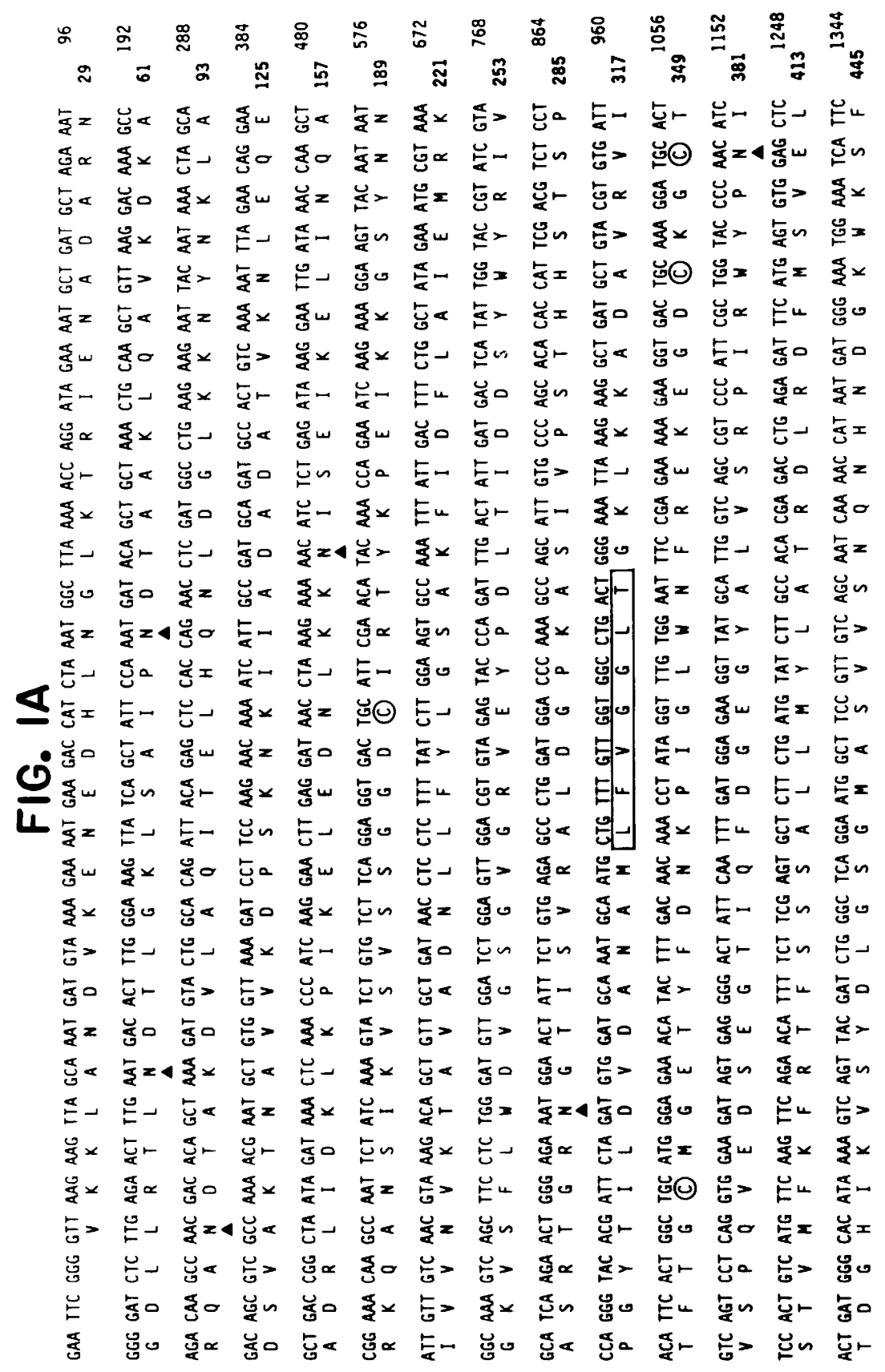
Figure 1B:
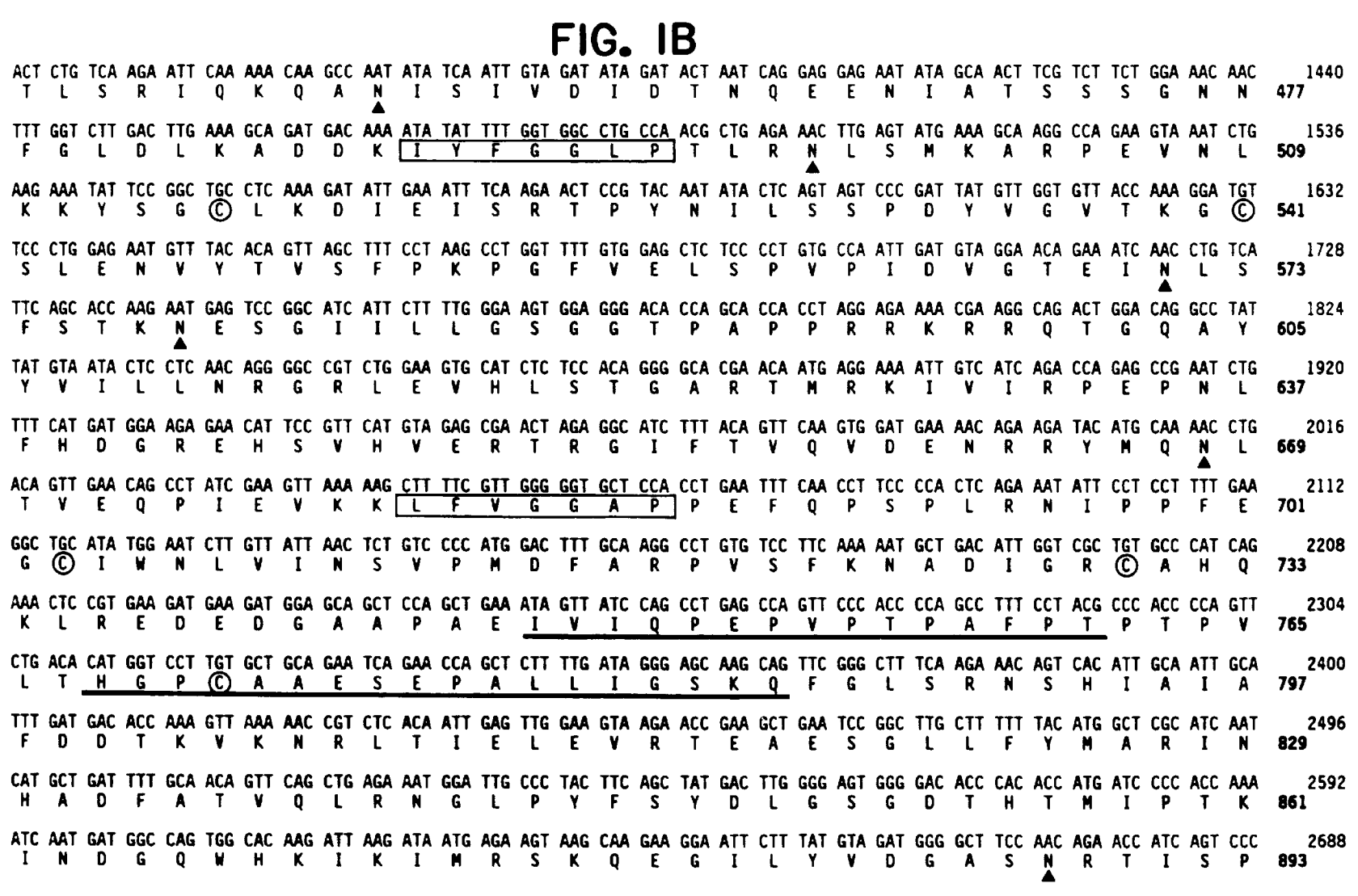
Figure 2:
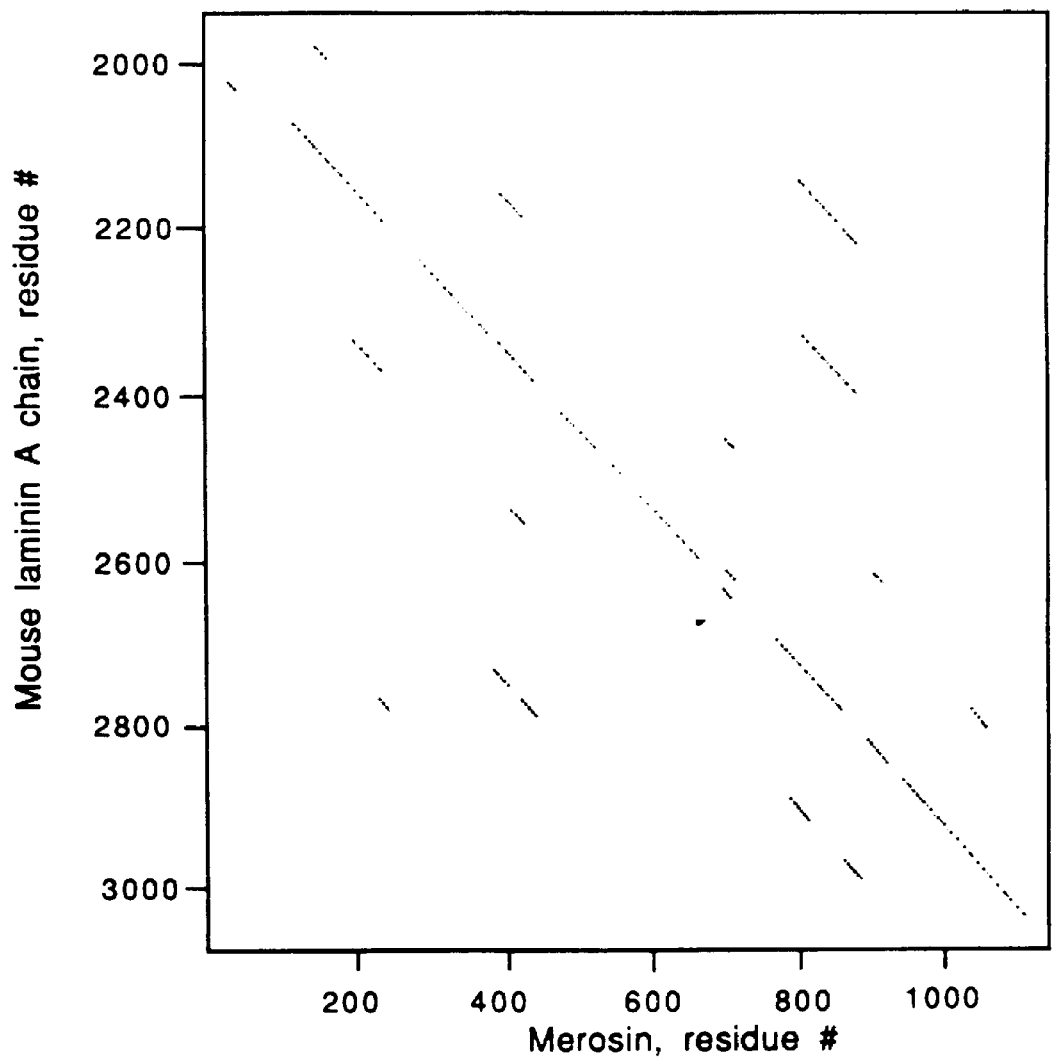
FIG. 2 shows a comparison of the amino acid sequences of merosin fragment and the COOH-terminal portion of the mouse laminin A chain by dot matrix plotting. Sequences were compared using the Micro Genie matrix comparison program. The frame was set at eight amino acids with a minimal match of 40%.
Figure 4A:
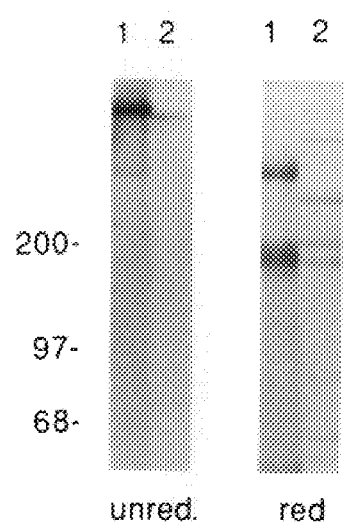
FIGS. 4A through C show an analysis of intact merosin from placenta.
Figure 4B:
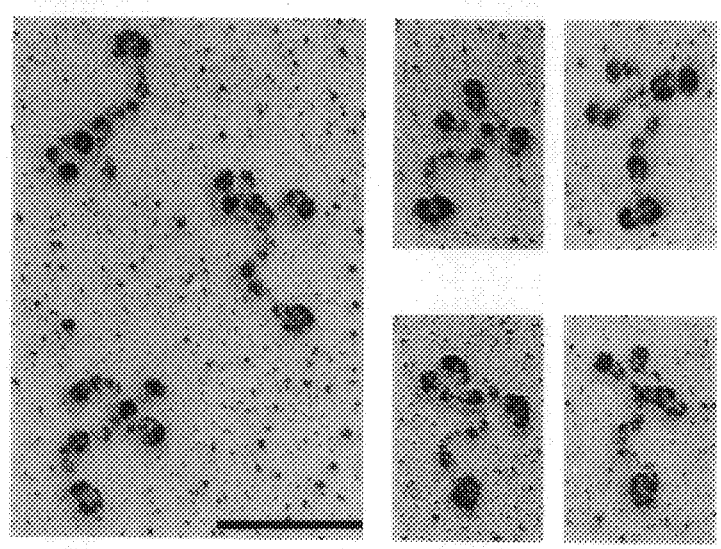
Figures 1, 4C:
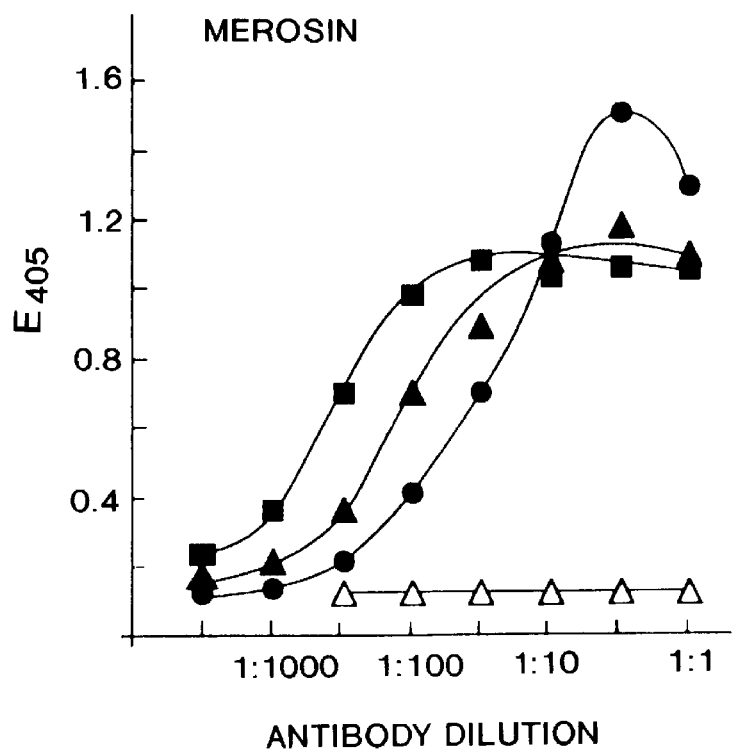
FIG. 1 shows the DNA sequence of a partial merosin polypeptide cDNA (SEQ ID NO:2) and the deduced amino acid (SEQ ID NO:2) sequence. Potential N-glycosylation sites are indicated by (▲) and cysteines are circled. Sequences obtained by amino acid sequencing are underlined. Conserved motifs of amino acid sequence are boxed.
Figures 2, 4C:
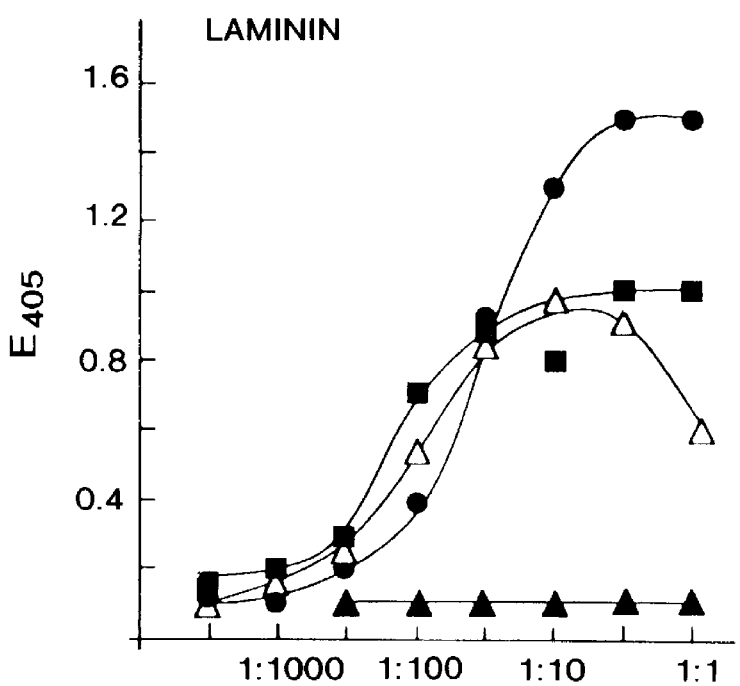
Figure 6D:
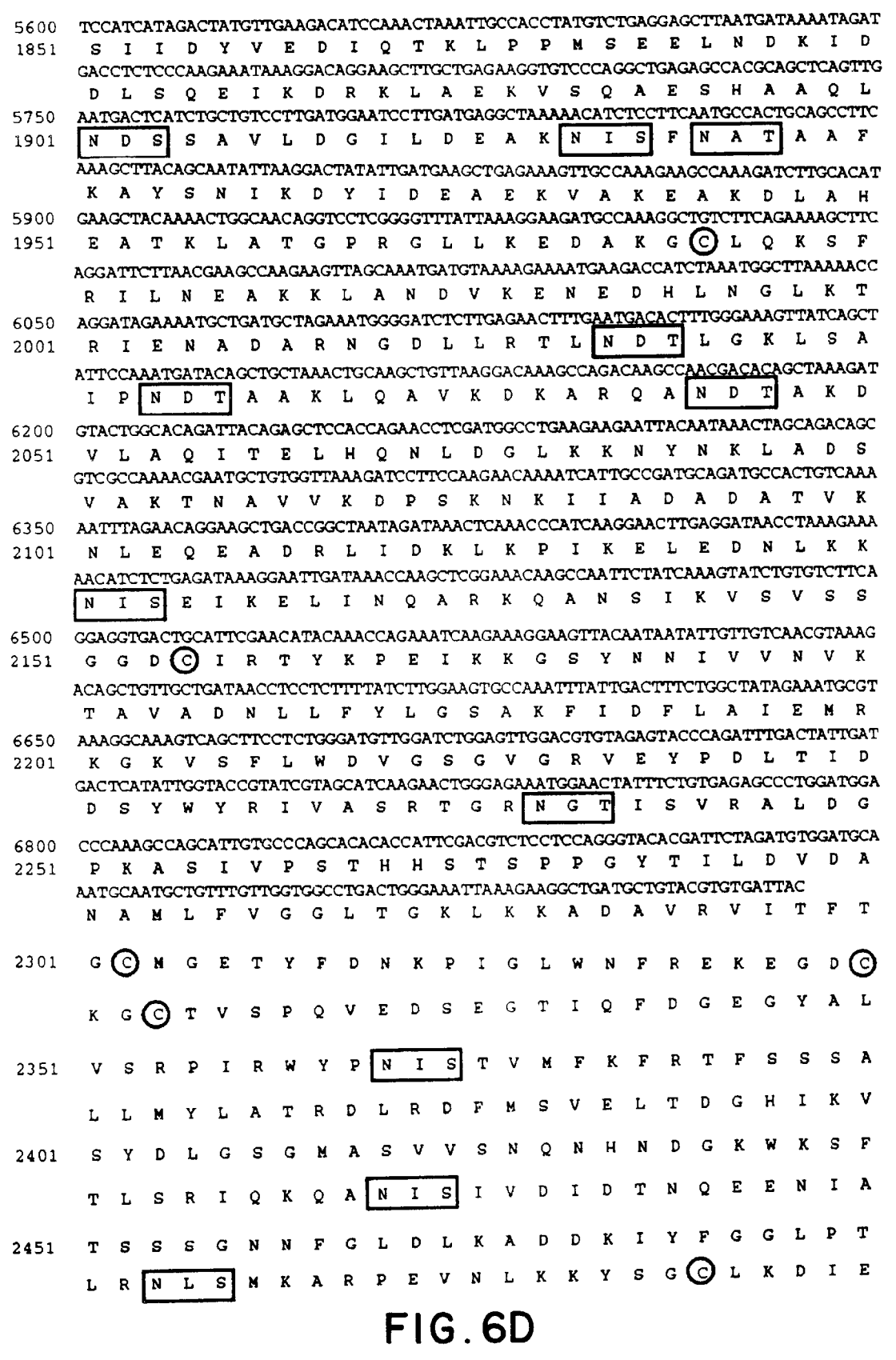
Figure 6E:
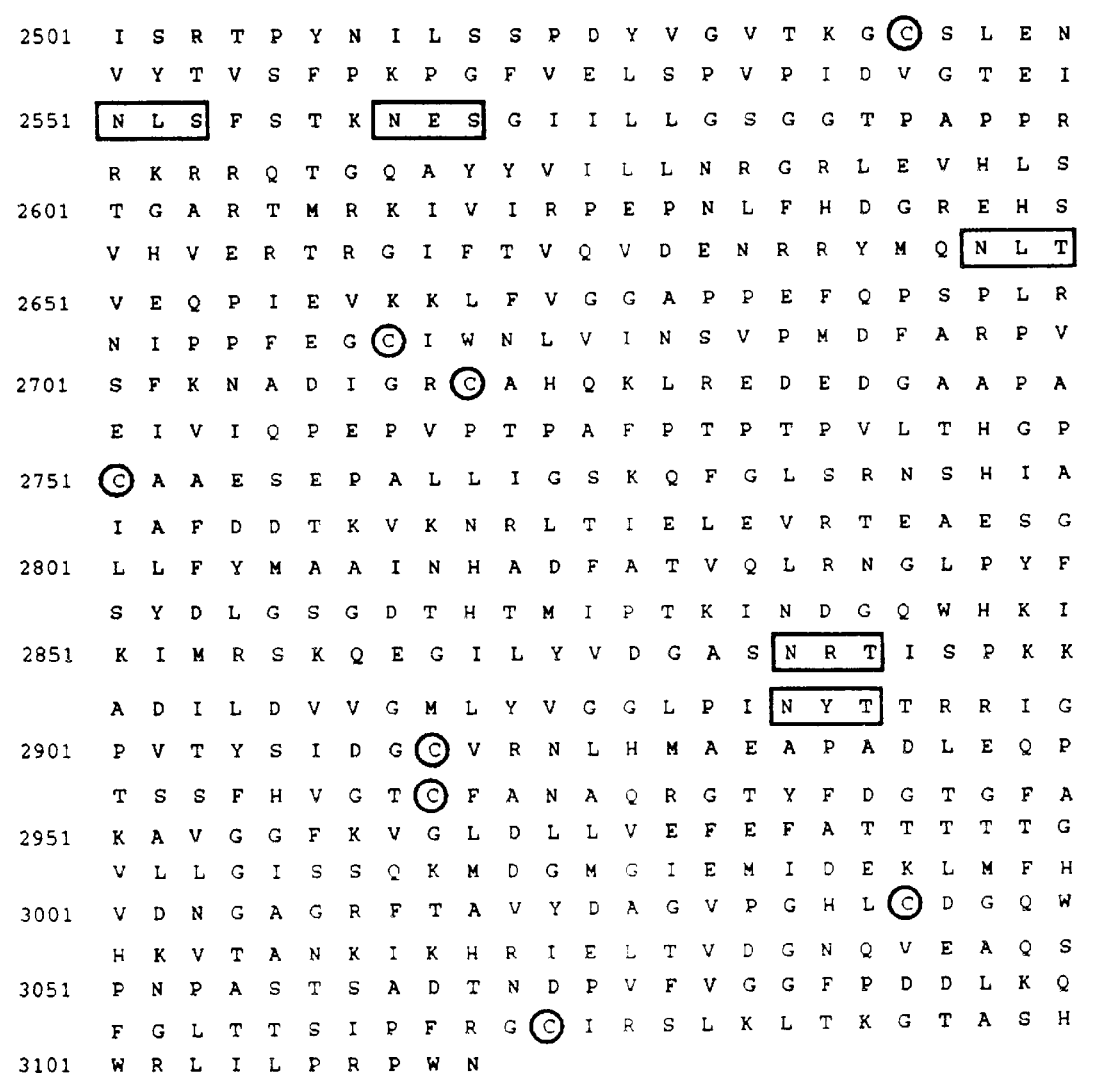

It is understood that limited modifications may be made to the primary sequence of merosin subunit without destroying its biological function, and that only a portion of the entire primary structure may be required in order to effect activity. One such biological active fragment is a molecule having substantially the sequence shown in FIG. 1. In a separate embodiment of the invention, the merosin subunit has an amino acid sequence substantially similar to that shown in FIG. 6. Minor modifications of these sequences which do not destroy the activity of the proteins also fall within the definition of merosin and within the definition of the protein claimed as such. Moreover, fragments of the sequences of FIGS. 1 or 6, but not a fragment consisting solely of the previously described 80 Kd fragment, which retain the function of the entire protein, as determined by the merosin activity assay described in Example II below, and as defined by the protein's ability to elicit merosin-specific antibodies are included within the definition. It is understood that minor modifications of primary amino acid sequence may result in proteins which have substantially equivalent or enhanced function as compared to the sequences set forth in FIGS. 1 or 6. These modifications may be deliberate, as through site-directed mutagenesis, or synthesis of merosin analogs, or may be accidental such as through mutation in hosts which are merosin producers. All of these modifications are included as long as merosin biological function is retained. The nucleic acid sequences shown in FIGS. 1 and 6 are useful in the production of recombinant merosin and merosin fragments. Nucleic acid fragments of at least 10 nucleotides are also useful as hybridization probes. The probes are useful to identify tissue (as set forth in more detail below) to isolate the genomic gene encoding merosin, which has now been localized to chromosome 6q22–>23, or to identify nucleic acid encoding merosin-like proteins. The isolated nucleic acid fragments also are useful to generate novel peptides. These peptides, in turn, are useful as immunogens for the generation of polyclonal and monoclonal antibodies. Methods of preparing and using the probes and immunogens are well known in the art, and are briefly described below.

Also included within the scope of this invention are nucleic acid molecules that hybridize under stringent conditions to the nucleic acid molecules, the sequences of which are shown in FIGS. 1 and 6. Such hybridizing nucleic acid molecules or probes, can by prepared, for example, by nick translation of the nucleic acid molecules of FIGS. 1 or 6, in which case the hybridizing nucleic acid molecules can be random fragments of the molecules, the sequences of which are shown in FIGS. 1 and 6. For methodology for the preparation of such fragments, see Sambrook et al., *Molecular Cloning: A Laboratory Manual* Cold Spring Harbor Press, Cold Spring Harbor, N.Y. (1989), incorporated herein by reference. As used herein, "nucleic acid" shall mean single and double stranded DNA and RNA.

Further, various molecules can be attached to merosin subunit, for example, other proteins, carbohydrates, or lipids. Such modifications are included within the definition of merosin.

"Purified", when used to describe the state of merosin, denotes the protein free of a portion of the other proteins and molecules normally associated with or occurring with merosin in its native environment. As used herein the term "native" refers to the form of a protein, polypeptide, antibody or a fragment of thereof that is isolated from nature or that which is without an intentional amino acid substitution.

As used herein, the term "antibody" or "immunoglobulin" refers to a protein that is produced in response to immunization with an antigen and specifically reacts with the antigen. This includes polyclonal as well as monoclonal antibodies. Human and mammalian, for example, mouse, rat, rabbit and goat, are intended to be included in this definition. The most predominant human antibody produced is of the IgG isotype, having two light and two heavy chains linked by disulfide bonds, which constitute about 80% of total serum antibodies.

As used herein, "antibody" also encompasses fragments of antibodies. The antibody fragments retain at least some ability to selectively bind with its antigen. Also encompassed by this invention are antibody fragments that have been recombinantly or chemically synthesized that retain the ability to bind the antigen of the corresponding native antibody. The ability to bind with an antigen or hapten is determined by antigen-binding assays known in the art such as antibody capture assays (See, for example, Harlow and Lane, *Antibodies, A Laboratory Manual*, Cold Spring Harbor Laboratory, Cold Spring Harbor, N.Y. (1988)). Antibody fragments retaining some binding affinity include, but are not limited to: Fab (the fragment which contains a monovalent antigen-binding fragment of an antibody molecule produced by digestion with the enzyme papain to yield an intact light chain and a portion of one heavy chain); Fab' (the fragment of an antibody molecule obtained by treating with pepsin, followed by reduction, to yield an intact light chain and a portion of the heavy chain; two Fab' fragments are obtained per antibody molecule); $(Fab')_2$, the fragment of the antibody that is obtained by treating with the enzyme pepsin without subsequent reduction; $F(ab')_2$ is a dimer of two Fab' fragments held together by two disulfide bonds; Fv and single chain antibodies (SCA).

"Isolated" when used to describe the state of the nucleic acids encoding merosin, denotes the nucleic acids free of at least a portion of the molecules associated with or occurring with nucleic acids in the native environment.

"Recombinant expression vector" includes vectors which are capable of expressing DNA sequences contained therein, where such sequences are operatively linked to other sequences capable of effecting their expression. It is implied, although not always explicitly stated, that these expression vectors must be replicable in the host organisms either as episomes or as an integral part of the chromosomal DNA. In sum, "expression vector" is given a functional definition, and any DNA sequence which is capable of effecting expression of a specified DNA sequence disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Host-vector system" refers to cells which have been transfected with vectors constructed using recombinant DNA techniques. The vectors and methods disclosed herein are suitable for use in host cells over a wide range of procaryotic and eucaryotic organisms.

Reference is made to standard textbooks of molecular biology that contain definitions and methods and means for carrying out basic techniques, encompassed by the present invention. See, for example, Maniatis et al., *Molecular Cloning: A Laboratory Manual*, Cold Spring Harbor Laboratory, N.Y. (1982) and Sambrook et al., *Molecular Cloning: A Laboratory Manual*, Cold Spring Harbor Laboratory, N.Y. (1989) and the various references cited therein. This reference and the cited publications are expressly incorporated by reference into this specification.

In addition, recombinant DNA methods currently used by those skilled in the art include the polymerase chain reaction (PCR) which, combined with the synthesis of oligonucleotides, allows easy reproduction of DNA sequences. A DNA segment of up to approximately 6000 base pairs in length may be amplified exponentially starting from as little as a single gene copy by means of PCR. In this technique a denatured DNA sample is incubated with two oligonucleotide primers that direct the DNA polymerase-dependent synthesis of new complementary strands. Multiple cycles of synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202 all of which are hereby incorporated by reference.

With regard to the present invention, the cDNA shown in FIGS. 1 or 6, or any portion of them can be reproduced for cloning and expression purposes by amplifying the desired sequence with PCR and cloning it into a suitable vector as is well known in the art.

Detection methods for the presence of nucleic acid or protein in cells include hybridization of a nucleic acid probe with the nucleic acid of a cell and cell staining with polyclonal or monoclonal antibodies. Such techniques are accomplished by methods well-known to those skilled in the art. See, for example, Harlow and Lane, *Antibodies: A Laboratory Manual*, Cold Spring Harbor, 1988, hereby incorporated by reference.

Monoclonal and polyclonal antibodies against merosin were prepared according to procedures well known in the art. The specificity of the antibodies is examined by carrying out enzyme immunoassays and immunoblotting of placental extracts.

For example, monoclonal antibodies are prepared by immunizing an animal with material containing the protein, such as an extract of human placenta tissue, followed by isolating antibody-producing hybridoma cells, as is well known in the art. (See, for example, Harlow and Lane, *Antibodies: A Laboratory Manual*, supra, and the references cited therein, all which are incorporated by reference into this specification.) Anti-merosin antibodies are selected by performing immunofluorescence analysis of tissue sections where merosin is localized in the basement membranes of trophoblasts, striated muscle and Schwann cells, and other sites. The identification of antibodies is confirmed by immunoblotting and immunoprecipitation which reveals one or more of the polypeptides described above. The appropriate hybridoma is reactive with purified merosin subunit or merosin fragments. Merosin fragments can be prepared by expressing the merosin cDNA shown in FIG. 1, or alternatively, subjecting the cDNA molecules, the sequences of which are shown in FIG. 1 and 6, to restriction enzyme digestion and subsequent purification of the restriction enzyme fragments. These methods are well known to those of skill in the art, Sambrook et al., supra, hereby incorporated by reference. The nucleic acid fragments are then expressed in a procaryotic or eucaryotic expression vector as described above.

Alternatively, anti-merosin antibodies can be prepared by immunizing an animal with synthetic peptides or recombinant protein fragments prepared from molecules having the sequences shown in FIGS. 1 or 6, or from restriction enzyme fragments, described above. One molecule demonstrated to be suitable for antibody production is the molecule having the sequence shown in FIG. 1. A synthetic peptide suitable for antibody production is described in Example I. Selection of anti-merosin antibodies is performed as described above.

The COOH-terminal portion of merosin is structurally related to the COOH-terminus of the laminin A-chain. However, the amino acid sequence of merosin is 61% and 62% different from the homologous portions of mouse and human laminin A chains, respectively. Affinity purified antibodies stain two bands, suggesting that the merosin polypeptide is processed into two fragments of approximately 300 kD and 80 kD respectively.

cDNA clones for merosin A chain were isolated from a human placental lambda gt11 cDNA expression library using affinity purified antibodies specific for merosin. Two cDNA clones, designated 271 and 225, with inserts of 3.6 and 1.7 kb respectively were selected for sequencing. The nucleic acid sequence of the cDNA revealed a 3.4 kb open reading frame followed by a 155 bp untranslated 3' region. The cDNA and deduced amino acid sequences are shown in FIG. 1. $NH_2$-terminal amino acid sequences of the fragments isolated from peptic or chymotryptic digests of placenta, and the $NH_2$-terminal amino acid sequences of a 16 kD fragment generated with thrombin were contained within the deduced sequence, thus defining the clones as merosin cDNA. RNA blot analysis revealed a single transcript of about 10 kb in human placental RNA.

The deduced partial sequence of merosin comprises 1130 amino acids and contains 13 potential sites of N-glycosylation. The sequence includes five repeats of about 190 amino acids. These repeats contain a conserved seven amino acid long sequence, LFVGGLP or variations thereof. This is followed 17–21 and 40–43 residues later by cysteines most of which are preceded by glycines. The average identity among the five repeats is about 25%.

Comparative analysis of the amino acid sequence of merosin with known proteins revealed a striking similarity to the mouse and human laminin A chains. No other significant similarities were found upon search of the data banks. The five repeats of merosin are also present in the COOH-terminal portion of the laminin A chain. The overall identity between the merosin sequence in FIG. 1 and the corresponding portion of the mouse laminin A chain is 39%.

The partial cDNA clone, the sequence of which is provided in FIG. 1, was used to isolate the full length sequence encoding merosin polypeptide. Several libraries were made from human placental poly(A) RNA and probed with merosin-encoding sequences. Five overlapping cDNA inserts were pieced together to generate the full length sequence, which is shown in FIG. 6.

The human M chain is 30 residues longer than the human A chain, which contains 3058 residues. Comparison of the two sequences demonstrates that the domain structure of the M chain is similar to that of the A chain, and these two laminin heavy chains have considerable homology. The overall sequence similarity is 46.6%, and 58.6% when conservative changes are included.

Expression of the M and A chain genes was compared by Northern hybridization; in situ hybridization was also conducted for the M chain in human fetal tissue. Both procedures confirmed the different tissue expression pattern of these polypeptides.

It has further been discovered that malignant tumors have an insubstantial amount of merosin compared to nonmalignant tumors. The precise amount of merosin depends on the specific tumor and can be determined by one skilled in the art given the teaching of this invention.

The following examples are intended to illustrate but not to limit the invention.

EXAMPLE I

Purification of Merosin

Screening of cDNA Library

A human placental cDNA library in lambda gtll was screened using affinity purified antibodies to the denatured 65 kD chymotrypsin fragment of merosin as described in Leivo and Engvall, supra. The identity of the isolated cDNA clones was confirmed immunologically following the procedure described by Argraves et al., J. Cell Biol. 105, 1183–1190 (1987) which is incorporated herein by reference.

Determination and Analysis of cDNA Sequences

Two cDNA clones, designated 271 and 225, with inserts of 3.6 and 1.7 kilobases, respectively, were selected for sequencing. Multiple overlapping fragments were sequenced. Nonoverlapping fragments were sequenced in both directions. Alignment of the fragments that were cloned and sequenced is summarized in FIG. 1. cDNA inserts were cleaved with various restriction enzymes, and fragments subcloned into either M13mp19(+) (Bethesda Research Laboratories, Gaithersburg, Md.) or Bluescript SK M13(+) (Stratagene Cloning Systems, La Jolla, Calif.). Nucleic acid sequencing was done by the dideoxy chain termination method of Sanger et al. using deoxyadenosine 5'-α-[$^{35}$S] thiophosphate (New England Nuclear, Boston, Mass.) and a kit from USB (Cleveland, Ohio). Some areas were sequenced using 15-base oligonucleotide primers synthesized using a DNA synthesizer (Applied Biosystems, Foster City, Calif.). Sequence analysis was done using the MicroGenie program (Beckman). Homology searches were carried out using Bionet with EMBL, Genbank, NBRF/PIR and Swiss-Prot databases.

The nucleic acid sequence of the cDNA revealed a 3.4-kilobase open reading frame followed by a 155-base-pair 3' untranslated region. The deduced amino acid sequence is shown in FIG. 1. The NH$_2$-terminal amino acid sequence of fragments isolated from peptic or chymotryptic digests of placenta and the NH$_2$-terminal amino acid sequence of a 16-kDa fragment generated with thrombin were contained within the deduced sequence, thus defining the clones as merosin cDNA.

The deduced partial sequence of merosin comprises 1130 amino acids and contains 13 potential sites of N-glycosylation. The sequence includes five repeats of about 190 amino acids. These repeats contain a conserved 7-amino acid sequence, Leu-Phe-Val-Gly-Gly-Leu-Pro, or variations thereof (FIG. 1). This is followed 17–21 and 40–43 residues later by cysteines most of which are preceded by glycines. The average percentage of identity among the five repeats is about 25%.

Protein Sequencing

A 55 kD merosin fragment was isolated from a pepsin digest of human placenta using monoclonal antibody affinity chromatography as described in Leivo and Engvall, supra. The pepsin fragment of merosin was digested further with thrombin and a 16 kD fragment was selected for sequence analysis. The merosin fragments were electrophoretically separated on a 10 to 20% gradient polyacrylamide gel in the presence of NaDodSO$_4$, blotted onto polyvinylidene difluoride membranes (Millipore, Boston, Mass.) and sequenced on an Applied Biosystems sequenator as described by Matsudaira, J. Biol. Chem. 262 10035–10038 (1987) incorporated by reference herein.

Synthetic Peptides, Antibody Production, and Immunoblotting

The length of the open reading frame of the merosin cDNA indicated that the mature merosin polypeptide was much larger than the 80 kD fragment identified originally in placental extracts. The deduced amino acid sequence suggested that the 65 kD fragment and the 80 kD tissue polypeptide are COOH-terminal fragments of merosin. The missing portion of the intact merosin polypeptide was identified after synthesizing two 13-amino acid long peptides from the part of the deduced amino acid presumed to be NH$_2$-terminal of the 80 kD fragment (residues 475–488 and 457–469 in FIG. 1). Two 13 amino acid long peptides CNNFGLDLKADDKI and CSIVDIDTNQEENI were synthesized based on amino acid sequences deduced from the cDNA sequence. The cysteine at the NH$_2$-terminus of these peptides was added to facilitate coupling to carrier protein. The peptides were coupled to keyhole limpet hemocyanin using m-maleimidobenzoyl-N-hydroxysuccinimide ester (Pierce Chemical Co., Rockford, Ill.) according to O'Sullivan et al. (Anal. Biochem 100, 100–108 (1979) incorporated by reference herein. The resulting conjugates were emulsified in Freund's complete adjuvant and injected into rabbits. Boosting immunizations of the conjugate in Freund's incomplete adjuvant were provided one and two months later. The dose of each injection was equivalent to 0.6 mg of peptide. Blood was collected 10 days after the third injection. The antisera obtained were tested against the glutaraldehyde-cross linked peptides in ELISA and against NaDodSO$_4$ extracts of tissue and isolated proteins in immunoblotting as described in Leivo and Engvall, supra.

Immunization of rabbits with these peptides resulted in antisera which, in immunoblotting, stained a polypeptide of about 300 kD in NaDodSO$_4$-extracts of placenta. This anti-peptide antisera did not react with the 80 kD or the 65 kD COOH-terminal fragments of merosin. The presence of the 80 kD fragment in the same extract was revealed by a monoclonal antibody (FIG. 3B, lane 1). Antibodies affinity purified from the anti-peptide antiserum on immobilized peptide also stained the 300 kD band. The other peptide antiserum and preimmune sera did not give any staining in immunoblotting. These results suggest that the merosin polypeptide is processed into two fragments of approximately 300 kD and 80 kD, respectively.

Isolation of Intact Merosin from Placenta

Merosin was then isolated using methods previously employed in the isolation of laminin from mouse tissues, Paulsson et al., Eur. J. Biochem, 166:11–19 (1987) incorporated by reference herein. These methods are based on the selective solubilization of laminin from basement membranes with EDTA-containing buffers. When human placenta was sequentially extracted with a neutral buffer and with the same buffer containing EDTA, merosin antigenic activity was found mainly in the EDTA extract. Merosin could be precipitated from the extract with either 4 M NaCl or 40% saturated ammonium sulphate. Upon gel filtration on Sepharose 6B, merosin antigenic activity eluted in the void volume peak. It bound to DEAE cellulose and was eluted at about 0.2 M NaCl.

FIG. 4 shows NaDodSO$_4$-polyacrylamide gel electrophoresis, electron microscopy after rotary shadowing, and ELISA analysis of the peak merosin-containing fraction from DEAE-cellulose chromatography. The predominant component in this fraction had a molecular weight of about 700 kD, slightly smaller than the 800 kD rat laminin, as determined by gel electrophoresis (FIG. 4A). After reduction with mercaptoethanol, the merosin fraction contained polypeptides of about 600 kD, 300 kD, and 180–200 kD in addition to some minor components of 60–90 kD (FIG. 4A). The synthetic peptide antiserum bound to the 500–600 kD and 300 kD bands in immunoblotting. Antibodies against the COOH-terminal fragment of merosin bound to an 80 kD band.

Electron microscopy after rotary shadowing was used to further characterize the merosin fraction. Cross-shaped images strongly resembling mouse and rat laminin were the predominant structures seen (FIG. 4B).

Analysis of the fraction by ELISA with merosin-specific and laminin subunit-specific monoclonal antibodies showed that the preparation contained the merosin polypeptide and the laminin B1 and B2 light chains. No reactivity was obtained with laminin heavy chain-specific antibodies (FIG. 4C). The truncated pepsin fragment of laminin, isolated with laminin heavy chain-specific monoclonal antibody, reacted with antibodies specific for the heavy chain as well as with antibodies specific for the B1 and B2 chains. This laminin preparation did not react with merosin antibodies (FIG. 4C). These results show that the high molecular weight, laminin-like molecule isolated from EDTA-extracts of placenta contained no detectable laminin heavy chain but contained laminin light chains associated with the merosin heavy chain.

EXAMPLE II

Merosin Activity

Merosin Promotes Cell Attachment

Cell attachment promotion by merosin was determined by methods well known in the art and set forth in Engvall and Ruoslahti, Collagen Rel. Res., 3:359–369 (1983) hereby incorporated by reference. Briefly, polystyrene microtiter plates (Flow Laboratories, Irvine, Calif.) were coated with various proteins by incubating the wells with 100 µl of different concentrations of the protein in PBS for 3–16 h at room temperature. Nonbound protein was removed by three washes in PBS. In some experiments, the wells with protein solution were air dried at 37° C. and then washed. Cells were trypsinized and washed twice with 0.5 mg/ml soy bean trypsin inhibitor in EMEM. A suspension of approximately 250,000 cells per ml EMEM with 10 mM HEPES was prepared and 0.1 ml was added to each well already containing 0.1 ml EMEM. The plate was then incubated at 37° C. for 30–90 min in an atmosphere of 10% $CO_2$ in air. Cell attachment was evaluated by one or more of the following methods: 1) Nonattached cells were removed and counted; 2) attached cells were fixed, stained with toluidine blue, and counted using an Artek cell counter (Dynatech Corporation, Alexandria, Va.); or 3) the light absorbed by the fixed and stained cells was measured using an automatic ELISA reader (Multiscan, Flow Laboratories). When laminin was tested in solution, it was serially diluted in the plate with a solution of 1 mg/ml BSA in EMEM containing 10 mM HEPES before adding the cells. All assays were done with samples in triplicates.

The cell lines in Table 1 have been tested for cell attachment to merosin. Successful attachment is indicated as a "+" The better the attachment the more "+'s."

TABLE 1

| Cell Line | Degree of Attachment | |
|---|---|---|
| | Merosin | Laminin |
| JAR, Chonocarcinoma | − | ++ |
| Endothelial Cells | − | +++ |
| SKLMS, Muscle | ++ | +++ |
| MG63, Osteosarcoma | +++ | +++ |
| U251, Glioma | +++ | +++ |
| JMR 32, Neuroblastoma | +++ | +++ |

The results show that merosin promotes attachment by many but not all types of cells.

Merosin Promotes Neurite Outgrowth

Neurite promoting activity by merosin was determined by known methods as set forth in Engvall et al., J. Cell Biol., 103:2457–2465 (1986) and Manthorpe et al., A Dissection and Tissue Culture, Manual of the Nervous System, 322–326 (1989), Alan R. Liss, Inc., both of which are hereby incorporated by reference. Briefly, embryonic day 8 chick ciliary ganglion neuronal cultures were used. Polyornithine-coated tissue culture plastic wells (6-mm diameter, 96-well microplates) were treated with 5 µg/ml of human laminin or merosin in PBS for 2–3 h at 37° C. The wells were washed once with 100 µl PBS containing 1% BSA. 100 µl culture medium (Dulbecco's modified Eagle's basal medium supplemented with 0.5% BSA, $8 \times 10^{-7}$ M insulin, $3.3 \times 10^{-2}$ M glucose, $2.6 \times 10^{-2}$ M $NaHCO_3$, $2 \times 10^{-3}$ M L-glutamine, 100 µm/ml penicillin, and 100 trophic units/ml ciliary neuronotrophic factor) containing 1,000 neurons was added. Cultures were fixed after 3 h by the addition of 200 µl 2% glutaraldehyde for 20 min., washed with water, and stained with 0.1% toluidine blue in water. About 150 neurons were observed microscopically for each culture condition. Neurons were recorded as neurite-bearing if they possessed at least 50 µm of total neurite length.

In addition, surfaces were coated with 100 µg/ml polyornithine (PORN) for attachment. 25 µg/ml laminin or merosin were then added for neurite outgrowth. Cells were allowed to extend neurites for 72 hours. The degree of promotion is set forth in table 2. Promotion of neurite growth is indicated as a "+." The greater the promotion, the more "+'s."

TABLE 2

| | No Protein | Laminin | Merosin |
|---|---|---|---|
| No Porn | − | − | − |
| Porn | + | +++ | +++ |

The results show merosin is a promotor of neurite outgrowth and, as such, is as efficient as laminin. This suggests that for certain applications (clinical) merosin would be better than laminin for nerve regeneration because it may not have e.g. angiogenic activity.

EXAMPLE III

Merosin Distribution in Human Schwann Cell Neoplasms

The expression of the basement membrane proteins merosin and laminin was studied immunohistochemically in a series of benign and malignant schwannomas and plexiform neurofibromas. Fresh tissue samples were frozen in liquid nitrogen. Monoclonal antibodies to merosin and laminin were applies to frozen sections, and indirect immunoperoxidase or indirect immunofluorescence techniques were used to detect the two proteins in tissues. The results are described in Leivo et al., Laboratory Investigation, 61:426–432 (1989). This reference and the references cited therein are hereby incorporated by reference.

Tissue Material

Human neurogenic tumors were obtained fresh without fixation at the Department of Pathology, University of Helsinki. In one instance tissue was derived from the autopsy of a patient with von Recklinghausen's disease who died of a buccal malignant schwannoma. The tissue samples were frozen in liquid nitrogen and embedded in Tissue-Tek OCT (Miles, Naperville, Ill.). The frozen sections were air-dried for 1–2 hours and fixed in acetone. Part of each tissue sample was fixed in formalin and embedded in paraffin for conventional histologic evaluation using hematoxylin-eosin.

Antibodies

Monoclonal antibodies raised to the reduced and alkylated 65-kD polypeptide fragment of merosin were used. These antibodies detect denatured human merosin, and they blotted an 80-kD polypeptide band in sodium dodecyl sulfate extracts of human placenta. The following clones of these antibodies giving identical staining results were used: 5H2, 4E10, 2G9, 4H2, 1F6, 2E10, and 2D10. Staining results identical to those obtained with monoclonal antibodies have also been obtained in normal tissues with a polyclonal antiserum to merosin. Monoclonal antibodies to nearly intact human laminin have been described, Engvall et al. supra. The monoclonal antibody 2E8 that blots the 200-kD B1 chain of laminin transferred from sodium dodecyl sulfate-polyacrylamide gels was used.

In immunohistochemical characterization of the Schwann cell tumors, we used a polyclonal rabbit antibody to bovine S-100 protein (Dakopatts, Glostrup, Denmark) at 1:300 dilution and a monoclonal antibody to glial fibrillary acidic protein (Labsystems, Helsinki, Finland) at 1:30 dilution.

Immunohistochemistry

Frozen sections were treated with hybridoma culture medial at 1:2–1:5 dilution. The primary mouse antibodies were applied on sections for 30 minutes or overnight, followed by a 30-minute incubation with biotinylated rabbit antimouse IgG anti-serum (Dako, Copenhagen, Denmark) at 1:500 dilution. Finally, the bound biotin was detected with avidin combined in vitro with biotinylated peroxidase (AB Complex, Dakopatts), both diluted at 1:160. The color was developed with 3-amino-9-ethylcarbazole (Sigma, St. Louis, Mo.) supplemented with 0.02% hydrogen peroxide. In some cases, fluorescein isothiocyanate-coupled goat antimouse IgG (Bio-Rad, Richmond, Calif.) was used to detect bound primary antibodies in indirect immunofluorescence.

For controls of specificity for the staining of merosin, normal mouse serum (1:10) or phosphate-buffered saline were used instead of the hybridoma medium. Controls of specificity for the staining of laminin by monoclonal antibodies have been documented. No significant staining was observed in control experiments. The preparations stained with the immunoperoxidase technique were lightly counterstained with Mayer's hemalum (Merck, Darmstadt, West Germany) to show nuclei. Immunoperoxidase stainings and immunofluorescence preparations were observed and photographed in a Zeiss Axiophot microscope equipped for epi-illumination.

Four human schwannomas, two plexiform neurofibromas, and four malignant schwannomas were examined. Two schwannomas were retroperitoneal; one was mediastinal, and one was from the gastric wall exhibiting the histological features of gastric schwannomas. Histologically, all schwannomas showed a relatively uniform spindle cell morphology with focally palisading arrangement of nuclei. Two cases showed an alternating pattern of cellular and loose areas, representing the so-called Antoni A and Antoni B areas, respectively. Electron microscopic examination performed in three cases disclosed spindle cells rich in rough endoplasmic reticulum exhibiting multiple slender cell processes covered by prominent deposition of basement membrane material. These findings were compatible with the ultrastructural features of schwannomas. In immunohistological studies, all schwannomas were strongly positive for S-100 protein. Glial fibrillary acidic protein (GFAP) was focally seen in three cases.

Prominent staining for laminin was seen in parallel layers of basement membranes in the cellular areas and in the entire thickness of the walls of all blood vessels. The loose, less cellular areas of the tumors and the connective tissue sheaths around vessel walls contained no immunoreactive laminin. The cellular areas including the Verocay bodies contained no or only negligible amounts of merosin. However, distinct staining for merosin was regularly seen at the interface where the cellular areas bordered the loose stromal areas or where the cellular areas bordered vascular septa.

Plexiform Neurofibromas

Two plexiform neurofibromas were from nerve trunks of the subcutis of the back and the mediastinum of patients with von Recklinghausen's disease. These tumors represented enlarged tortuous nerve trunks containing wavy collagen and spindle cells compatible with Schwann cells and fibroblasts. In both tumors, merosin and laminin were colocalized in the form of linear immunoreactivity along basement membranes outlining the tortuous nerve fascicles. Laminin was also found in vessel walls. Howeverf no merosin was seen in this location.

Malignant Schwannomas

These tumors originated from deep nerve trunks of femoral, retroperitoneal, and buccal tissues in patients with von Recklinghausen's disease. Histologically they represented malignant high grade spindle cell sarcomas with pronounced mitotic activity and focal areas of necrosis. The malignant schwannomas showed only minimal focal immunostaining for S-100 protein. No staining with antibody to GFAP was detected.

There was only minor focal staining for laminin in some perivascular tumor cells. All vessel walls were, however, strongly positive for laminin. Three of the four malignant schwannomas showed no immunostaining for merosin in the tumor cells. In contrast to laminin, only the external edges of vessel walls showed some staining. In sections where remnants of the original nerve trunks were microscopically identified, staining for merosin outlined the Schwann cell basement membranes of residual normal axons blending into merosin-negative tumor cell areas. A fibrous capsule surrounding malignant schwannomas was negative for merosin. However, in the adjacent striated muscle tissue, the basement membranes were positive for merosin. In one case, small but definite amounts of merosin were seen as punctate deposits between the tumor cells. In this case, a similar pattern of immunostaining for laminin was seen.

In brief, the distribution of merosin in schwannomas was more restricted than that of laminin, whereas in plexiform neurofibromas both proteins were present in the same location. No significant amounts of either protein were seen in malignant schwannomas.

In schwannomas, a strong staining for laminin was observed in basement membranes of the cellular Antoni A areas. In contrast, these areas were devoid of merosin. Immunoreactive merosin was seen at the border zone between tumor cells and vessel walls. The discordant distribution of the two basement membrane proteins in schwannomas differs from the situation in normal peripheral nerves where both the merosin and laminin are seen in the Schwann cell basement membranes. The reasons for this difference are unknown, but the result may reflect different biological roles for the two basement membrane proteins. Ultrastructurally, no apparent difference seems to exist between the neoplastic basement membranes of schwannomas and the normal basement membranes surrounding Schwann cells.

The presence of merosin only at the boundaries of the schwannoma cells and non-Schwann cell mesenchymal components demonstrates that the expression of merosin may be induced by a contact or an interaction of schwannoma cells with mesenchymal tissues or extracellular matrices and that no expression occurs by isolated schwannoma cells even in relatively well-differentiated tumors. Analogously, Schwann cells in peripheral nerves may require interactions with other cell types of the nerve fascicles such as the neurons, endoneurial fibroblasts, or perineurial cells for synthesis and/or deposition of merosin. It has been shown that the myelination and assembly of Schwann cell basal lamina in the developing nerve in vitro depend on interactions between the Schwann cell and neuron. Likewise, secretion of type IV collagen by cultured Schwann cells is modulated by a contact with neurons.

In plexiform neurofibromas, large amounts of both merosin and laminin were seen in an identical location. These neoplasms contain increased numbers of Schwann cells and perineurial cells as well as some residual axons contained within an intact perineurial sheath and enlarge the nerve fascicles. Thus, a relatively well-organized tissue architecture presumably essential for the expression of merosin is maintained. The presence of various cell elements within these nerve fascicles allows for many cellular contacts and interactions, and apparently some of these are essential for the secretion of merosin.

In the malignant schwannomas of this study, both merosin and laminin were absent or only minimally expressed. The concomitant lack of immunohistological markers for Schwann cell differentiation such as S-100 protein and GFAP suggests that these tumors are neurogenous sarcomas at a low level of Schwann cell differentiation.

Biosynthesis of laminin, type IV collagen, heparan sulfate proteoglycan, and entactin has been repeatedly shown in Schwann cell and schwannoma cell cultures. Moreover, in solid choriocarcinomas merosin was expressed by cells of the intermediate trophoblast type. No merosin could be detected in cultured choriocarcinoma cell lines, although these cell lines synthesized laminin. Apparently, cultured and neoplastic Schwann cells and other cells lose the capacity to secrete merosin but retain some other matrix proteins characteristic of the corresponding mature cells.

EXAMPLE IV

ISOLATION OF cDNA ENCODING FULL LENGTH HUMAN MEROSIN

Generation and Characterization of cDNA Clones cDNA libraries were made from human placental poly(A) RNA. First, RNA was primed with primer ML-1 (nucleotide residues 6917–6942, FIG. 6) made according to the M chain (merosin) sequence in FIG. 1 and Ehrig et al., *Proc. Natl. Acad. Sci. USA* 87:3264–3268 (1990), incorporated herein by reference. The cDNA was prepared with a cDNA synthesis kit according to the manufacturer's instructions (Amersham International), purified and cloned into a λgt10 vector (Promega) using EcoRI/NotI adaptors (Pharmacia) and packaged using the Packagene extract system (Promega). Two other primer extension libraries were prepared similarly using primers M-10 (nucleotide residues 4153–4167, FIG. 6) and ML-5 (nucleotide residues 1028–1050, FIG. 6). The first library was screened using the previously characterized merosin CDNA (Example I and Ehrig et al., supra, incorporated herein by reference) as probe. The 5' end 1.4 kb EcoRI fragment of clone M1-1 was used to screen the second extension library, and the third cDNA library was screened using a 1.3 kb NotI/AccI fragment of clone M10-22. To obtain clones for the 5' end of merosin, ML-6 (nucleotides 706–731, FIG. 6) primed cDNA was synthesized and EcoRI adaptors (Promega) were ligated to the cDNA. An EcoRI adapter primer and specific primers were used to amplify the 5' end of the cDNA by PCR. Purified cDNA clones and PCR products were subcloned into Bluescript II (Stratagene) and sequenced from both strands using dideoxy sequencing (Sanger et al., *Proc. Natl. Acad. Sci. USA* 84:935–939 (1977) hereby incorporated by reference).

Northern Analysis

Total RNA from 18–19 week-old human fetal tissues was isolated and samples containing 10 μg of each RNA were electrophoresed, transferred to a GeneScreen Plus filter and hybridized with human laminin A chain and merosin cDNA probes.

In situ Hybridization

To obtain sense and antisense probes for in situ hybridization a 260 bp NotI-SalI fragment from laminin A chain cDNA clone C2-12 and a 350 bp XhoI-ClaI fragment from merosin cDNA clone M1-1 were cloned into the Bluescript II vector. Probes were labeled with $^{35}$S-UTP (Amersham) using T3 and T7 polymerases. Human fetal tissues from the 17th gestational week were used. In situ hybridization was performed according to Cox et al., *Devl. Biol.* 101:485–502 (1984) and Wilkinson et al., In: *Postimplantation mammalian embryos: a Practical approach* (A.J. Copp and D.L. Cockrof, eds.) IRL Press, Oxford 155–171 (1990), each of which is hereby incorporated by reference.

Characterization of cDNA Clones and Amino Acid Sequence of the Merosin Chain

Figure 5:
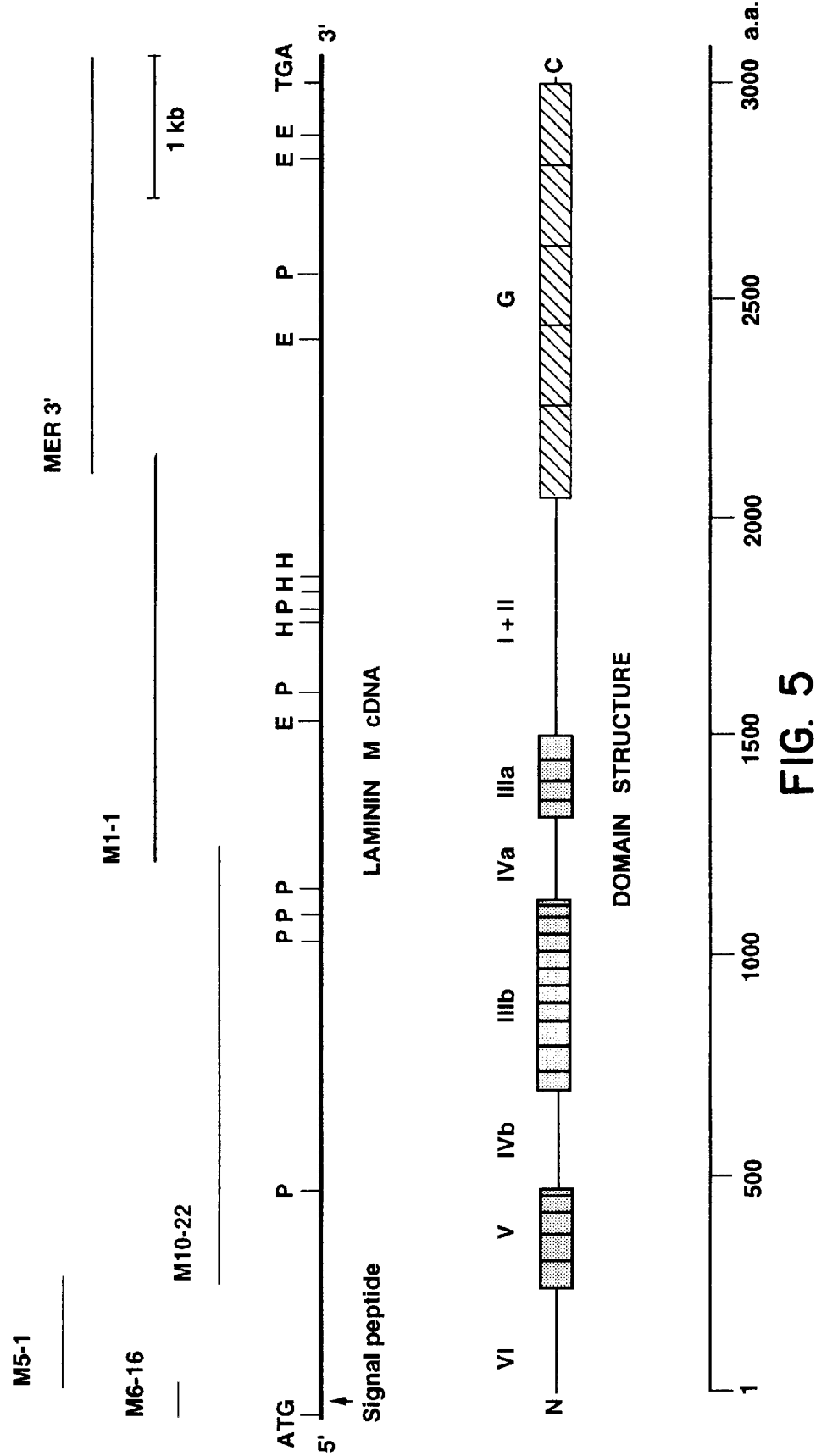
FIG. 5 shows the relative positions of the sequences of cDNA clones for human merosin polypeptide ("laminin M chain"), partial restriction maps and domain structure of the merosin subunit protein. At top, alignment of five overlapping cDNA clones and partial restriction maps of merosin cDNA. ATG indicates the translation initiation signal, and TGA the 3'-end translation stop codon. Restriction enzyme sites EcoRI (E), Hind III (H) and Pst I (P) are shown. Middle, structure of the protein with domains numbered according to Sasaki et al., Proc. Natl. Acad. Sci. USA 84:935–939 (1987); Sasaki et al., J. Biol. Chem. 263:16536–16544 (1988); Sasaki et al., J. Biol. Chem. 262:17111–17117 (1987)), incorporated herein by reference.] Five internal repeats in domain G are indicated by hatched boxes. Domains IIIa, IIIb and V consisting of cysteine-rich EGF modules are shown by shaded boxes. Bottom, scale in amino acids (aa).

A cDNA clone providing 1130 amino acid residues from the carboxyl terminal end of human merosin is described in Example 1, and by Ehrig et al., *Proc. Natl. Acad. Sci. USA* 87:3264–3268 (1990). This cDNA clone (MER 3') and its sequence were used for priming and screening of the first primer extension library. The longest positive 2.9 kb clone M1-1 (FIG. 5) was further characterized and its 5' end sequence was used to prime and screen the second primer extension library yielding clone M10-22 (3.2 kb). The 5' end of clone M10-22 was similarly used for screening of the third primer extension library resulting in the isolation of clone M5-1 (0.8 kb). Several libraries were made in order to obtain clones spanning the entire 5' end sequence. However, all clones obtained through those efforts were either of similar lengths or shorter than M5-1. Genomic clones that were characterized (data not shown) contained the putative exon 2, but not the coding region for the signal peptide and 5' untranslated region. The 5' end sequences were finally obtained by PCR amplification. The primer ML-6 was used to make cDNA to which EcoRI adaptors were ligated. An EcoRI adaptor primer and two specific primers were then used in PCR to amplify a 300 bp 5' end fragment, Mg-16 (FIG. 5), containing sequences for the 5' end untranslated region of the mRNA, the signal peptide and the amino-terminal end of merosin.

The nucleotide sequence of the overlapping cDNA clones and the deduced amino acid sequence are shown in FIG. 6. The C-terminal end amino acid sequence described in Example I and in Ehrig et al., *Proc. Natl. Acad. Sci. USA* 87:3264–3268 (1990) is included in that sequence. The clones generated and characterized in this study covered a total of 6942 bp, consisting of a 49 bp 5' end untranslated region and 6893 bp of an open reading frame. The 5' end sequence has an open reading frame but the sequence ACUACGAUGC around the initiator methionine is in agreement with the Kozak consensus sequence for translation initiation (Kozak, M., *J. Cell. Biol.* 115:887–903 (1991)

hereby incorporated by reference). The putative signal peptide contains 22 amino acids starting with the initiator methionine followed by a hydrophobic leucine-rich sequence. Computer program analysis predicting the signal peptidase cleavage site, based on the method of von Heijne (1986), incorporated here by reference, suggested a cleavage site after Ala22, whereby mature merosin would start with a glutamine residue as do most laminin chains. Altogether, merosin contains 3088 amino acid residues after cleavage of the tentative 22-residue signal peptide.

Domain Structure of Merosin Comparison with the Laminin A Chain

Mature human merosin is 30 residues larger than the human laminin A chain which contains 3058 residues (Nissinen et al., *Biochem. J.* 276:369–379 (1991); Haaparanta et al., *Matrix* 11:151–160 (1991)). The amino acid sequences of both chains are aligned in FIG. 7. Similarly to all laminin chains, the merosin protein has distinct domains which are predicted to have globular regions, cysteine-rich rod-like regions and helical structures. Additionally, merosin, like the laminin A chain, has a large globular domain at the carboxy-terminal end (Ehrig et al., *Proc. Natl. Acad. Sci. USA* 87:3264–3268 (1990)). Comparison of the two sequences demonstrates that the domain structure of merosin is similar to that of the laminin A chain, and that these two laminin heavy chains have considerable homology.

The amino-terminal end domains VI (residues 23–286), IVb (residues 528–723) and IVa (residues 1176–1379) of merosin are predicted to form globular structures. Domains V (residues 287–527), IIIb (residues 724–1175) and IIIa (residues 1380–1573) contain cysteine-rich EGF-like repeats and are predicted to have rigid rod-like structures. The number of EGF-like repeats is identical in merosin and the laimin A chain. Domain V has four and one-half repeats, domain IIIb has ten and one-half, and domain IIIa has four repeats. Beck et al., *FASEB J.* 4:148–160 (1990) and Beck et al., *In: W. Taylor and P. Argos. (eds) Springer series in biophysics*, Springer-Verlag, Berlin 7:231–256 (1992) count the half repeats as one, and according to that both chains contain 17 cysteine-rich repeats. Domains I+II (residues 1574–2153), a part of which has previously been reported (Ehrig et al., *Proc. Natl. Acad. Sci. USA* 87:3264–3268 (1990)), participate together with two B-type chains in the formation of a triple coiled-coil structure that forms the long arm of the laminin molecule. In addition, merosin contains one cysteine residue in this region which has no counterpart in the laminin A chain or any of the B-type chains characterized thus far. The large carboxy-terminal G domain (residues 2154–3110) forms the large globule at the end of the long arm of the laminin molecule.

The amino-terminal domain VI in the M chain has 12, domain IVa two, domain IIIb one, domain I+II has 10 and domain G has seven amino acid residues more than the A chain. Domain V in the A chain has two residues more than the corresponding domain in the M chain. Comparison of the amino acid sequences of the human merosin and laminin A chain shows that the overall sequence similarity is 46.6% (Table 3) and 58.6% when conservative changes are included (FIG. 7). The sequence similarity is highest in the globular domains VI, or 73.9%, although this domain in merosin contains 12 residues more at the amino-terminus than the laminin A chain. If the additional glutamine rich amino-terminal sequence is excluded, the homology is 77.4%. All six cysteine sites in this domain are conserved. The amino acid sequence identities of the cysteine-rich domains V, IIIb and IIIa between merosin and laminin A chain are 60.1%, 54.9% and 50.2%, respectively. All cysteine residues in these domains are conserved and the length of domains are about the same. The globular domains IVb and IVa of the two chains also have approximately the same number of amino acids, although the sequence similarity is lower, or 42%. The sequence similarity is lowest between domains I+II where it is only 32.3%. There is also an extra cysteine residue (residue 1970) in domain I+II in merosin that has no counterpart in the laminin A chain. The sequence identity between domains G is 41.8%. There are 28 putative N-glycosylation sites in merosin and 34 in the laminin A chain, ten of these sites are conserved between the two chains. Most putative glycosylation sites are in domains G and I+II.

Chromosomal Assignment of Human Merosin Gene

Figure 8:
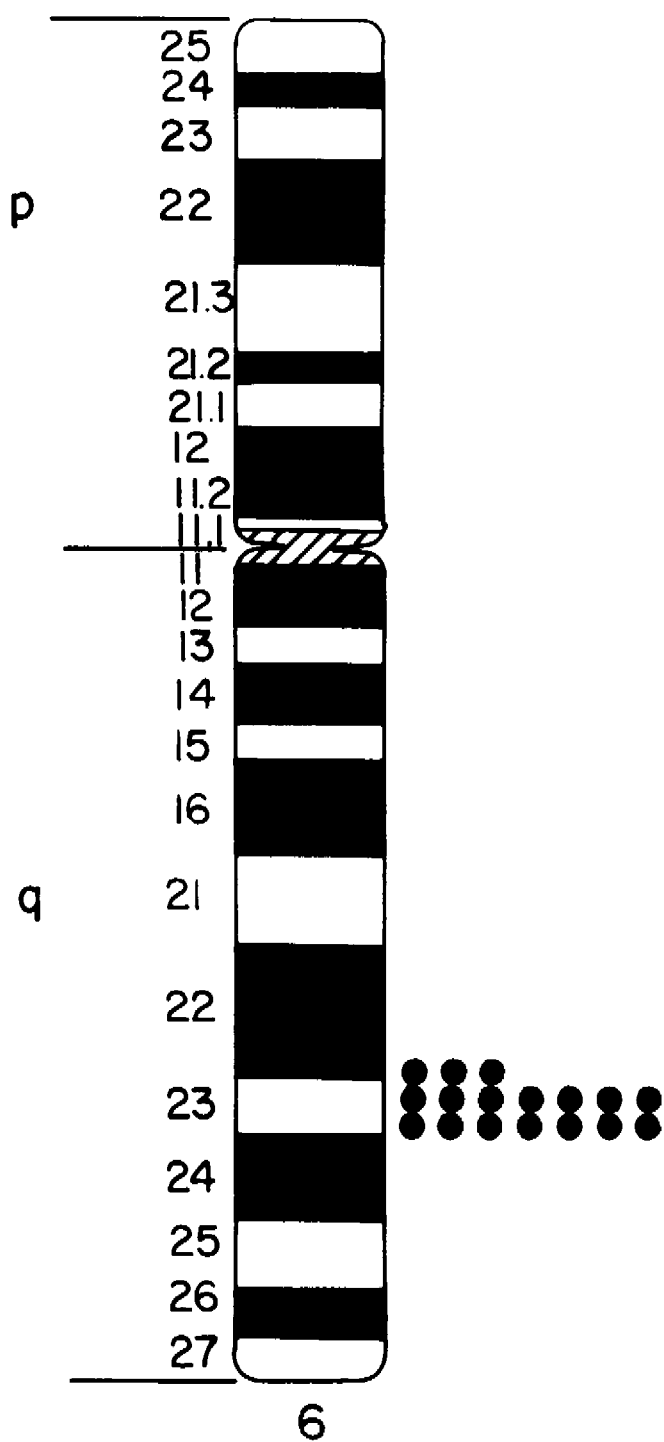
FIG. 8 shows the chromosomal localization of the merosin encoding sequences. The idiogram of chromosome 6 shows the distribution of signals on that chromosome and assignment of the merosin gene to 6q22->23.

The human merosin gene was mapped to chromosome 6 by hybridization of labeled cDNA clone M10-22 to DNA from a panel of 39 somatic cell hybrids. Hybridization of the merosin cDNA clone correlated with the distribution of chromosome 6. In situ hybridization of the cDNA to metaphase chromosomes confirmed the localization of the merosin gene to chromosome 6, and more precisely to bands 6q22–>q23 (FIG. 8).

Expression of Merosin and Laminin A Chain Genes in Human Tissues

Figure 9A:
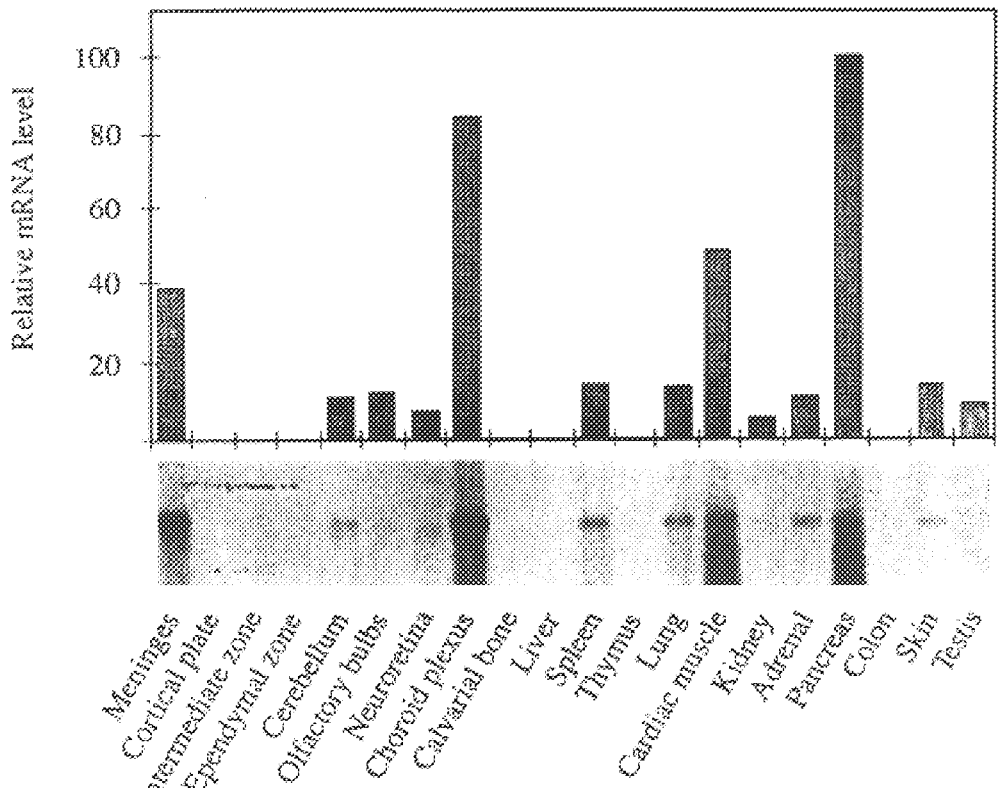
FIG. 9 shows expression of merosin and laminin A chain mRNA in 17-week-old human fetal tissues. Gene Screen Plus filter containing total RNA (–10 μg) was prepared and hybridized as described Example V below. Ethidium bromide (EtBr) staining of the filter (bottom) is shown to illustrate the relative amounts of RNA in each lane.
Figure 9B:
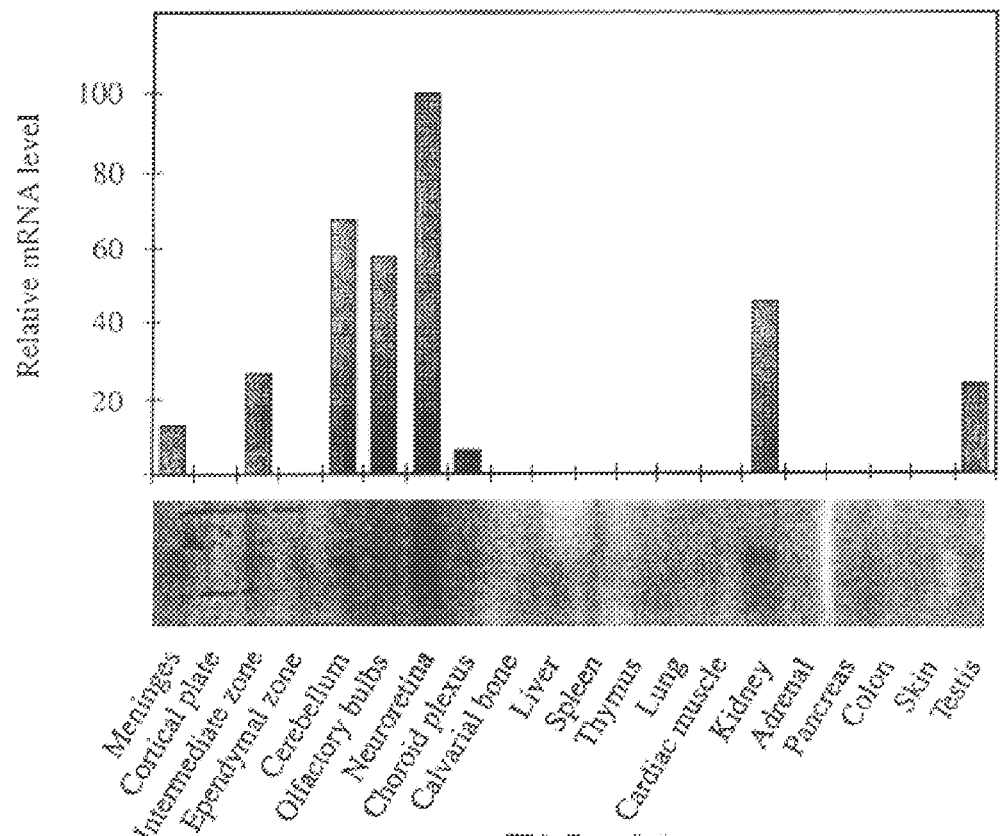

Expression of merosin and laminin A chain genes was compared by Northern hybridization using RNA from several 18–19-week-old human fetal tissues (FIG. 9). As previously reported (Nissinen et al., *Biochem. J.* 276:369–379 (1991)), the laminin A chain gene has highly restricted expression in human adult tissues. Signals for the laminin A chain were observed only in brain, neuroretina, kidney and testis, while no signals were obtained with RNA from skin, colon, pancreas, adrenal glands, cardiac muscle, lung, thymus, spleen, liver or calvarial bone, even after long exposures. The signal was by far the strongest in the neuroretina and in brain tissues the laminin A chain gene is expressed in the meninges, the intermediate zone, cerebellum, olfactory bulb and weak expression was observed also in choroid plexus and the ependymal zone.

The merosin protein has a different expression pattern, signals being observed with RNA from most tissues studied except thymus, liver, calvarial bone and ependymal and intermediate zones of brain. The strongest expression of the merosin gene was seen in cardiac muscle, pancreas, choroid plexus and meninges.

In situ Hybridization

Figure 10A:
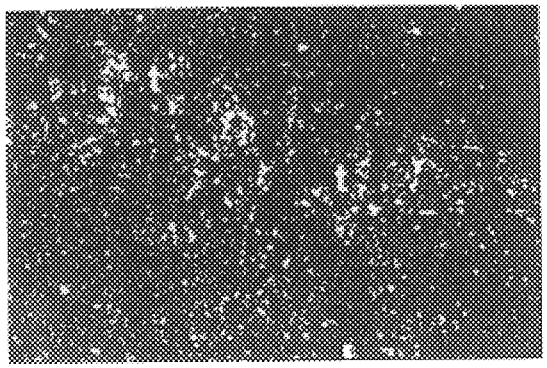
Figure 10B:
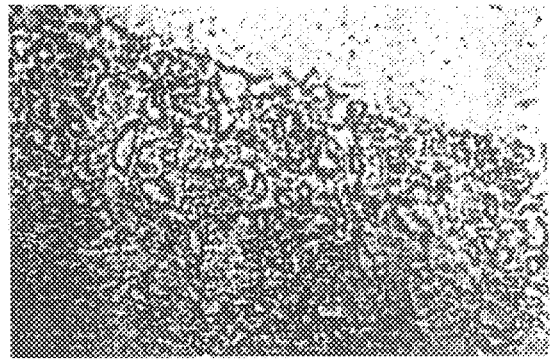
Figure 10C:
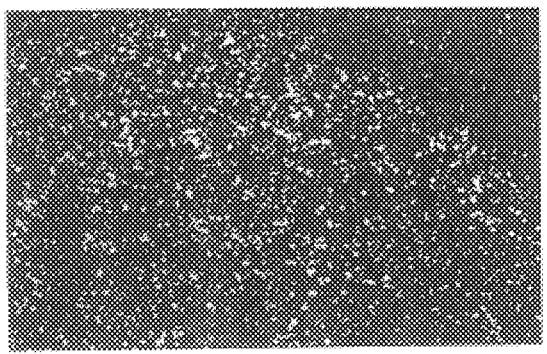
Figure 10D:
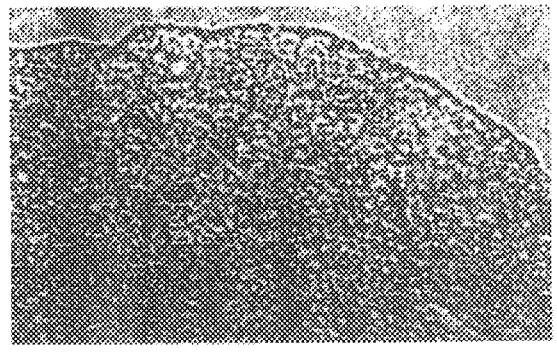
Figure 13:
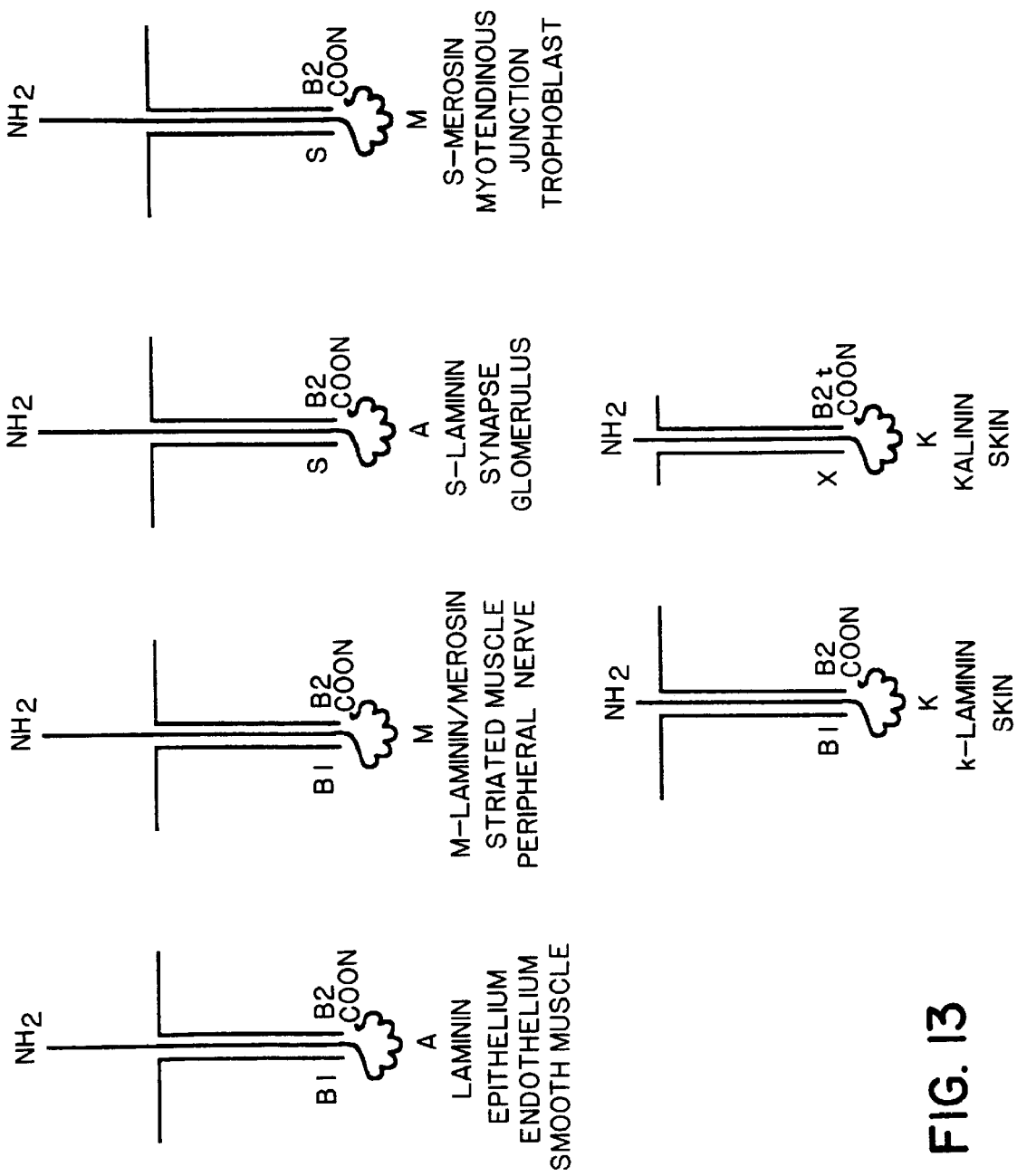
FIG. 13 is a diagramatic scheme of the structure of the laminins.

The location of merosin MRNA was analyzed by in situ hybridization in 17-week-old human fetal tissues. A cell-type-specific expression pattern for merosin mRNA was obvious in kidney, heart, skin and lung. In embryonic kidney, the transcripts for merosin were predominantly found in the undifferentiated nephrogenic mesenchyme of the outermost cortex (FIGS. 10A and 10B), whereas the nephric tubules and renal blood vessels remained negative. In heart muscle expression was observed in myocytes throughout the tissue (FIGS. 10C and 10D). The epidermal cells of the skin did not express merosin mRNA which, however, was abundant in the condensing mesenchyme around the tip of the developing hair follicles (FIGS. 10E and 10F). In the lung (FIGS. 10G and 10H) label was found in the smooth muscle cells of the pulmonary arteria, while the alveolar and bronchiolar cells were negative. Thus, the epithelial and endothelial cells were negative for merosin mRNA and the transcripts were found only in various mesenchymal cells. No cell specific signals were observed with the laminin A chain specific hybridizations in the tissues studied.

The present results, together with the 3' end sequence described in Example I and by Ehrig et al., *Proc. Natl. Acad. Sci. USA* 87:3264–3268 (1990), incorporated herein by reference, provide the complete primary structure for the human merosin. The merosin and laminin A chains were shown to be very similar. The overall sequence similarity between the two human chains (46.6%) is about the same as that between the homologous B1 and S chains. The human merosin and laminin chain genes have been localized to different chromosomes, with the exception of the genes for the closely related B2 and B2t which are located in the q25–>q31 region of chromosome 1 (Fukushima et al., *Cytogen. Cell Genet.* 48:137–141 (1988). In this study, the merosin gene was assigned to 6q22–>q23 while the related laminin A chain gene has been localized to chromosome 18p11.3 (Nagayoshi et al., *Genomics* 5:932–935 (1989)).

Domain Structure

The domain structure of merosin contains several features similar to other laminin chains and it is practically identical to that of the laminin A chain. The amino terminal globular domains VI share the highest homology, although merosin has additional 12 amino acids at the amino terminus. In fact, domain VI of all known human laminin chains, the mouse A chain, the rat S chain and the Drosophila A chain can be aligned so that the cysteine residues, some glycine, serine, proline and arginine residues, and short amino acid sequences RP, TCG and WWQS match in all chains (FIG. 11). A conserved sequence, Y(Y/F)Yxhxdhxh(G/R)G (h: hydrophobic residue, d: D, E or N) (according to Beck et al., *In: W. Taylor and P. Argos. (eds) Springer series in Biophysics*, Springer-Verlag, Berlin 7:231–256 (1992)), incorporated herein by reference, at the carboxyl terminus of domain VI also is found in merosin. The function of these conserved sequences is not known; but, while not wanting to be bound by any theory, the conserved regions can have significance for the role of this domain in laminin self-assembly which is apparently mediated by the amino terminal globular domains.

Domains V, IIIb and IIIa contain EGF-like repeats with eight cysteine residues at regular positions. The number of residues between the eighth to the second and the fifth to the seventh cysteine is the same in all laminin repeats and the order of repeats is specific. The number of repeats in merosin is 20 according to Sasaki et al., *J. Biol. Chem.* 263:16536–16544 (1988), incorporated herein by reference, or 17 according to Beck et al., *FASEB J.* 4:148–160 (1990); Beck et al., *In: W. Taylor and P. Argos, (eds) Springer series in biophysics*, Springer-Verlag, Berlin 7:231–256 (1992)), each incorporated herein by reference. The order of the repeats is conserved in human merosin and, generally, the repeats are very similar to the repeats present in human and mouse laminin A chains. The repeats in domain V of the human A, M (merosin), B1, B2 and B2t chains, the rat S chain, the murine A chain and the Drosophila A chain can be aligned in order (see FIG. 12). The human B2t chain lacks the first EGF-like repeat, but the rest of the repeats match with repeats of the other chains, except that after the second repeat there is an insertion making the distance between the eighth to the second cysteine longer than in the other chains. The alignment of domain V includes in addition to cysteine and glycine residues also other conserved sequences like HNT in first repeat between cysteines five and six. In contrast to other laminin chains, the Drosophila A chain contains 10 and a half EGF-like repeats in domain V. The two first cysteine-rich repeats in the Drosophila A chain can be aligned with repeats in the other chains but the rest of domain V differs more, although some similarities are found between repeats 3, 4, 5 and 6 in the Drosophila A chain and repeats 3, 4 and 5 in the other chains. All EGF-like repeats of known A-type chains can be aligned but this alignment is based mainly on conserved cysteines and glycines and the number of residues between them.

Globular domains IV of the A- and B2-type chains have been suggested to have evolved by an insertion between the third and fourth cysteines in one EGF-like repeat, and to be duplicated in A chains to form domains IVb and IVa. These domains are present in merosin and are, thus, well conserved in the laminin A-type chains, except for the Drosophila laminin A chain which contains only one domain IV. It also has another domain IV" that consists of duplicated sequences that are more similar to the Drosophila B1 chain domain IV.

Domains I+II form the long arm helical region. The EHS laminin chains have been shown to contain heptad repeats and similar repeats can be found also in the human laminin A chain and merosin. Proline residues are known to interrupt helices. There are four conserved proline residues in domain I+II in the mouse laminin A chain and the human laminin A chain and merosin. The cysteine pair that is suggested to form interchain disulfide bonds is conserved in merosin.

Domain G of merosin consists of five internal repeats that contain 107 to 178 amino acid residues (Ehrig et al., *Proc. Natl. Acad. Sci. USA* 87:3264–3268 (1990)), incorporated herein by reference. These repeats share 30 to 50% homology when compared with the human or mouse laminin A chain. The Drosophila laminin A chain also has five repeats in the G domain, but there is a large spacer sequence rich in threonine residues between subdomains G3 and G4 (Kusche-Gullberg et al., *EMBO J.* 11:4519–4527 (1992)). Several proteins are known to be homologous to the G domain in the laminin A chain and merosin. For example, one domain of the HSPG (heparin sulfate proteoglycan) core protein, perlecan, has 33% homology with the domain G of the human laminin A chain and merosin. Other homologous proteins are sex hormone binding globulin (Beck et al., *In: W. Taylor and P. Argos, (eds) Springer series in biophysics*, Springer-Verlag, Berlin 7:231–256 (1992)), androgen binding protein (Joseph et al., *FASEB J.* 6:2477–2481 (1992)) and neurexins (Ushkaryov et al., *Science* 257:50–56 (1992)), each of which is hereby incorporated by reference. Also Drosophila proteins fat, slit and crumbs share similarities with domain G of merosin and laminin A chain (Patthy, L., *FEBS Lett.* 298:182–184 (1992)).

TABLE I

Similarity of amino acid sequences of the human laminin Am and A chains as aligned in FIG. 3.

| Domain | Length of aligned sequence | Matches | Matches (conservative substitutions) | Un-matches | Matches % | Length |
| --- | --- | --- | --- | --- | --- | --- |
| VI | 264 | 195 | 25 | 12 | 73.9 | (83.3) |
| V | 243 | 146 | 23 | 2 | 60.1 | (69.5) |
| IV-b | 199 | 85 | 28 | 6 | 42.7 | (56.8) |
| IIIb | 452 | 248 | 38 | 1 | 54.9 | (63.3) |
| IVa | 207 | 88 | 33 | 8 | 42.5 | (58.5) |
| IIIa | 195 | 98 | 14 | 2 | 50.2 | (57.4) |
| I + II | 591 | 191 | 79 | 32 | 32.3 | (45.7) |
| G | 987 | 413 | 136 | 67 | 41.8 | (55.6) |
| Total | 3138 | 1464 | 376 | 130 | 46.6 | (58.6) |

Expression of Merosin and Laminin A Chain in Human Fetal Tissues

Expression of the merosin gene was observed in many tissues known to contain the respective protein from immunohistological studies. However, the strong level of expression at an early embryonic stage contrasts previous immunostaining studies wherein merosin was not detected in the mouse embryo (Leivo et al., *Proc. Natl. Acad. Sci. USA* 85:1544–1548 (1988)). The reason for this discrepancy is obscure; but, while not intending to be bound by any theory, it could be due to some unknown limitation in the antibodies or the transcripts may not be efficiently translated into proteins. Merosin has been reported to appear in mouse muscle tissues first after birth (Leivo et al., *Proc. Natl. Acad. Sci. USA* 85:1544–1548 (1988)) and at adult stages also in some other tissues in several mammalian species (Sanes et al., *J. Cell Biol.* 111:1685–1699 (1990)). The data presented here on 17-week-old human fetal tissues revealed strong expression of the merosin gene in cardiac muscle, pancreas, choroid plexus and meninges, significant expression also being observed in testis, skin, adrenal glands, kidney, lung, spleen, neuroretina, olfactory bulbs and cerebellum. Practically no signals were observed in thymus, liver, bone or some brain tissues such as the intermediate and ependymal zones or cortical plates. The in situ hybridization analyses localized the expression of the merosin gene to myocytes of heart muscle, which agrees with several previous studies (Leivo et al., *Proc. Natl. Acad. Sci. USA* 85:1544–1548 (1988); Paulsson et al., *J. Biol. Chem.* 264:18726–18732 (1989); Klein et al., *Development* 110:823–837 (1990); Engvall et al., *Cell Regul.* 1:731–740 (1990); Paulsson et al., *J. Biol. Chem.* 266:17545–17551 (1991)). However, expression also was seen in stromal cells close to condensing mesenchyme in kidney and skin. Merosin has been localized by a monoclonal antibody to a narrow region located between the stromal cells and pretubular condensates in the outer cortex. A good concordance between merosin mRNA and protein expression also is seen in other embryonic tissues. The strong expression observed in mesenchymal cells located immediately beneath cells at the tip of the developing hair follicle and sebaceous glands indicates the potential role of merosin in exocrine gland development. Expression of merosin was not found in epithelial or endothelial cells of any of the tissues analyzed. Consequently, it can be concluded that during embryogenesis expression of merosin is primarily, if not only, the property of cells of mesenchyme origin.

Expression of the laminin A chain gene was shown to be considerably more restricted in human fetal tissues than that of the merosin gene. As previously reported for newborn human tissues (Nissinen et al., *Biochem. J.* 276:369–379 (1991)) Northern analysis revealed expression of the laminin A chain gene in kidney. The present studies did not locate the expression at this stage of kidney development to specific cells by in situ hybridizations. The laminin A chain has been localized in the kidney to tubular and glomerular basement membranes of adult tissues (Sanes et al., *J. Cell Biol.* 111:1685–1699 (1990)) and in polarized kidney epithelial cells (Holm et al., *Cell Differ.* 24:223–238 (1988); Klein et al., *Cell* 55:331–341 (1988); Ekblom et al., *Cell* 60:337–346 (1990). Klein et al., *Development* 110:823–837 (1990) reported the detection of laminin A chain mRNA in embryonic heart, liver, lung and intestine, and laminin containing the A chain has been isolated from skeletal and heart muscle, lung, liver, kidney and intestine (Paulsson et al., *J. Biol. Chem.* 264:18726–18732 (1989)). However, in this study on tissues from a 17-week-old human fetus, no signal for the A chain mRNA was observed in lung, heart or liver, even after long exposures. This discrepancy could be due to the differences in temporal expression during development. The intense expression of the laminin A chain gene in neuroretina, olfactory bulbs and cerebellum, is interesting and indicates its role in brain and nerve development. Detailed immunohistological and in situ hybridization analyses on developing brain tissues have been initiated to further analyze the temporal and spatial expression during brain development.

Several studies including the present study have demonstrated variability in both spatial and temporal expression of laminin subunit chains in vivo. This, in part, implicates tissue-specific functions of different laminin isoforms. With regard to merosin and the laminin A chain, Engvall et al., *Cell Reaul.* 1:731–740 (1990) and Sanes et al., *J. Cell Biol.* 111:1685–1699 (1990), each incorporated herein by reference, showed that they are often mutually exclusive in a distinct type of basement membranes, suggesting that the laminin molecules contain either an M (merosin) or an A chain as a heavy chain. The present Northern blot and in situ hybridization analyses carried out on RNA from human fetal tissues supports the different tissue distribution of the M (merosin) and A chains. In particular, the results showed that the merosin gene is expressed in several tissues during embryonic development and possibly only by mesenchymal cells. However, the results also demonstrated that some laminin producing cells and tissues, such as skin and lung epithelia as well as vascular endothelia did not express either gene, or its expression was very weak in these tissues. This suggests that there exist laminin isoforms containing some, as yet, unidentified heavy A-type chains. Such isoforms may include kalinin or K-laminin.

Although the invention has been described with reference to the presently-preferred embodiment, it should be understood that various modifications can be made without departing from the spirit of the invention. Accordingly, the invention is limited only by the following claims.

What is claimed is:

1. A biologically active polypeptide having the amino acid sequence of a 380–400 KDa polypeptide of merosin as shown in FIG. 6 (SEQ ID NO: 4).

2. A method of promoting cell attachment to a substrate, comprising contacting a cell which binds to merosin with a substrate containing a merosin fragment or a cell attachment promoting portion thereof, wherein cell attachment to the substrate is promoted.

3. A method of promoting cell attachment to a substrate, comprising contacting a cell which binds to merosin with a substrate containing a biologically active polypeptide having the amino acid sequence of the 380–400 KDa polypeptide of merosin as shown in FIG. 6 (SEQ ID NO: 4), wherein cell attachment to the substrate is promoted.

* * * * *

UNITED STATES PATENT AND TRADEMARK OFFICE
CERTIFICATE OF CORRECTION

PATENT NO.    : 5,837,496                                        Page 1 of 2
DATED         : November 17, 1998
INVENTOR(S)   : Engvall et al.

It is certified that error appears in the above-identified patent and that said Letters Patent is hereby corrected as shown below:

Column 2,
Line 31, please delete "(SEQ ID NO: 2)" and replace with -- (SEQ ID NO: 1) --.

Column 3,
Line 32, please delete "(SEQ ID NO: 4)" and replace with -- (SEQ ID NO: 5) --.

Column 4,
Lines 14-16, please delete "chain; A, human A chain; mA, mouse A chain; M, human M chain, B2, human B2 chain; dA, Drosophila A chain." and replace with -- chain (SEQ ID NO: 14); A, human A chain (SEQ ID NO: 15); mA, mouse A chain (SEQ ID NO: 16); M, human M chain (SEQ ID NO: 17); B2, human B2 chain (SEQ ID NO: 18); dA, Drosophila A chain (SEQ ID NO: 18); B2t, human B2t chain (SEQ ID NO: 20). --.
Line 50, please delete "subunit" and replace with -- subunit (SEQ ID NO: 4) --.
Line 54, please delete "FIG. 1." and replace with -- FIG. 1 (SEQ ID NO: 2). --.
Line 57, please delete "FIG. 6." and replace with -- FIG. 6 (SEQ ID NO: 4). --.

Column 7,
Line 12, after "1" please insert -- (SEQ ID NO: 1) --.
Line 12, after "6" please insert -- (SEQ ID NO: 3) --.
Line 61, please delete "FIG. 1." and replace with -- FIG. 1 (SEQ ID NO: 1). --.

Column 8,
Lines 13-14, please delete "FIG. 1." and replace with -- FIG. 1. (SEQ ID NOS: 1 and 2). --.
Line 26, please delete "LFVGGLP" and replace with -- LFVGGLP (SEQ ID NO: 21) --.
Line 40, please delete "FIG. 1." and replace with -- FIG. 1 (SEQ ID NO: 1). --.
Line 46, please delete "FIG. 6." and replace with -- FIG. 6 (SEQ ID NO: 3). --.

Column 9,
Line 18, please delete "FIG. 1." and replace with -- FIG. 1 (SEQ ID NO: 1). --.
Line 36, please delete "FIG. 1." and replace with -- FIG. 1 (SEQ ID NO: 2). --.

Column 10,
Line 10, please delete "CNNFGLDLKADDKI and CSIVDIDTNQEENI" and replace with -- CNNFGLDLKADDKI (SEQ ID NO: 22) and CSIVDIDTNQEENI (SEQ ID NO: 23) --.

Column 16,
Line 56, please delete "sequence" and replace with -- sequence (SEQ ID NO: 3) --.
Line 57, please delete "sequence" and replace with -- sequence (SEQ ID NO: 4) --.

UNITED STATES PATENT AND TRADEMARK OFFICE
CERTIFICATE OF CORRECTION

PATENT NO. : 5,837,496
DATED : November 17, 1998
INVENTOR(S) : Engvall et al.

It is certified that error appears in the above-identified patent and that said Letters Patent is hereby corrected as shown below:

Column 17,
Line 6, please delete "here by" and replace with -- herein by --.
Line 57, please delete "merosin and laminin A" and replace with -- merosin (SEQ ID NO: 4) and laminin A (SEQ ID NO: 5) --.

Column 19,
Lines 53-54, please delete "A, M (merosin), B1, B2 and B2t chains, the rat S chain, the murine chain and the Drosophila A chain" and replace with -- A (SEQ ID NO: 15); M (merosin) (SEQ ID NO: 17); B1 (SEQ ID NO: 13); B2 (SEQ ID NO: 18); and B2t (SEQ ID NO: 20) chains, the rat S chain (SEQ ID NO: 14); the murine chain (SEQ ID NO: 16); and the Drosophila A chain (SEQ ID NO: 19) --.

Signed and Sealed this

Eighth Day of April, 2003

JAMES E. ROGAN
*Director of the United States Patent and Trademark Office*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 3554 base pairs
        ( B ) TYPE: nucleic acid
        ( C ) STRANDEDNESS: single
        ( D ) TOPOLOGY: linear ( i x ) FEATURE:
    ( A ) NAME/KEY: CDS
    ( B ) LOCATION: 10..3400

( x i ) SEQUENCE DESCRIPTION: SEQ ID NO:1:

```
GAATTCGGG GTT AAG AAG TTA GCA AAT GAT GTA AAA GAA AAT GAA GAC            48
          Val Lys Lys Leu Ala Asn Asp Val Lys Glu Asn Glu Asp
          1               5                   10

CAT CTA AAT GGC TTA AAA ACC AGG ATA GAA AAT GCT GAT GCT AGA AAT          96
His Leu Asn Gly Leu Lys Thr Arg Ile Glu Asn Ala Asp Ala Arg Asn
        15              20                  25

GGG GAT CTC TTG AGA ACT TTG AAT GAC ACT TTG GGA AAG TTA TCA GCT         144
Gly Asp Leu Leu Arg Thr Leu Asn Asp Thr Leu Gly Lys Leu Ser Ala
30              35                  40                  45

ATT CCA AAT GAT ACA GCT GCT AAA CTG CAA GCT GTT AAG GAC AAA GCC         192
Ile Pro Asn Asp Thr Ala Ala Lys Leu Gln Ala Val Lys Asp Lys Ala
                50                  55                  60

AGA CAA GCC AAC GAC ACA GCT AAA GAT GTA CTG GCA CAG ATT ACA GAG         240
Arg Gln Ala Asn Asp Thr Ala Lys Asp Val Leu Ala Gln Ile Thr Glu
                65                  70                  75

CTC CAC CAG AAC CTC GAT GGC CTG AAG AAG AAT TAC AAT AAA CTA GCA         288
Leu His Gln Asn Leu Asp Gly Leu Lys Lys Asn Tyr Asn Lys Leu Ala
            80                  85                  90

GAC AGC GTC GCC AAA ACG AAT GCT GTG GTT AAA GAT CCT TCC AAG AAC         336
Asp Ser Val Ala Lys Thr Asn Ala Val Val Lys Asp Pro Ser Lys Asn
        95                  100                 105

AAA ATC ATT GCC GAT GCA GAT GCC ACT GTC AAA AAT TTA GAA CAG GAA         384
Lys Ile Ile Ala Asp Ala Asp Ala Thr Val Lys Asn Leu Glu Gln Glu
110                 115                 120                 125

GCT GAC CGG CTA ATA GAT AAA CTC AAA CCC ATC AAG GAA CTT GAG GAT         432
Ala Asp Arg Leu Ile Asp Lys Leu Lys Pro Ile Lys Glu Leu Glu Asp
                130                 135                 140

AAC CTA AAG AAA AAC ATC TCT GAG ATA AAG GAA TTG ATA AAC CAA GCT         480
Asn Leu Lys Lys Asn Ile Ser Glu Ile Lys Glu Leu Ile Asn Gln Ala
                145                 150                 155

CGG AAA CAA GCC AAT TCT ATC AAA GTA TCT GTG TCT TCA GGA GGT GAC         528
Arg Lys Gln Ala Asn Ser Ile Lys Val Ser Val Ser Ser Gly Gly Asp
                160                 165                 170

TGC ATT CGA ACA TAC AAA CCA GAA ATC AAG AAA GGA AGT TAC AAT AAT         576
Cys Ile Arg Thr Tyr Lys Pro Glu Ile Lys Lys Gly Ser Tyr Asn Asn
        175                 180                 185

ATT GTT GTC AAC GTA AAG ACA GCT GTT GCT GAT AAC CTC CTC TTT TAT         624
Ile Val Val Asn Val Lys Thr Ala Val Ala Asp Asn Leu Leu Phe Tyr
190                 195                 200                 205

CTT GGA AGT GCC AAA TTT ATT GAC TTT CTG GCT ATA GAA ATG CGT AAA         672
Leu Gly Ser Ala Lys Phe Ile Asp Phe Leu Ala Ile Glu Met Arg Lys
                210                 215                 220

GGC AAA GTC AGC TTC CTC TGG GAT GTT GGA TCT GGA GTT GGA CGT GTA         720
Gly Lys Val Ser Phe Leu Trp Asp Val Gly Ser Gly Val Gly Arg Val
                225                 230                 235

GAG TAC CCA GAT TTG ACT ATT GAT GAC TCA TAT TGG TAC CGT ATC GTA         768
Glu Tyr Pro Asp Leu Thr Ile Asp Asp Ser Tyr Trp Tyr Arg Ile Val
                240                 245                 250

GCA TCA AGA ACT GGG AGA AAT GGA ACT ATT TCT GTG AGA GCC CTG GAT         816
Ala Ser Arg Thr Gly Arg Asn Gly Thr Ile Ser Val Arg Ala Leu Asp
        255                 260                 265

GGA CCC AAA GCC AGC ATT GTG CCC AGC ACA CAC CAT TCG ACG TCT CCT         864
Gly Pro Lys Ala Ser Ile Val Pro Ser Thr His His Ser Thr Ser Pro
270                 275                 280                 285

CCA GGG TAC ACG ATT CTA GAT GTG GAT GCA AAT GCA ATG CTG TTT GTT         912
```

|     |     |     |     |     |     |     |     |     |     |     |     |     |     |     |     |
| --- | --- | --- | --- | --- | --- | --- | --- | --- | --- | --- | --- | --- | --- | --- | --- |
| Pro | Gly | Tyr | Thr | Ile | Leu | Asp | Val | Asp | Ala | Asn | Ala | Met | Leu | Phe | Val |
|     |     |     |     | 290 |     |     |     | 295 |     |     |     |     |     | 300 |     |

| GGT | GGC | CTG | ACT | GGG | AAA | TTA | AAG | AAG | GCT | GAT | GCT | GTA | CGT | GTG | ATT | 960 |
| --- | --- | --- | --- | --- | --- | --- | --- | --- | --- | --- | --- | --- | --- | --- | --- | --- |
| Gly | Gly | Leu | Thr | Gly | Lys | Leu | Lys | Lys | Ala | Asp | Ala | Val | Arg | Val | Ile |     |
|     |     |     | 305 |     |     |     |     | 310 |     |     |     |     | 315 |     |     |     |

| ACA | TTC | ACT | GGC | TGC | ATG | GGA | GAA | ACA | TAC | TTT | GAC | AAC | AAA | CCT | ATA | 1008 |
| Thr | Phe | Thr | Gly | Cys | Met | Gly | Glu | Thr | Tyr | Phe | Asp | Asn | Lys | Pro | Ile |      |
|     |     | 320 |     |     |     |     | 325 |     |     |     |     |     | 330 |     |     |      |

| GGT | TTG | TGG | AAT | TTC | CGA | GAA | AAA | GAA | GGT | GAC | TGC | AAA | GGA | TGC | ACT | 1056 |
| Gly | Leu | Trp | Asn | Phe | Arg | Glu | Lys | Glu | Gly | Asp | Cys | Lys | Gly | Cys | Thr |      |
|     | 335 |     |     |     |     |     | 340 |     |     |     |     | 345 |     |     |     |      |

| GTC | AGT | CCT | CAG | GTG | GAA | GAT | AGT | GAG | GGG | ACT | ATT | CAA | TTT | GAT | GGA | 1104 |
| Val | Ser | Pro | Gln | Val | Glu | Asp | Ser | Glu | Gly | Thr | Ile | Gln | Phe | Asp | Gly |      |
| 350 |     |     |     |     | 355 |     |     |     |     | 360 |     |     |     |     | 365 |      |

| GAA | GGT | TAT | GCA | TTG | GTC | AGC | CGT | CCC | ATT | CGC | TGG | TAC | CCC | AAC | ATC | 1152 |
| Glu | Gly | Tyr | Ala | Leu | Val | Ser | Arg | Pro | Ile | Arg | Trp | Tyr | Pro | Asn | Ile |      |
|     |     |     |     | 370 |     |     |     |     | 375 |     |     |     |     | 380 |     |      |

| TCC | ACT | GTC | ATG | TTC | AAG | TTC | AGA | ACA | TTT | TCT | TCG | AGT | GCT | CTT | CTG | 1200 |
| Ser | Thr | Val | Met | Phe | Lys | Phe | Arg | Thr | Phe | Ser | Ser | Ser | Ala | Leu | Leu |      |
|     |     |     | 385 |     |     |     |     | 390 |     |     |     |     | 395 |     |     |      |

| ATG | TAT | CTT | GCC | ACA | CGA | GAC | CTG | AGA | GAT | TTC | ATG | AGT | GTG | GAG | CTC | 1248 |
| Met | Tyr | Leu | Ala | Thr | Arg | Asp | Leu | Arg | Asp | Phe | Met | Ser | Val | Glu | Leu |      |
|     |     |     | 400 |     |     |     |     | 405 |     |     |     |     | 410 |     |     |      |

| ACT | GAT | GGG | CAC | ATA | AAA | GTC | AGT | TAC | GAT | CTG | GGC | TCA | GGA | ATG | GCT | 1296 |
| Thr | Asp | Gly | His | Ile | Lys | Val | Ser | Tyr | Asp | Leu | Gly | Ser | Gly | Met | Ala |      |
|     |     | 415 |     |     |     |     | 420 |     |     |     |     | 425 |     |     |     |      |

| TCC | GTT | GTC | AGC | AAT | CAA | AAC | CAT | AAT | GAT | GGG | AAA | TGG | AAA | TCA | TTC | 1344 |
| Ser | Val | Val | Ser | Asn | Gln | Asn | His | Asn | Asp | Gly | Lys | Trp | Lys | Ser | Phe |      |
| 430 |     |     |     |     | 435 |     |     |     |     | 440 |     |     |     |     | 445 |      |

| ACT | CTG | TCA | AGA | ATT | CAA | AAA | CAA | GCC | AAT | ATA | TCA | ATT | GTA | GAT | ATA | 1392 |
| Thr | Leu | Ser | Arg | Ile | Gln | Lys | Gln | Ala | Asn | Ile | Ser | Ile | Val | Asp | Ile |      |
|     |     |     |     | 450 |     |     |     |     | 455 |     |     |     |     | 460 |     |      |

| GAT | ACT | AAT | CAG | GAG | GAG | AAT | ATA | GCA | ACT | TCG | TCT | TCT | GGA | AAC | AAC | 1440 |
| Asp | Thr | Asn | Gln | Glu | Glu | Asn | Ile | Ala | Thr | Ser | Ser | Ser | Gly | Asn | Asn |      |
|     |     |     | 465 |     |     |     |     | 470 |     |     |     |     | 475 |     |     |      |

| TTT | GGT | CTT | GAC | TTG | AAA | GCA | GAT | GAC | AAA | ATA | TAT | TTT | GGT | GGC | CTG | 1488 |
| Phe | Gly | Leu | Asp | Leu | Lys | Ala | Asp | Asp | Lys | Ile | Tyr | Phe | Gly | Gly | Leu |      |
|     |     |     | 480 |     |     |     |     | 485 |     |     |     |     | 490 |     |     |      |

| CCA | ACG | CTG | AGA | AAC | TTG | AGT | ATG | AAA | GCA | AGG | CCA | GAA | GTA | AAT | CTG | 1536 |
| Pro | Thr | Leu | Arg | Asn | Leu | Ser | Met | Lys | Ala | Arg | Pro | Glu | Val | Asn | Leu |      |
|     |     |     | 495 |     |     |     |     | 500 |     |     |     |     | 505 |     |     |      |

| AAG | AAA | TAT | TCC | GGC | TGC | CTC | AAA | GAT | ATT | GAA | ATT | TCA | AGA | ACT | CCG | 1584 |
| Lys | Lys | Tyr | Ser | Gly | Cys | Leu | Lys | Asp | Ile | Glu | Ile | Ser | Arg | Thr | Pro |      |
| 510 |     |     |     |     | 515 |     |     |     |     | 520 |     |     |     |     | 525 |      |

| TAC | AAT | ATA | CTC | AGT | AGT | CCC | GAT | TAT | GTT | GGT | GTT | ACC | AAA | GGA | TGT | 1632 |
| Tyr | Asn | Ile | Leu | Ser | Ser | Pro | Asp | Tyr | Val | Gly | Val | Thr | Lys | Gly | Cys |      |
|     |     |     |     | 530 |     |     |     |     | 535 |     |     |     |     | 540 |     |      |

| TCC | CTG | GAG | AAT | GTT | TAC | ACA | GTT | AGC | TTT | CCT | AAG | CCT | GGT | TTT | GTG | 1680 |
| Ser | Leu | Glu | Asn | Val | Tyr | Thr | Val | Ser | Phe | Pro | Lys | Pro | Gly | Phe | Val |      |
|     |     |     | 545 |     |     |     |     | 550 |     |     |     |     | 555 |     |     |      |

| GAG | CTC | TCC | CCT | GTG | CCA | ATT | GAT | GTA | GGA | ACA | GAA | ATC | AAC | CTG | TCA | 1728 |
| Glu | Leu | Ser | Pro | Val | Pro | Ile | Asp | Val | Gly | Thr | Glu | Ile | Asn | Leu | Ser |      |
|     |     | 560 |     |     |     |     | 565 |     |     |     |     | 570 |     |     |     |      |

| TTC | AGC | ACC | AAG | AAT | GAG | TCC | GGC | ATC | ATT | CTT | TTG | GGA | AGT | GGA | GGG | 1776 |
| Phe | Ser | Thr | Lys | Asn | Glu | Ser | Gly | Ile | Ile | Leu | Leu | Gly | Ser | Gly | Gly |      |
| 575 |     |     |     |     | 580 |     |     |     |     | 585 |     |     |     |     |     |      |

| ACA | CCA | GCA | CCA | CCT | AGG | AGA | AAA | CGA | AGG | CAG | ACT | GGA | CAG | GCC | TAT | 1824 |
| Thr | Pro | Ala | Pro | Pro | Arg | Arg | Lys | Arg | Arg | Gln | Thr | Gly | Gln | Ala | Tyr |      |
| 590 |     |     |     |     | 595 |     |     |     |     | 600 |     |     |     |     | 605 |      |

| TAT | GTA | ATA | CTC | CTC | AAC | AGG | GGC | CGT | CTG | GAA | GTG | CAT | CTC | TCC | ACA | 1872 |

| | | | | | | | | | | | | | | | |
|---|---|---|---|---|---|---|---|---|---|---|---|---|---|---|---|
| Tyr | Val | Ile | Leu | Leu | Asn | Arg | Gly | Arg | Leu | Glu | Val | His | Leu | Ser | Thr |
| | | | | 610 | | | | 615 | | | | | | 620 | |

| | | | | | | | | | | | | | | | | |
|---|---|---|---|---|---|---|---|---|---|---|---|---|---|---|---|---|
| GGG | GCA | CGA | ACA | ATG | AGG | AAA | ATT | GTC | ATC | AGA | CCA | GAG | CCG | AAT | CTG | 1920 |
| Gly | Ala | Arg | Thr | Met | Arg | Lys | Ile | Val | Ile | Arg | Pro | Glu | Pro | Asn | Leu | |
| | | | 625 | | | | | 630 | | | | | 635 | | | |
| TTT | CAT | GAT | GGA | AGA | GAA | CAT | TCC | GTT | CAT | GTA | GAG | CGA | ACT | AGA | GGC | 1968 |
| Phe | His | Asp | Gly | Arg | Glu | His | Ser | Val | His | Val | Glu | Arg | Thr | Arg | Gly | |
| | | 640 | | | | | 645 | | | | | 650 | | | | |
| ATC | TTT | ACA | GTT | CAA | GTG | GAT | GAA | AAC | AGA | AGA | TAC | ATG | CAA | AAC | CTG | 2016 |
| Ile | Phe | Thr | Val | Gln | Val | Asp | Glu | Asn | Arg | Arg | Tyr | Met | Gln | Asn | Leu | |
| | 655 | | | | | 660 | | | | | 665 | | | | | |
| ACA | GTT | GAA | CAG | CCT | ATC | GAA | GTT | AAA | AAG | CTT | TTC | GTT | GGG | GGT | GCT | 2064 |
| Thr | Val | Glu | Gln | Pro | Ile | Glu | Val | Lys | Lys | Leu | Phe | Val | Gly | Gly | Ala | |
| 670 | | | | | 675 | | | | | 680 | | | | | 685 | |
| CCA | CCT | GAA | TTT | CAA | CCT | TCC | CCA | CTC | AGA | AAT | ATT | CCT | CCT | TTT | GAA | 2112 |
| Pro | Pro | Glu | Phe | Gln | Pro | Ser | Pro | Leu | Arg | Asn | Ile | Pro | Pro | Phe | Glu | |
| | | | | 690 | | | | | 695 | | | | | 700 | | |
| GGC | TGC | ATA | TGG | AAT | CTT | GTT | ATT | AAC | TCT | GTC | CCC | ATG | GAC | TTT | GCA | 2160 |
| Gly | Cys | Ile | Trp | Asn | Leu | Val | Ile | Asn | Ser | Val | Pro | Met | Asp | Phe | Ala | |
| | | | 705 | | | | | 710 | | | | | 715 | | | |
| AGG | CCT | GTG | TCC | TTC | AAA | AAT | GCT | GAC | ATT | GGT | CGC | TGT | GCC | CAT | CAG | 2208 |
| Arg | Pro | Val | Ser | Phe | Lys | Asn | Ala | Asp | Ile | Gly | Arg | Cys | Ala | His | Gln | |
| | | | 720 | | | | 725 | | | | | 730 | | | | |
| AAA | CTC | CGT | GAA | GAT | GAA | GAT | GGA | GCA | GCT | CCA | GCT | GAA | ATA | GTT | ATC | 2256 |
| Lys | Leu | Arg | Glu | Asp | Glu | Asp | Gly | Ala | Ala | Pro | Ala | Glu | Ile | Val | Ile | |
| | 735 | | | | | 740 | | | | | 745 | | | | | |
| CAG | CCT | GAG | CCA | GTT | CCC | ACC | CCA | GCC | TTT | CCT | ACG | CCC | ACC | CCA | GTT | 2304 |
| Gln | Pro | Glu | Pro | Val | Pro | Thr | Pro | Ala | Phe | Pro | Thr | Pro | Thr | Pro | Val | |
| 750 | | | | | 755 | | | | | 760 | | | | | 765 | |
| CTG | ACA | CAT | GGT | CCT | TGT | GCT | GCA | GAA | TCA | GAA | CCA | GCT | CTT | TTG | ATA | 2352 |
| Leu | Thr | His | Gly | Pro | Cys | Ala | Ala | Glu | Ser | Glu | Pro | Ala | Leu | Leu | Ile | |
| | | | | 770 | | | | | 775 | | | | | 780 | | |
| GGG | AGC | AAG | CAG | TTC | GGG | CTT | TCA | AGA | AAC | AGT | CAC | ATT | GCA | ATT | GCA | 2400 |
| Gly | Ser | Lys | Gln | Phe | Gly | Leu | Ser | Arg | Asn | Ser | His | Ile | Ala | Ile | Ala | |
| | | | 785 | | | | | 790 | | | | | 795 | | | |
| TTT | GAT | GAC | ACC | AAA | GTT | AAA | AAC | CGT | CTC | ACA | ATT | GAG | TTG | GAA | GTA | 2448 |
| Phe | Asp | Asp | Thr | Lys | Val | Lys | Asn | Arg | Leu | Thr | Ile | Glu | Leu | Glu | Val | |
| | | 800 | | | | | 805 | | | | | 810 | | | | |
| AGA | ACC | GAA | GCT | GAA | TCC | GGC | TTG | CTT | TTT | TAC | ATG | GCT | GCG | ATC | AAT | 2496 |
| Arg | Thr | Glu | Ala | Glu | Ser | Gly | Leu | Leu | Phe | Tyr | Met | Ala | Ala | Ile | Asn | |
| | 815 | | | | | 820 | | | | | 825 | | | | | |
| CAT | GCT | GAT | TTT | GCA | ACA | GTT | CAG | CTG | AGA | AAT | GGA | TTG | CCC | TAC | TTC | 2544 |
| His | Ala | Asp | Phe | Ala | Thr | Val | Gln | Leu | Arg | Asn | Gly | Leu | Pro | Tyr | Phe | |
| 830 | | | | | 835 | | | | | 840 | | | | | 845 | |
| AGC | TAT | GAC | TTG | GGG | AGT | GGG | GAC | ACC | CAC | ACC | ATG | ATC | CCC | ACC | AAA | 2592 |
| Ser | Tyr | Asp | Leu | Gly | Ser | Gly | Asp | Thr | His | Thr | Met | Ile | Pro | Thr | Lys | |
| | | | | 850 | | | | | 855 | | | | | 860 | | |
| ATC | AAT | GAT | GGC | CAG | TGG | CAC | AAG | ATT | AAG | ATA | ATG | AGA | AGT | AAG | CAA | 2640 |
| Ile | Asn | Asp | Gly | Gln | Trp | His | Lys | Ile | Lys | Ile | Met | Arg | Ser | Lys | Gln | |
| | | | 865 | | | | | 870 | | | | | 875 | | | |
| GAA | GGA | ATT | CTT | TAT | GTA | GAT | GGG | GCT | TCC | AAC | AGA | ACC | ATC | AGT | CCC | 2688 |
| Glu | Gly | Ile | Leu | Tyr | Val | Asp | Gly | Ala | Ser | Asn | Arg | Thr | Ile | Ser | Pro | |
| | | 880 | | | | | 885 | | | | | 890 | | | | |
| AAA | AAA | GCC | GAC | ATC | CTG | GAT | GTC | GTG | GGA | ATG | CTG | TAT | GTT | GGT | GGG | 2736 |
| Lys | Lys | Ala | Asp | Ile | Leu | Asp | Val | Val | Gly | Met | Leu | Tyr | Val | Gly | Gly | |
| | 895 | | | | | 900 | | | | | 905 | | | | | |
| TTA | CCC | ATC | AAC | TAC | ACT | ACC | CGA | AGA | ATT | GGT | CCA | GTG | ACC | TAT | AGC | 2784 |
| Leu | Pro | Ile | Asn | Tyr | Thr | Thr | Arg | Arg | Ile | Gly | Pro | Val | Thr | Tyr | Ser | |
| 910 | | | | | 915 | | | | | 920 | | | | | 925 | |
| ATT | GAT | GGC | TGC | GTC | AGG | AAT | CTC | CAC | ATG | GCA | GAG | GCC | CCT | GCC | GAT | 2832 |

| | | | | | | | | | | | | | | | | |
|---|---|---|---|---|---|---|---|---|---|---|---|---|---|---|---|---|
| Ile | Asp | Gly | Cys | Val<br>930 | Arg | Asn | Leu | His<br>935 | Met | Ala | Glu | Ala | Pro<br>940 | Ala | Asp | |
| CTG | GAA | CAA | CCC | ACC | TCC | AGC | TTC | CAT | GTT | GGG | ACA | TGT | TTT | GCA | AAT | 2880 |
| Leu | Glu | Gln | Pro<br>945 | Thr | Ser | Ser | Phe | His<br>950 | Val | Gly | Thr | Cys | Phe<br>955 | Ala | Asn | |
| GCT | CAG | AGG | GGA | ACA | TAT | TTT | GAC | GGA | ACC | GGT | TTT | GCC | AAA | GCA | GTT | 2928 |
| Ala | Gln | Arg<br>960 | Gly | Thr | Tyr | Phe | Asp<br>965 | Gly | Thr | Gly | Phe | Ala<br>970 | Lys | Ala | Val | |
| GGT | GGA | TTC | AAA | GTG | GGA | TTG | GAC | CTT | CTT | GTA | GAA | TTT | GAA | TTC | GCG | 2976 |
| Gly | Gly<br>975 | Phe | Lys | Val | Gly | Leu<br>980 | Asp | Leu | Leu | Val | Glu<br>985 | Phe | Glu | Phe | Ala | |
| ACA | ACT | ACA | ACG | ACT | GGA | GTT | CTT | CTG | GGG | ATC | AGT | AGT | CAA | AAA | ATG | 3024 |
| Thr<br>990 | Thr | Thr | Thr | Thr | Gly<br>995 | Val | Leu | Leu | Gly | Ile<br>1000 | Ser | Ser | Gln | Lys | Met<br>1005 | |
| GAT | GGA | ATG | GGT | ATT | GAA | ATG | ATT | GAT | GAA | AAG | TTG | ATG | TTT | CAT | GTG | 3072 |
| Asp | Gly | Met | Gly | Ile<br>1010 | Glu | Met | Ile | Asp | Glu<br>1015 | Lys | Leu | Met | Phe | His<br>1020 | Val | |
| GAC | AAT | GGT | GCG | GGC | AGA | TTC | ACT | GCT | GTC | TAT | GAT | GCT | GGG | GTT | CCA | 3120 |
| Asp | Asn | Gly | Ala<br>1025 | Gly | Arg | Phe | Thr | Ala<br>1030 | Val | Tyr | Asp | Ala | Gly<br>1035 | Val | Pro | |
| GGG | CAT | TTG | TGT | GAT | GGA | CAA | TGG | CAT | AAA | GTC | ACT | GCC | AAC | AAG | ATC | 3168 |
| Gly | His | Leu<br>1040 | Cys | Asp | Gly | Gln | Trp | His<br>1045 | Lys | Val | Thr | Ala<br>1050 | Asn | Lys | Ile | |
| AAA | CAC | CGC | ATT | GAG | CTC | ACA | GTC | GAT | GGG | AAC | CAG | GTG | GAA | GCC | CAA | 3216 |
| Lys | His | Arg<br>1055 | Ile | Glu | Leu | Thr<br>1060 | Val | Asp | Gly | Asn | Gln<br>1065 | Val | Glu | Ala | Gln | |
| AGC | CCA | AAC | CCA | GCA | TCT | ACA | TCA | GCT | GAC | ACA | AAT | GAC | CCT | GTG | TTT | 3264 |
| Ser<br>1070 | Pro | Asn | Pro | Ala | Ser<br>1075 | Thr | Ser | Ala | Asp | Thr<br>1080 | Asn | Asp | Pro | Val | Phe<br>1085 | |
| GTT | GGA | GGC | TTC | CCA | GAT | GAC | CTC | AAG | CAG | TTT | GGC | CTA | ACA | ACC | AGT | 3312 |
| Val | Gly | Gly | Phe | Pro<br>1090 | Asp | Asp | Leu | Lys | Gln<br>1095 | Phe | Gly | Leu | Thr | Thr<br>1100 | Ser | |
| ATT | CCG | TTC | CGA | GGT | TGC | ATC | AGA | TCC | CTG | AAG | CTC | ACC | AAA | GGC | ACA | 3360 |
| Ile | Pro | Phe | Arg | Gly<br>1105 | Cys | Ile | Arg | Ser | Leu<br>1110 | Lys | Leu | Thr | Lys | Gly<br>1115 | Thr | |
| GCA | AGC | CAC | TGG | AGG | TTA | ATT | TTG | CCA | AGG | CCC | TGG | AAC | T | GAGGGGCGTT | | 3410 |
| Ala | Ser | His<br>1120 | Trp | Arg | Leu | Ile | Leu | Pro<br>1125 | Arg | Pro | Trp | Asn<br>113 | | | | |

| | | | |
|---|---|---|---|
| CAACCTGTAT CATGCCCAGC CAACTAATAA AAATAAGTGT AACCCCAGGA AGAGTCTGTC | | | 3470 |
| AAAACAAGTA TATCAAGTAA AACAAACAAA TATATTTTAC CTATATATGT TAATTAAACT | | | 3530 |
| AATTTGTGCA TGTACATAGA ATTC | | | 3554 |

( 2 ) INFORMATION FOR SEQ ID NO:2:

( i ) SEQUENCE CHARACTERISTICS:
        ( A ) LENGTH: 1130 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Val<br>1 | Lys | Lys | Leu | Ala<br>5 | Asn | Asp | Val | Lys<br>10 | Glu | Asn | Glu | Asp | His<br>15 | Leu | Asn |
| Gly | Leu | Lys | Thr<br>20 | Arg | Ile | Glu | Asn | Ala<br>25 | Asp | Ala | Arg | Asn | Gly<br>30 | Asp | Leu |
| Leu | Arg | Thr<br>35 | Leu | Asn | Asp | Thr | Leu<br>40 | Gly | Lys | Leu | Ser | Ala<br>45 | Ile | Pro | Asn |
| Asp | Thr<br>50 | Ala | Ala | Lys | Leu | Gln<br>55 | Ala | Val | Lys | Asp | Lys<br>60 | Ala | Arg | Gln | Ala |

```
Asn  Asp  Thr  Ala  Lys  Asp  Val  Leu  Ala  Gln  Ile  Thr  Glu  Leu  His  Gln
 65                  70                       75                            80

Asn  Leu  Asp  Gly  Leu  Lys  Lys  Asn  Tyr  Asn  Lys  Leu  Ala  Asp  Ser  Val
                    85                       90                       95

Ala  Lys  Thr  Asn  Ala  Val  Val  Lys  Asp  Pro  Ser  Lys  Asn  Lys  Ile  Ile
               100                 105                      110

Ala  Asp  Ala  Asp  Ala  Thr  Val  Lys  Asn  Leu  Glu  Gln  Glu  Ala  Asp  Arg
          115                      120                      125

Leu  Ile  Asp  Lys  Leu  Lys  Pro  Ile  Lys  Glu  Leu  Glu  Asp  Asn  Leu  Lys
     130                      135                 140

Lys  Asn  Ile  Ser  Glu  Ile  Lys  Glu  Leu  Ile  Asn  Gln  Ala  Arg  Lys  Gln
145                      150                 155                           160

Ala  Asn  Ser  Ile  Lys  Val  Ser  Val  Ser  Ser  Gly  Gly  Asp  Cys  Ile  Arg
               165                      170                           175

Thr  Tyr  Lys  Pro  Glu  Ile  Lys  Lys  Gly  Ser  Tyr  Asn  Asn  Ile  Val  Val
               180                      185                      190

Asn  Val  Lys  Thr  Ala  Val  Ala  Asp  Asn  Leu  Leu  Phe  Tyr  Leu  Gly  Ser
          195                      200                      205

Ala  Lys  Phe  Ile  Asp  Phe  Leu  Ala  Ile  Glu  Met  Arg  Lys  Gly  Lys  Val
     210                      215                      220

Ser  Phe  Leu  Trp  Asp  Val  Gly  Ser  Gly  Val  Gly  Arg  Val  Glu  Tyr  Pro
225                      230                      235                      240

Asp  Leu  Thr  Ile  Asp  Asp  Ser  Tyr  Trp  Tyr  Arg  Ile  Val  Ala  Ser  Arg
               245                      250                           255

Thr  Gly  Arg  Asn  Gly  Thr  Ile  Ser  Val  Arg  Ala  Leu  Asp  Gly  Pro  Lys
               260                      265                      270

Ala  Ser  Ile  Val  Pro  Ser  Thr  His  His  Ser  Thr  Ser  Pro  Pro  Gly  Tyr
          275                      280                      285

Thr  Ile  Leu  Asp  Val  Asp  Ala  Asn  Ala  Met  Leu  Phe  Val  Gly  Gly  Leu
     290                      295                      300

Thr  Gly  Lys  Leu  Lys  Lys  Ala  Asp  Ala  Val  Arg  Val  Ile  Thr  Phe  Thr
305                      310                      315                      320

Gly  Cys  Met  Gly  Glu  Thr  Tyr  Phe  Asp  Asn  Lys  Pro  Ile  Gly  Leu  Trp
                    325                      330                      335

Asn  Phe  Arg  Glu  Lys  Glu  Gly  Asp  Cys  Lys  Gly  Cys  Thr  Val  Ser  Pro
          340                      345                      350

Gln  Val  Glu  Asp  Ser  Glu  Gly  Thr  Ile  Gln  Phe  Asp  Gly  Glu  Gly  Tyr
          355                      360                      365

Ala  Leu  Val  Ser  Arg  Pro  Ile  Arg  Trp  Tyr  Pro  Asn  Ile  Ser  Thr  Val
     370                      375                      380

Met  Phe  Lys  Phe  Arg  Thr  Phe  Ser  Ser  Ser  Ala  Leu  Leu  Met  Tyr  Leu
385                      390                      395                      400

Ala  Thr  Arg  Asp  Leu  Arg  Asp  Phe  Met  Ser  Val  Glu  Leu  Thr  Asp  Gly
                    405                      410                      415

His  Ile  Lys  Val  Ser  Tyr  Asp  Leu  Gly  Ser  Gly  Met  Ala  Ser  Val  Val
               420                      425                      430

Ser  Asn  Gln  Asn  His  Asn  Asp  Gly  Lys  Trp  Lys  Ser  Phe  Thr  Leu  Ser
          435                      440                      445

Arg  Ile  Gln  Lys  Gln  Ala  Asn  Ile  Ser  Ile  Val  Asp  Ile  Asp  Thr  Asn
     450                      455                      460

Gln  Glu  Glu  Asn  Ile  Ala  Thr  Ser  Ser  Ser  Gly  Asn  Asn  Phe  Gly  Leu
465                      470                      475                      480

Asp  Leu  Lys  Ala  Asp  Asp  Lys  Ile  Tyr  Phe  Gly  Gly  Leu  Pro  Thr  Leu
```

-continued

|  | 485 |  |  |  |  |  | 490 |  |  |  |  |  | 495 |  |
|---|---|---|---|---|---|---|---|---|---|---|---|---|---|---|

Arg Asn Leu Ser Met Lys Ala Arg Pro Glu Val Asn Leu Lys Tyr
500                          505                          510

Ser Gly Cys Leu Lys Asp Ile Glu Ile Ser Arg Thr Pro Tyr Asn Ile
         515                          520                     525

Leu Ser Ser Pro Asp Tyr Val Gly Val Thr Lys Gly Cys Ser Leu Glu
530                          535                     540

Asn Val Tyr Thr Val Ser Phe Pro Lys Pro Gly Phe Val Glu Leu Ser
545                     550                     555                     560

Pro Val Pro Ile Asp Val Gly Thr Glu Ile Asn Leu Ser Phe Ser Thr
                    565                     570                     575

Lys Asn Glu Ser Gly Ile Ile Leu Leu Gly Ser Gly Gly Thr Pro Ala
              580                     585                     590

Pro Pro Arg Arg Lys Arg Arg Gln Thr Gly Gln Ala Tyr Tyr Val Ile
              595                     600                     605

Leu Leu Asn Arg Gly Arg Leu Glu Val His Leu Ser Thr Gly Ala Arg
         610                     615                     620

Thr Met Arg Lys Ile Val Ile Arg Pro Glu Pro Asn Leu Phe His Asp
625                          630                     635                     640

Gly Arg Glu His Ser Val His Val Glu Arg Thr Arg Gly Ile Phe Thr
                    645                     650                     655

Val Gln Val Asp Glu Asn Arg Arg Tyr Met Gln Asn Leu Thr Val Glu
              660                     665                     670

Gln Pro Ile Glu Val Lys Lys Leu Phe Val Gly Gly Ala Pro Pro Glu
         675                     680                     685

Phe Gln Pro Ser Pro Leu Arg Asn Ile Pro Pro Phe Glu Gly Cys Ile
690                     695                     700

Trp Asn Leu Val Ile Asn Ser Val Pro Met Asp Phe Ala Arg Pro Val
705                     710                     715                     720

Ser Phe Lys Asn Ala Asp Ile Gly Arg Cys Ala His Gln Lys Leu Arg
                    725                     730                     735

Glu Asp Glu Asp Gly Ala Ala Pro Ala Glu Ile Val Ile Gln Pro Glu
              740                     745                     750

Pro Val Pro Thr Pro Ala Phe Pro Thr Pro Thr Pro Val Leu Thr His
              755                     760                     765

Gly Pro Cys Ala Ala Glu Ser Glu Pro Ala Leu Leu Ile Gly Ser Lys
770                     775                     780

Gln Phe Gly Leu Ser Arg Asn Ser His Ile Ala Ile Ala Phe Asp Asp
785                     790                     795                     800

Thr Lys Val Lys Asn Arg Leu Thr Ile Glu Leu Glu Val Arg Thr Glu
              805                     810                     815

Ala Glu Ser Gly Leu Leu Phe Tyr Met Ala Ala Ile Asn His Ala Asp
              820                     825                     830

Phe Ala Thr Val Gln Leu Arg Asn Gly Leu Pro Tyr Phe Ser Tyr Asp
         835                     840                     845

Leu Gly Ser Gly Asp Thr His Thr Met Ile Pro Thr Lys Ile Asn Asp
         850                     855                     860

Gly Gln Trp His Lys Ile Lys Ile Met Arg Ser Lys Gln Glu Gly Ile
865                     870                     875                     880

Leu Tyr Val Asp Gly Ala Ser Asn Arg Thr Ile Ser Pro Lys Lys Ala
              885                     890                     895

Asp Ile Leu Asp Val Val Gly Met Leu Tyr Val Gly Gly Leu Pro Ile
              900                     905                     910

| | | | | | | | | | | | | | | |
|---|---|---|---|---|---|---|---|---|---|---|---|---|---|---|
| Asn | Tyr | Thr 915 | Thr | Arg | Arg | Ile | Gly 920 | Pro | Val | Thr | Tyr | Ser 925 | Ile | Asp | Gly |
| Cys | Val 930 | Arg | Asn | Leu | His | Met 935 | Ala | Glu | Ala | Pro | Ala 940 | Asp | Leu | Glu | Gln |
| Pro 945 | Thr | Ser | Ser | Phe | His 950 | Val | Gly | Thr | Cys | Phe 955 | Ala | Asn | Ala | Gln | Arg 960 |
| Gly | Thr | Tyr | Phe | Asp 965 | Gly | Thr | Gly | Phe | Ala | Lys 970 | Ala | Val | Gly | Gly 975 | Phe |
| Lys | Val | Gly | Leu 980 | Asp | Leu | Leu | Val | Glu 985 | Phe | Glu | Phe | Ala | Thr 990 | Thr | Thr |
| Thr | Thr | Gly 995 | Val | Leu | Leu | Gly | Ile 1000 | Ser | Ser | Gln | Lys | Met 1005 | Asp | Gly | Met |
| Gly | Ile | Glu 1010 | Met | Ile | Asp | Glu | Lys 1015 | Leu | Met | Phe | His | Val 1020 | Asp | Asn | Gly |
| Ala | Gly 1025 | Arg | Phe | Thr | Ala | Val 1030 | Tyr | Asp | Ala | Gly | Val 1035 | Pro | Gly | His | Leu 1040 |
| Cys | Asp | Gly | Gln | Trp | His 1045 | Lys | Val | Thr | Ala | Asn 1050 | Lys | Ile | Lys | His 1055 | Arg |
| Ile | Glu | Leu | Thr | Val 1060 | Asp | Gly | Asn | Gln | Val 1065 | Glu | Ala | Gln | Ser 1070 | Pro | Asn |
| Pro | Ala | Ser | Thr 1075 | Ser | Ala | Asp | Thr | Asn 1080 | Asp | Pro | Val | Phe 1085 | Val | Gly | Gly |
| Phe | Pro 1090 | Asp | Asp | Leu | Lys | Gln 1095 | Phe | Gly | Leu | Thr | Thr 1100 | Ser | Ile | Pro | Phe |
| Arg 1105 | Gly | Cys | Ile | Arg | Ser 1110 | Leu | Lys | Leu | Thr | Lys 1115 | Gly | Thr | Ala | Ser 1120 | His |
| Trp | Arg | Leu | Ile | Leu 1125 | Pro | Arg | Pro | Trp | Asn 1130 | | | | | | |

( 2 ) INFORMATION FOR SEQ ID NO:3:

( i ) SEQUENCE CHARACTERISTICS:
        ( A ) LENGTH: 6942 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | | |
|---|---|---|---|---|---|
| CAGCGACTCC | TCTGGCTCCC | GAGAAGTGGA | TCCGGTCGCG | GCCACTACGA | TGCCGGGAGC | 60 |
| CGCCGGGGTC | CTCCTCCTTC | TGCTGCTCTC | CGGAGGCCTC | GGGGGCGTAC | AGGCGCAGCG | 120 |
| GCCGCAGCAG | CAGCGGCAGT | CACAGGCACA | TCAGCAAAGA | GGTTTATTCC | CTGCTGTCCT | 180 |
| GAATCTTGCT | TCTAATGCTC | TTATCACGAC | CAATGCAACA | TGTGGAGAAA | AAGGACCTGA | 240 |
| AATGTACTGC | AAATTGGTAG | AACATGTCCC | TGGGCAGCCT | GTGAGGAACC | CGCAGTGTCG | 300 |
| AATCTGCAAT | CAAAACAGCA | GCAATCCAAA | CCAGAGACAC | CCGATTACAA | ATGCTATTGA | 360 |
| TGGAAAGAAC | ACTTGGTGGC | AGAGTCCCAG | TATTAAGAAT | GGAATCGAAT | ACCATTATGT | 420 |
| GACAATTACA | CTGGATTTAC | AGCAGGTGTT | CCAGATCGCG | TATGTGATTG | TGAAGGCAGC | 480 |
| TAACTCCCCC | CGGCCTGGAA | ACTGGATTTT | GGAACGCTCT | CTTGATGATG | TTGAATACAA | 540 |
| GCCCTGGCAG | TATCATGCTG | TGACAGACAC | GGAGTGCCTA | ACGCTTTACA | ATATTTATCC | 600 |
| CCGCACTGGG | CCACCGTCAT | ATGCCAAAGA | TGATGAGGTC | ATCTGCACTT | CATTTTACTC | 660 |
| CAAGATACAC | CCCTTAGAAA | ATGGAGAGAT | TCACATCTCT | TTAATCAATG | GGAGACCAAG | 720 |
| TGCCGATGAT | CCTTCTCCAG | AACTGCTAGA | ATTTACCTCC | GCTCGCTATA | TTCGCCTGAG | 780 |
| ATTTCAGAGG | ATCCGCACAC | TGAATGCTGA | CTTGATGATG | TTTGCTCACA | AAGACCCAAG | 840 |

```
AGAAATTGAC CCCATTGTCA CCAGAAGATA TTACTACTCG GTCAAGGATA TTTCAGTTGG      900
AGGGATGTGC ATCTGCTATG GTCATGCCAG GGCTTGTCCA CTTGATCCAG CGACAAATAA      960
ATCTCGCTGT GAGTGTGAGC ATAACACATG TGGCGATAGC TGTGATCAGT GCTGTCCAGG     1020
ATTCCATCAG AAACCCTGGA GAGCTGGAAC TTTTCTAACT AAAACTGAAT GTGAAGCATG     1080
CAATTGTCAT GGAAAAGCTG AAGAATGCTA TTATGATGAA AATGTTGCCA GAAGAAATCT     1140
GAGTTTGAAT ATACGTGGAA AGTACATTGG AGGGGTGTC TGCATTAATT GTACCCAAAA     1200
CACTGCTGGT ATAAACTGCG AGACATGTAC AGATGGCTTC TTCAGACCCA AGGGGTATC     1260
TCCAAATTAT CCAAGGCCAT GCCAGCCATG TCATTGCGAT CCAATTGGTT CCTTAAATGA     1320
AGTCTGTGTC AAGGATGAGA ACATGCTCG ACGAGGTTTG GCACCTGGAT CCTGTCATTG      1380
CAAAACTGGT TTTGGAGGTG TGAGCTGTGA TCGGTGTGCC AGGGGCTACA CTGGCTACCC     1440
GGACTGCAAA GCCTGTAACT GCAGTGGGTT AGGGAGCAAA AATGAGGATC CTTGTTTTGG     1500
CCCCTGTATC TGCAAGGAAA ATGTTGAAGG AGGAGACTGT AGTCGTTGCA AATCCGGCTT     1560
CTTCAATTTG CAAGAGGATA ATTGGAAAGG CTGCGATGAG TGTTTCTGTT CAGGGGTTTC     1620
AAACAGATGT CAGAGTTCCT ACTGGACCTA TGGCAAAATA CAAGATATGA GTGGCTGGTA     1680
TCTGACTGAC CTTCCTGGCC GCATTCGAGT GGCTCCCCAG CAGGACGACT TGGACTCACC     1740
TCAGCAGATC AGCATCAGTA ACGCGGAGGC CCGGCAAGCC CTGCCGCACA GCTACTACTG     1800
GAGCGCGCCG GCTCCCTATC TGGGAAACAA ACTCCCAGCA GTAGGAGGAC AGTTGACATT     1860
TACCATATCA TATGACCTTG AAGAAGAGGA AGAAGATACA GAACGTGTTC TCCAGCTTAT     1920
GATTATCTTA GAGGGTAATG ACTTGAGCAT CAGCACAGCC AAGATGAGG TGTACCTGCA      1980
CCCATCTGAA GAACATACTA ATGTATTGTT ACTTAAAGAA GAATCATTTA CCATACATGG     2040
CACACATTTT CCAGTCCGTA GAAAGGAATT TATGACAGTG CTTGCGAATT TGAAGAGAGT     2100
CCTCCTACAA ATCACATACA GCTTTGGGAT GGATGCCATC TTCAGGTTGA GCTCTGTTAA     2160
CCTTGAATCC GCTGTCTCCT ATCCTACTGA TGGAAGCATT GCAGCAGCTG TAGAAGTGTG     2220
TCAGTGCCCA CCAGGGTATA CTGGCTCCTC TTGTGAATCT TGTTGGCCTA GGCACAGGCG     2280
AGTTAACGGC ACTATTTTTG GTGGCATCTG TGAGCCATGT CAGTGCTTTG GTCATGCGGA     2340
GTCCTGTGAT GACGTCACTG GAGAATGCCT GAACTGTAAG GATCACACAG GTGGCCCATA     2400
TTGTGATAAA TGTCTTCCTG GTTTCTATGG CGAGCCTACT AAAGGAACCT CTGAAGACTG     2460
TCAACCCTGT GCCTGTCCAC TCAATATCCC ATCCAATAAC TTTAGCCCAA CGTGCCATTT     2520
AGACCGGAGT CTTGGATTGA TCTGTGATGG ATGCCCTGTC GGGTACACAG GACCACGCTG     2580
TGAGAGGTGT GCAGAAGGCT ATTTTGGACA ACCCTCTGTA CCTGGAGGAT CATGTCAGCC     2640
ATGCCAATGC AATGACAACC TTGACTTCTC CATCCCTGGC AGCTGTGACA GCTTGTCTGG     2700
CTCCTGTCTG ATATGTAAAC CAGGTACAAC AGGCCGGTAC TGTGAGCTCT GTGCTGATGG     2760
ATATTTTGGA GATGCAGTTG ATGCGAAGAA CTGTCAGCCC TGTCGCTGTA ATGCCGGTGG     2820
CTCTTTCTCT GAGGTTTGCC ACAGTCAAAC TGGACAGTGT GAGTGCAGAG CCAACGTTCA     2880
GGGTCAGAGA TGTGACAAAT GCAAGGCTGG GACCTTTGGC CTACAATCAG CAAGGGGCTG     2940
TGTTCCCTGC AACTGCAATT CTTTTGGGTC TAAGTCATTC GACTGTGAAG AGAGTGGACA     3000
ATGTTGGTGC CAACCTGGAG TCACAGGGAA GAAATGTGAC CGCTGTGCCC ACGGCTATTT     3060
CAACTTCCAA GAAGGAGGCT GCACAGCTTG TGAATGTTCT CATCTGGGTA ATAATTGTGA     3120
CCCAAAGACT GGGCGATGCA TTTGCCCACC CAATACCATT GGAGAGAAAT GTTCTAAATG     3180
TGCACCCAAT ACCTGGGGCC ACAGCATTAC CACTGGTTGT AAGGCTTGTA ACTGCAGCAC     3240
```

```
AGTGGGATCC TTGGATTTCC AATGCAATGT AAATACAGGC CAATGCAACT GTCATCCAAA    3300
ATTCTCTGGT GCAAAATGTA CAGAGTGCAG TCGAGGTCAC TGGAACTACC CTCGCTGCAA    3360
TCTCTGTGAC TGCTTCCTCC CTGGGACAGA TGCCACAACC TGTGATTCAG AGACTAAAAA    3420
ATGCTCCTGT AGTGATCAAA CTGGGCAGTG CACTTGTAAG GTGAATGTGG AAGGCATCCA    3480
CTGTGACAGA TGCCGGCCTG GCAAATTCGG ACTCGATGCC AAGAATCCAC TTGGCTGCAG    3540
CAGCTGCTAT TGCTTCGGCA CTACTACCCA GTGCTCTGAA GCAAAGGAC TGATCCGGAC     3600
GTGGGTGACT CTGAAGGCTG AGCAGACCAT TCTACCCCTG GTAGATGAGG CTCTGCAGCA    3660
CACGACCACC AAGGGCATTG TTTTTCAACA TCCAGAGATT GTTGCCCACA TGGACCTGAT    3720
GAGAGAAGAT CTCCATTTGG AACCTTTTA TTGGAAACTT CCAGAACAAT TTGAAGGAAA     3780
GAAGTTGATG GCCTATGGGG GCAAACTCAA GTATGCAATC TATTTCGAGG CTCGGGAAGA   3840
AACAGGTTTC TCTACATATA ATCCTCAAGT GATCATTCGA GGTGGGACAC CTACTCATGC    3900
TAGAATTATC GTCAGGCATA TGGCTGCTCC TCTGATTGGC CAATTGACAA GGCATGAAAT    3960
TGAAATGACA GAGAAAGAAT GGAAATATTA TGGGGATGAT CCTCGAGTCC ATAGAACTGT    4020
GACCCGAGAA GACTTCTTGG ATATACTATA TGATATTCAT TACATTCTTA TCAAAGCTAC    4080
TTATGGAAAT TTCATGCGAC AAAGCAGGAT TTCTGAAATC TCAATGGAGG TAGCTGAACA    4140
AGGACGTGGA ACAACAATGA CTCCTCCAGC TGACTTGATT GAAAAATGTG ATTGTCCCT    4200
GGGCTATTCT GGCCTGTCCT GTGAGGCATG CTTGCCGGGA TTTTATCGAC TGCGTTCTCA    4260
ACCAGGTGGC CGCACCCCTG GACCAACCCT GGGCACCTGT GTTCCATGTC AATGTAATGG    4320
ACACAGCAGC CTGTGTGACC CTGAAACATC GATATGCCAG AATTGTCAAC ATCACACTGC    4380
TGGTGACTTC TGTGAACGAT GTGCTCTTGG ATACTATGGA ATTGTCAAGG GATTGCCAAA    4440
TGACTGTCAG CAATGTGCCT GCCCTCTGAT TTCTTCCAGT AACAATTTCA GCCCTCTTG    4500
TGTCGCAGAA GGACTTGACG ACTACCGCTG CACGGCTTGT CCACGGGGAT ATGAAGGCCA    4560
GTACTGTGAA AGGTGTGCCC CTGGCTATAC TGGCAGTCCA GGCAACCCTG GAGGCTCCTG    4620
CCAAGAATGT GAGTGTGATC CCTATGGCTC ACTGCCTGTG CCCTGTGACC CTGTCACAGG    4680
ATTCTGCACG TGCCGACCTG GAGCCACGGG AAGGAAGTGT GACGGCTGCA AGCACTGGCA    4740
TGCACGCGAG GGCTGGGAGT GTGTTTTTTG TGGAGATGAG TGCACTGGCC TTCTTCTCGG    4800
TGACTTGGCT CGCCTGGAGC AGATGGTCAT GAGCATCAAC CTCACTGGTC CGCTGCCTGC    4860
GCCATATAAA ATGCTGTATG GTCTTGAAAA TATGACTCAG GAGCTAAAGC ACTTGCTGTC    4920
ACCTCAGCGG GCCCCAGAGA GGCTTATTCA GCTGGCAGAG GGCAATCTGA ATACACTCGT    4980
GACCGAAATG AACGAGCTGC TGACCAGGGC TACCAAAGTG ACAGCAGATG GCGAGCAGAC    5040
CGGACAGGAT GCTGAGAGGA CCAACACAAG AGCAAAGTCC CTGGGAGAAT TCATTAAGGA    5100
GCTTGCCCGG GATGCAGAAG CTGTAAATGA AAAAGCTATA AAACTAAATG AAACTCTAGG    5160
AACTCGAGAC GAGGCCTTTG AGAGAAATTT GGAAGGGCTT CAGAAAGAGA TTGACCAGAT    5220
GATTAAAGAA CTGAGGAGGA AAAATCTAGA GACACAAAAG GAAATTGCTG AAGATGAGTT    5280
GGTAGCTGCA GAAGCCCTTC TGAAAAAAGT GAAGAAGCTG TTTGGAGAGT CCCGGGGGGA    5340
AAATGAAGAA ATGGAGAAGG ATCTCCGGGA AAAACTGGCT GACTACAAAA ACAAAGTTGA    5400
TGATGCTTGG GACCTTTTGA GAGAAGCCAC AGATAAAATC AGAGAAGCTA ATCGCCTATT    5460
TGCAGTAAAT CAGAAAAACA TGACTGCATT GGAGAAAAAG AAGGAGGCTG TTGAGAGCGG    5520
CAAACGACAA ATTGAGAACA CTTTAAAAGA AGGCAATGAC ATACTCGATG AAGCCAACCG    5580
TCTTGCAGAT GAAATCAACT CCATCATAGA CTATGTTGAA GACATCCAAA CTAAATTGCC    5640
```

```
ACCTATGTCT  GAGGAGCTTA  ATGATAAAAT  AGATGACCTC  TCCCAAGAAA  TAAAGGACAG     5700

GAAGCTTGCT  GAGAAGGTGT  CCCAGGCTGA  GAGCCACGCA  GCTCAGTTGA  ATGACTCATC     5760

TGCTGTCCTT  GATGGAATCC  TTGATGAGGC  TAAAAACATC  TCCTTCAATG  CCACTGCAGC     5820

CTTCAAAGCT  TACAGCAATA  TTAAGGACTA  TATTGATGAA  GCTGAGAAAG  TTGCCAAAGA     5880

AGCCAAAGAT  CTTGCACATG  AAGCTACAAA  ACTGGCAACA  GGTCCTCGGG  GTTTATTAAA     5940

GGAAGATGCC  AAAGGCTGTC  TTCAGAAAAG  CTTCAGGATT  CTTAACGAAG  CCAAGAAGTT     6000

AGCAAATGAT  GTAAAAGAAA  ATGAAGACCA  TCTAAATGGC  TTAAAAACCA  GGATAGAAAA     6060

TGCTGATGCT  AGAAATGGGG  ATCTCTTGAG  AACTTTGAAT  GACACTTTGG  GAAAGTTATC     6120

AGCTATTCCA  AATGATACAG  CTGCTAAACT  GCAAGCTGTT  AAGGACAAAG  CCAGACAAGC     6180

CAACGACACA  GCTAAAGATG  TACTGGCACA  GATTACAGAG  CTCCACCAGA  ACCTCGATGG     6240

CCTGAAGAAG  AATTACAATA  AACTAGCAGA  CAGCGTCGCC  AAAACGAATG  CTGTGGTTAA     6300

AGATCCTTCC  AAGAACAAAA  TCATTGCCGA  TGCAGATGCC  ACTGTCAAAA  ATTTAGAACA     6360

GGAAGCTGAC  CGGCTAATAG  ATAAACTCAA  ACCCATCAAG  GAACTTGAGG  ATAACCTAAA     6420

GAAAAACATC  TCTGAGATAA  AGGAATTGAT  AAACCAAGCT  CGGAAACAAG  CCAATTCTAT     6480

CAAAGTATCT  GTGTCTTCAG  GAGGTGACTG  CATTCGAACA  TACAAACCAG  AAATCAAGAA     6540

AGGAAGTTAC  AATAATATTG  TTGTCAACGT  AAAGACAGCT  GTTGCTGATA  ACCTCCTCTT     6600

TTATCTTGGA  AGTGCCAAAT  TTATTGACTT  TCTGGCTATA  GAAATGCGTA  AAGGCAAAGT     6660

CAGCTTCCTC  TGGGATGTTG  GATCTGGAGT  TGGACGTGTA  GAGTACCCAG  ATTTGACTAT     6720

TGATGACTCA  TATTGGTACC  GTATCGTAGC  ATCAAGAACT  GGGAGAAATG  GAACTATTTC     6780

TGTGAGAGCC  CTGGATGGAC  CCAAAGCCAG  CATTGTGCCC  AGCACACACC  ATTCGACGTC     6840

TCCTCCAGGG  TACACGATTC  TAGATGTGGA  TGCAAATGCA  ATGCTGTTTG  TTGGTGGCCT     6900

GACTGGGAAA  TTAAAGAAGG  CTGATGCTGT  ACGTGTGATT  AC                         6942
```

( 2 ) INFORMATION FOR SEQ ID NO:4:

( i ) SEQUENCE CHARACTERISTICS:
        ( A ) LENGTH: 3111 amino acids
        ( B ) TYPE: amino acid
        ( D ) TOPOLOGY: linear ( x i ) SEQUENCE DESCRIPTION: SEQ ID NO:4:

```
Met  Pro  Gly  Ala  Ala  Gly  Val  Leu  Leu  Leu  Leu  Leu  Leu  Ser  Gly  Gly
 1              5                        10                       15

Leu  Gly  Gly  Val  Gln  Ala  Gln  Arg  Pro  Gln  Gln  Gln  Arg  Gln  Ser  Gln
         20                       25                       30

Ala  His  Gln  Gln  Arg  Gly  Leu  Phe  Pro  Ala  Val  Leu  Asn  Leu  Ala  Ser
             35                       40                       45

Asn  Ala  Leu  Ile  Thr  Thr  Asn  Ala  Thr  Cys  Gly  Glu  Lys  Gly  Pro  Glu
         50                       55                       60

Met  Tyr  Cys  Lys  Leu  Val  Glu  His  Val  Pro  Gly  Gln  Pro  Val  Arg  Asn
 65                      70                       75                       80

Pro  Gln  Cys  Arg  Ile  Cys  Asn  Gln  Asn  Ser  Ser  Asn  Pro  Asn  Gln  Arg
                     85                       90                       95

His  Pro  Ile  Thr  Asn  Ala  Ile  Asp  Gly  Lys  Asn  Thr  Trp  Trp  Gln  Ser
            100                      105                      110

Pro  Ser  Ile  Lys  Asn  Gly  Ile  Glu  Tyr  His  Tyr  Val  Thr  Ile  Thr  Leu
           115                      120                      125

Asp  Leu  Gln  Gln  Val  Phe  Gln  Ile  Ala  Tyr  Val  Ile  Val  Lys  Ala  Ala
```

-continued

|  |  |  | 130 |  |  |  |  | 135 |  |  |  |  | 140 |  |  |
|---|---|---|---|---|---|---|---|---|---|---|---|---|---|---|---|
| Asn | Ser | Pro | Arg | Pro | Gly | Asn | Trp | Ile | Leu | Glu | Arg | Ser | Leu | Asp | Asp |
| 145 |  |  |  |  | 150 |  |  |  |  | 155 |  |  |  |  | 160 |
| Val | Glu | Tyr | Lys | Pro | Trp | Gln | Tyr | His | Ala | Val | Thr | Asp | Thr | Glu | Cys |
|  |  |  |  | 165 |  |  |  |  | 170 |  |  |  |  | 175 |  |
| Leu | Thr | Leu | Tyr | Asn | Ile | Tyr | Pro | Arg | Thr | Gly | Pro | Pro | Ser | Tyr | Ala |
|  |  |  | 180 |  |  |  |  | 185 |  |  |  |  | 190 |  |  |
| Lys | Asp | Asp | Glu | Val | Ile | Cys | Thr | Ser | Phe | Tyr | Ser | Lys | Ile | His | Pro |
|  |  | 195 |  |  |  |  | 200 |  |  |  | 205 |  |  |  |  |
| Leu | Glu | Asn | Gly | Glu | Ile | His | Ile | Ser | Leu | Ile | Asn | Gly | Arg | Pro | Ser |
|  | 210 |  |  |  |  | 215 |  |  |  |  | 220 |  |  |  |  |
| Ala | Asp | Asp | Pro | Ser | Pro | Glu | Leu | Leu | Glu | Phe | Thr | Ser | Ala | Arg | Tyr |
| 225 |  |  |  |  | 230 |  |  |  |  | 235 |  |  |  |  | 240 |
| Ile | Arg | Leu | Arg | Phe | Gln | Arg | Ile | Arg | Thr | Leu | Asn | Ala | Asp | Leu | Met |
|  |  |  |  | 245 |  |  |  |  | 250 |  |  |  |  | 255 |  |
| Met | Phe | Ala | His | Lys | Asp | Pro | Arg | Glu | Ile | Asp | Pro | Ile | Val | Thr | Arg |
|  |  |  | 260 |  |  |  |  | 265 |  |  |  |  | 270 |  |  |
| Arg | Tyr | Tyr | Tyr | Ser | Val | Lys | Asp | Ile | Ser | Val | Gly | Gly | Met | Cys | Ile |
|  |  | 275 |  |  |  |  | 280 |  |  |  | 285 |  |  |  |  |
| Cys | Tyr | Gly | His | Ala | Arg | Ala | Cys | Pro | Leu | Asp | Pro | Ala | Thr | Asn | Lys |
|  | 290 |  |  |  |  | 295 |  |  |  |  | 300 |  |  |  |  |
| Ser | Arg | Cys | Glu | Cys | Glu | His | Asn | Thr | Cys | Gly | Asp | Ser | Cys | Asp | Gln |
| 305 |  |  |  |  | 310 |  |  |  |  | 315 |  |  |  |  | 320 |
| Cys | Cys | Pro | Gly | Phe | His | Gln | Lys | Pro | Trp | Arg | Ala | Gly | Thr | Phe | Leu |
|  |  |  |  | 325 |  |  |  |  | 330 |  |  |  |  | 335 |  |
| Thr | Lys | Thr | Glu | Cys | Glu | Ala | Cys | Asn | Cys | His | Gly | Lys | Ala | Glu | Glu |
|  |  |  | 340 |  |  |  |  | 345 |  |  |  |  | 350 |  |  |
| Cys | Tyr | Tyr | Asp | Glu | Asn | Val | Ala | Arg | Arg | Asn | Leu | Ser | Leu | Asn | Ile |
|  |  | 355 |  |  |  |  | 360 |  |  |  |  | 365 |  |  |  |
| Arg | Gly | Lys | Tyr | Ile | Gly | Gly | Val | Cys | Ile | Asn | Cys | Thr | Gln | Asn |  |
|  | 370 |  |  |  |  | 375 |  |  |  |  | 380 |  |  |  |  |
| Thr | Ala | Gly | Ile | Asn | Cys | Glu | Thr | Cys | Thr | Asp | Gly | Phe | Phe | Arg | Pro |
| 385 |  |  |  |  | 390 |  |  |  |  | 395 |  |  |  |  | 400 |
| Lys | Gly | Val | Ser | Pro | Asn | Tyr | Pro | Arg | Pro | Cys | Gln | Pro | Cys | His | Cys |
|  |  |  |  | 405 |  |  |  |  | 410 |  |  |  |  | 415 |  |
| Asp | Pro | Ile | Gly | Ser | Leu | Asn | Glu | Val | Cys | Val | Lys | Asp | Glu | Lys | His |
|  |  |  | 420 |  |  |  |  | 425 |  |  |  |  | 430 |  |  |
| Ala | Arg | Arg | Gly | Leu | Ala | Pro | Gly | Ser | Cys | His | Cys | Lys | Thr | Gly | Phe |
|  |  | 435 |  |  |  |  | 440 |  |  |  |  | 445 |  |  |  |
| Gly | Gly | Val | Ser | Cys | Asp | Arg | Cys | Ala | Arg | Gly | Tyr | Thr | Gly | Tyr | Pro |
|  | 450 |  |  |  |  | 455 |  |  |  |  | 460 |  |  |  |  |
| Asp | Cys | Lys | Ala | Cys | Asn | Cys | Ser | Gly | Leu | Gly | Ser | Lys | Asn | Glu | Asp |
| 465 |  |  |  |  | 470 |  |  |  |  | 475 |  |  |  |  | 480 |
| Pro | Cys | Phe | Gly | Pro | Cys | Ile | Cys | Lys | Glu | Asn | Val | Glu | Gly | Gly | Asp |
|  |  |  |  | 485 |  |  |  |  | 490 |  |  |  |  | 495 |  |
| Cys | Ser | Arg | Cys | Lys | Ser | Gly | Phe | Phe | Asn | Leu | Gln | Glu | Asp | Asn | Trp |
|  |  |  | 500 |  |  |  |  | 505 |  |  |  |  | 510 |  |  |
| Lys | Gly | Cys | Asp | Glu | Cys | Phe | Cys | Ser | Gly | Val | Ser | Asn | Arg | Cys | Gln |
|  |  | 515 |  |  |  |  | 520 |  |  |  |  | 525 |  |  |  |
| Ser | Ser | Tyr | Trp | Thr | Tyr | Gly | Lys | Ile | Gln | Asp | Met | Ser | Gly | Trp | Tyr |
|  | 530 |  |  |  |  | 535 |  |  |  |  | 540 |  |  |  |  |
| Leu | Thr | Asp | Leu | Pro | Gly | Arg | Ile | Arg | Val | Ala | Pro | Gln | Gln | Asp | Asp |
| 545 |  |  |  |  | 550 |  |  |  |  | 555 |  |  |  |  | 560 |

```
Leu  Asp  Ser  Pro  Gln  Gln  Ile  Ser  Ile  Ser  Asn  Ala  Glu  Ala  Arg  Gln
               565            570                      575

Ala  Leu  Pro  His  Ser  Tyr  Tyr  Trp  Ser  Ala  Pro  Ala  Pro  Tyr  Leu  Gly
               580                 585                      590

Asn  Lys  Leu  Pro  Ala  Val  Gly  Gly  Gln  Leu  Thr  Phe  Thr  Ile  Ser  Tyr
          595                      600                      605

Asp  Leu  Glu  Glu  Glu  Glu  Asp  Thr  Glu  Arg  Val  Leu  Gln  Leu  Met
610                      615                      620

Ile  Ile  Leu  Glu  Gly  Asn  Asp  Leu  Ser  Ile  Ser  Thr  Ala  Gln  Asp  Glu
625                      630                      635                      640

Val  Tyr  Leu  His  Pro  Ser  Glu  Glu  His  Thr  Asn  Val  Leu  Leu  Leu  Lys
               645                      650                           655

Glu  Glu  Ser  Phe  Thr  Ile  His  Gly  Thr  His  Phe  Pro  Val  Arg  Arg  Lys
               660                      665                      670

Glu  Phe  Met  Thr  Val  Leu  Ala  Asn  Leu  Lys  Arg  Val  Leu  Leu  Gln  Ile
               675                 680                      685

Thr  Tyr  Ser  Phe  Gly  Met  Asp  Ala  Ile  Phe  Arg  Leu  Ser  Ser  Val  Asn
     690                      695                      700

Leu  Glu  Ser  Ala  Val  Ser  Tyr  Pro  Thr  Asp  Gly  Ser  Ile  Ala  Ala  Ala
705                      710                 715                           720

Val  Glu  Val  Cys  Gln  Cys  Pro  Pro  Gly  Tyr  Thr  Gly  Ser  Ser  Cys  Glu
               725                      730                           735

Ser  Cys  Trp  Pro  Arg  His  Arg  Arg  Val  Asn  Gly  Thr  Ile  Phe  Gly  Gly
               740                 745                      750

Ile  Cys  Glu  Pro  Cys  Gln  Cys  Phe  Gly  His  Ala  Glu  Ser  Cys  Asp  Asp
          755                      760                 765

Val  Thr  Gly  Glu  Cys  Leu  Asn  Cys  Lys  Asp  His  Thr  Gly  Gly  Pro  Tyr
     770                      775                 780

Cys  Asp  Lys  Cys  Leu  Pro  Gly  Phe  Tyr  Gly  Glu  Pro  Thr  Lys  Gly  Thr
785                      790                 795                           800

Ser  Glu  Asp  Cys  Gln  Pro  Cys  Ala  Cys  Pro  Leu  Asn  Ile  Pro  Ser  Asn
                    805                 810                      815

Asn  Phe  Ser  Pro  Thr  Cys  His  Leu  Asp  Arg  Ser  Leu  Gly  Leu  Ile  Cys
               820                 825                      830

Asp  Gly  Cys  Pro  Val  Gly  Tyr  Thr  Gly  Pro  Arg  Cys  Glu  Arg  Cys  Ala
          835                      840                 845

Glu  Gly  Tyr  Phe  Gly  Gln  Pro  Ser  Val  Pro  Gly  Gly  Ser  Cys  Gln  Pro
     850                      855                 860

Cys  Gln  Cys  Asn  Asp  Asn  Leu  Asp  Phe  Ser  Ile  Pro  Gly  Ser  Cys  Asp
865                      870                 875                           880

Ser  Leu  Ser  Gly  Ser  Cys  Leu  Ile  Cys  Lys  Pro  Gly  Thr  Thr  Gly  Arg
                    885                 890                           895

Tyr  Cys  Glu  Leu  Cys  Ala  Asp  Gly  Tyr  Phe  Gly  Asp  Ala  Val  Asp  Ala
               900                 905                      910

Lys  Asn  Cys  Gln  Pro  Cys  Arg  Cys  Asn  Ala  Gly  Gly  Ser  Phe  Ser  Glu
          915                 920                      925

Val  Cys  His  Ser  Gln  Thr  Gly  Gln  Cys  Glu  Cys  Arg  Ala  Asn  Val  Gln
     930                      935                 940

Gly  Gln  Arg  Cys  Asp  Lys  Cys  Lys  Ala  Gly  Thr  Phe  Gly  Leu  Gln  Ser
945                      950                      955                      960

Ala  Arg  Gly  Cys  Val  Pro  Cys  Asn  Cys  Asn  Ser  Phe  Gly  Ser  Lys  Ser
                    965                 970                      975

Phe  Asp  Cys  Glu  Glu  Ser  Gly  Gln  Cys  Trp  Cys  Gln  Pro  Gly  Val  Thr
               980                 985                      990
```

```
Gly Lys Lys Cys Asp Arg Cys Ala His Gly Tyr Phe Asn Phe Gln Glu
        995                 1000                    1005
Gly Gly Cys Thr Ala Cys Glu Cys Ser His Leu Gly Asn Asn Cys Asp
    1010                1015                    1020
Pro Lys Thr Gly Arg Cys Ile Cys Pro Pro Asn Thr Ile Gly Glu Lys
1025                1030                1035                1040
Cys Ser Lys Cys Ala Pro Asn Thr Trp Gly His Ser Ile Thr Thr Gly
            1045                1050                    1055
Cys Lys Ala Cys Asn Cys Ser Thr Val Gly Ser Leu Asp Phe Gln Cys
            1060                1065                    1070
Asn Val Asn Thr Gly Gln Cys Asn Cys His Pro Lys Phe Ser Gly Ala
            1075                1080                    1085
Lys Cys Thr Glu Cys Ser Arg Gly His Trp Asn Tyr Pro Arg Cys Asn
        1090                1095                    1100
Leu Cys Asp Cys Phe Leu Pro Gly Thr Asp Ala Thr Thr Cys Asp Ser
1105                1110                1115                1120
Glu Thr Lys Lys Cys Ser Cys Ser Asp Gln Thr Thr Gly Gln Cys Thr
                1125                1130                    1135
Cys Lys Val Asn Val Glu Gly Ile His Cys Asp Arg Cys Arg Pro Gly
                1140                1145                    1150
Lys Phe Gly Leu Asp Ala Lys Asn Pro Leu Gly Cys Ser Ser Cys Tyr
        1155                1160                    1165
Cys Phe Gly Thr Thr Thr Gln Cys Ser Glu Ala Lys Gly Leu Ile Arg
    1170                1175                    1180
Thr Trp Val Thr Leu Lys Ala Glu Gln Thr Ile Leu Pro Leu Val Asp
1185                1190                1195                1200
Glu Ala Leu Gln His Thr Thr Thr Lys Gly Ile Val Phe Gln His Pro
                1205                1210                    1215
Glu Ile Val Ala His Met Asp Leu Met Arg Glu Asp Leu His Leu Glu
            1220                1225                    1230
Pro Phe Tyr Trp Lys Leu Pro Glu Gln Phe Glu Gly Lys Lys Leu Met
        1235                1240                    1245
Ala Tyr Gly Gly Lys Leu Lys Tyr Ala Ile Tyr Phe Glu Ala Arg Glu
        1250                1255                    1260
Glu Thr Gly Phe Ser Thr Tyr Asn Pro Gln Val Ile Ile Arg Gly Gly
1265                1270                1275                1280
Thr Pro Thr His Ala Arg Ile Ile Val Arg His Met Ala Ala Pro Leu
            1285                1290                    1295
Ile Gly Gln Leu Thr Arg His Glu Ile Glu Met Thr Glu Lys Glu Trp
            1300                1305                    1310
Lys Tyr Tyr Gly Asp Asp Pro Arg Val His Arg Thr Val Thr Arg Glu
        1315                1320                    1325
Asp Phe Leu Asp Ile Leu Tyr Asp Ile His Tyr Ile Leu Ile Lys Ala
    1330                1335                    1340
Thr Tyr Gly Asn Phe Met Arg Gln Ser Arg Ile Ser Glu Ile Ser Met
1345                1350                1355                1360
Glu Val Ala Glu Gln Gly Arg Gly Thr Thr Met Thr Pro Pro Ala Asp
                1365                1370                    1375
Leu Ile Glu Lys Cys Asp Cys Pro Leu Gly Tyr Ser Gly Leu Ser Cys
                1380                1385                    1390
Glu Ala Cys Leu Pro Gly Phe Tyr Arg Leu Arg Ser Gln Pro Gly Gly
        1395                1400                    1405
Arg Thr Pro Gly Pro Thr Leu Gly Thr Cys Val Pro Cys Gln Cys Asn
```

-continued

```
               1410                       1415                            1420
Gly His Ser Ser Leu Cys Asp Pro Glu Thr Ser Ile Cys Gln Asn Cys
1425                      1430                      1435                      1440
Gln His His Thr Ala Gly Asp Phe Cys Glu Arg Cys Ala Leu Gly Tyr
                              1445                      1450                      1455
Tyr Gly Ile Val Lys Gly Leu Pro Asn Asp Cys Gln Gln Cys Ala Cys
                              1460                      1465                      1470
Pro Leu Ile Ser Ser Ser Asn Asn Phe Ser Pro Ser Cys Val Ala Glu
                      1475                      1480                      1485
Gly Leu Asp Asp Tyr Arg Cys Thr Ala Cys Pro Arg Gly Tyr Glu Gly
                      1490                      1495                      1500
Gln Tyr Cys Glu Arg Cys Ala Pro Gly Tyr Thr Gly Ser Pro Gly Asn
1505                      1510                      1515                      1520
Pro Gly Gly Ser Cys Gln Glu Cys Glu Cys Asp Pro Tyr Gly Ser Leu
                      1525                      1530                      1535
Pro Val Pro Cys Asp Pro Val Thr Gly Phe Cys Thr Cys Arg Pro Gly
                      1540                      1545                      1550
Ala Thr Gly Arg Lys Cys Asp Gly Cys Lys His Trp His Ala Arg Glu
          1555                      1560                      1565
Gly Trp Glu Cys Val Phe Cys Gly Asp Glu Cys Thr Gly Leu Leu Leu
1570                      1575                      1580
Gly Asp Leu Ala Arg Leu Glu Gln Met Val Met Ser Ile Asn Leu Thr
1585                      1590                      1595                      1600
Gly Pro Leu Pro Ala Pro Tyr Lys Met Leu Tyr Gly Leu Glu Asn Met
                      1605                      1610                      1615
Thr Gln Glu Leu Lys His Leu Leu Ser Pro Gln Arg Ala Pro Glu Arg
                      1620                      1625                      1630
Leu Ile Gln Leu Ala Glu Gly Asn Leu Asn Thr Leu Val Thr Glu Met
                      1635                      1640                      1645
Asn Glu Leu Leu Thr Arg Ala Thr Lys Val Thr Ala Asp Gly Glu Gln
          1650                      1655                      1660
Thr Gly Gln Asp Ala Glu Arg Thr Asn Thr Arg Ala Lys Ser Leu Gly
1665                      1670                      1675                      1680
Glu Phe Ile Lys Glu Leu Ala Arg Asp Ala Glu Ala Val Asn Glu Lys
                      1685                      1690                      1695
Ala Ile Lys Leu Asn Glu Thr Leu Gly Thr Arg Asp Glu Ala Phe Glu
                      1700                      1705                      1710
Arg Asn Leu Glu Gly Leu Gln Lys Glu Ile Asp Gln Met Ile Lys Glu
              1715                      1720                      1725
Leu Arg Arg Lys Asn Leu Glu Thr Gln Lys Glu Ile Ala Glu Asp Glu
          1730                      1735                      1740
Leu Val Ala Ala Glu Ala Leu Leu Lys Lys Val Lys Lys Leu Phe Gly
1745                      1750                      1755                      1760
Glu Ser Arg Gly Glu Asn Glu Glu Met Glu Lys Asp Leu Arg Glu Lys
                      1765                      1770                      1775
Leu Ala Asp Tyr Lys Asn Lys Val Asp Asp Ala Trp Asp Leu Leu Arg
                  1780                      1785                      1790
Glu Ala Thr Asp Lys Ile Arg Glu Ala Asn Arg Leu Phe Ala Val Asn
              1795                      1800                      1805
Gln Lys Asn Met Thr Ala Leu Glu Lys Lys Lys Glu Ala Val Glu Ser
          1810                      1815                      1820
Gly Lys Arg Gln Ile Glu Asn Thr Leu Lys Glu Gly Asn Asp Ile Leu
1825                      1830                      1835                      1840
```

```
Asp Glu Ala Asn Arg Leu Ala Asp Glu Ile Asn Ser Ile Ile Asp Tyr
            1845                1850                1855
Val Glu Asp Ile Gln Thr Lys Leu Pro Pro Met Ser Glu Glu Leu Asn
    1860                1865                1870
Asp Lys Ile Asp Asp Leu Ser Gln Ile Lys Asp Arg Lys Leu Ala
1875                1880                1885
Glu Lys Val Ser Gln Ala Glu Ser His Ala Ala Gln Leu Asn Asp Ser
    1890                1895                1900
Ser Ala Val Leu Asp Gly Ile Leu Asp Glu Ala Lys Asn Ile Ser Phe
1905                1910                1915                1920
Asn Ala Thr Ala Ala Phe Lys Ala Tyr Ser Asn Ile Lys Asp Tyr Ile
                1925                1930                1935
Asp Glu Ala Glu Lys Val Ala Lys Glu Ala Lys Asp Leu Ala His Glu
            1940                1945                1950
Ala Thr Lys Leu Ala Thr Gly Pro Arg Gly Leu Leu Lys Glu Asp Ala
        1955                1960                1965
Lys Gly Cys Leu Gln Lys Ser Phe Arg Ile Leu Asn Glu Ala Lys Lys
    1970                1975                1980
Leu Ala Asn Asp Val Lys Glu Asn Glu Asp His Leu Asn Gly Leu Lys
1985                1990                1995                2000
Thr Arg Ile Glu Asn Ala Asp Ala Arg Asn Gly Asp Leu Leu Arg Thr
            2005                2010                2015
Leu Asn Asp Thr Leu Gly Lys Leu Ser Ala Ile Pro Asn Asp Thr Ala
        2020                2025                2030
Ala Lys Leu Gln Ala Val Lys Asp Lys Ala Arg Gln Ala Asn Asp Thr
        2035                2040                2045
Ala Lys Asp Val Leu Ala Gln Ile Thr Glu Leu His Gln Asn Leu Asp
        2050                2055                2060
Gly Leu Lys Lys Asn Tyr Asn Lys Leu Ala Asp Ser Val Ala Lys Thr
2065                2070                2075                2080
Asn Ala Val Val Lys Asp Pro Ser Lys Asn Lys Ile Ile Ala Asp Ala
                2085                2090                2095
Asp Ala Thr Val Lys Asn Leu Glu Gln Glu Ala Asp Arg Leu Ile Asp
            2100                2105                2110
Lys Leu Lys Pro Ile Lys Glu Leu Glu Asp Asn Leu Lys Lys Asn Ile
        2115                2120                2125
Ser Glu Ile Lys Glu Leu Ile Asn Gln Ala Arg Lys Gln Ala Asn Ser
    2130                2135                2140
Ile Lys Val Ser Val Ser Ser Gly Gly Asp Cys Ile Arg Thr Tyr Lys
2145                2150                2155                2160
Pro Glu Ile Lys Lys Gly Ser Tyr Asn Asn Ile Val Val Asn Val Lys
            2165                2170                2175
Thr Ala Val Ala Asp Asn Leu Leu Phe Tyr Leu Gly Ser Ala Lys Phe
        2180                2185                2190
Ile Asp Phe Leu Ala Ile Glu Met Arg Lys Gly Lys Val Ser Phe Leu
        2195                2200                2205
Trp Asp Val Gly Ser Gly Val Gly Arg Val Glu Tyr Pro Asp Leu Thr
    2210                2215                2220
Ile Asp Asp Ser Tyr Trp Tyr Arg Ile Val Ala Ser Arg Thr Gly Arg
2225                2230                2235                2240
Asn Gly Thr Ile Ser Val Arg Ala Leu Asp Gly Pro Lys Ala Ser Ile
                2245                2250                2255
Val Pro Ser Thr His His Ser Thr Ser Pro Pro Gly Tyr Thr Ile Leu
            2260                2265                2270
```

```
Asp Val Asp Ala Asn Ala Met Leu Phe Val Gly Gly Leu Thr Gly Lys
        2275                2280                2285
Leu Lys Lys Ala Asp Ala Val Arg Val Ile Thr Phe Thr Gly Cys Met
        2290                2295                2300
Gly Glu Thr Tyr Phe Asp Asn Lys Pro Ile Gly Leu Trp Asn Phe Arg
2305                2310                2315                2320
Glu Lys Glu Gly Asp Cys Lys Gly Cys Thr Val Ser Pro Gln Val Glu
                2325                2330                2335
Asp Ser Glu Gly Thr Ile Gln Phe Asp Gly Glu Gly Tyr Ala Leu Val
                2340                2345                2350
Ser Arg Pro Ile Arg Trp Tyr Pro Asn Ile Ser Thr Val Met Phe Lys
        2355                2360                2365
Phe Arg Thr Phe Ser Ser Ser Ala Leu Leu Met Tyr Leu Ala Thr Arg
        2370                2375                2380
Asp Leu Arg Asp Phe Met Ser Val Glu Leu Thr Asp Gly His Ile Lys
2385                2390                2395                2400
Val Ser Tyr Asp Leu Gly Ser Gly Met Ala Ser Val Val Ser Asn Gln
                2405                2410                2415
Asn His Asn Asp Gly Lys Trp Lys Ser Phe Thr Leu Ser Arg Ile Gln
                2420                2425                2430
Lys Gln Ala Asn Ile Ser Ile Val Asp Ile Asp Thr Asn Gln Glu Glu
        2435                2440                2445
Asn Ile Ala Thr Ser Ser Ser Gly Asn Asn Phe Gly Leu Asp Leu Lys
        2450                2455                2460
Ala Asp Asp Lys Ile Tyr Phe Gly Gly Leu Pro Thr Leu Arg Asn Leu
2465                2470                2475                2480
Ser Met Lys Ala Arg Pro Glu Val Asn Leu Lys Lys Tyr Ser Gly Cys
                2485                2490                2495
Leu Lys Asp Ile Glu Ile Ser Arg Thr Pro Tyr Asn Ile Leu Ser Ser
                2500                2505                2510
Pro Asp Tyr Val Gly Val Thr Lys Gly Cys Ser Leu Glu Asn Val Tyr
        2515                2520                2525
Thr Val Ser Phe Pro Lys Pro Gly Phe Val Glu Leu Ser Pro Val Pro
        2530                2535                2540
Ile Asp Val Gly Thr Glu Ile Asn Leu Ser Phe Ser Thr Lys Asn Glu
2545                2550                2555                2560
Ser Gly Ile Ile Leu Leu Gly Ser Gly Gly Thr Pro Ala Pro Pro Arg
                2565                2570                2575
Arg Lys Arg Arg Gln Thr Gly Gln Ala Tyr Tyr Val Ile Leu Leu Asn
                2580                2585                2590
Arg Gly Arg Leu Glu Val His Leu Ser Thr Gly Ala Arg Thr Met Arg
        2595                2600                2605
Lys Ile Val Ile Arg Pro Glu Pro Asn Leu Phe His Asp Gly Arg Glu
        2610                2615                2620
His Ser Val His Val Glu Arg Thr Arg Gly Ile Phe Thr Val Gln Val
2625                2630                2635                2640
Asp Glu Asn Arg Arg Tyr Met Gln Asn Leu Thr Val Glu Gln Pro Ile
                2645                2650                2655
Glu Val Lys Lys Leu Phe Val Gly Gly Ala Pro Pro Glu Phe Gln Pro
                2660                2665                2670
Ser Pro Leu Arg Asn Ile Pro Pro Phe Glu Gly Cys Ile Trp Asn Leu
        2675                2680                2685
Val Ile Asn Ser Val Pro Met Asp Phe Ala Arg Pro Val Ser Phe Lys
```

```
                    2690                      2695                      2700
Asn  Ala  Asp  Ile  Gly  Arg  Cys  Ala  His  Gln  Lys  Leu  Arg  Glu  Asp  Glu
2705                     2710                     2715                     2720

Asp  Gly  Ala  Ala  Pro  Ala  Glu  Ile  Val  Ile  Gln  Pro  Glu  Pro  Val  Pro
                         2725                     2730                     2735

Thr  Pro  Ala  Phe  Pro  Thr  Pro  Thr  Pro  Val  Leu  Thr  His  Gly  Pro  Cys
                         2740                     2745                     2750

Ala  Ala  Glu  Ser  Glu  Pro  Ala  Leu  Leu  Ile  Gly  Ser  Lys  Gln  Phe  Gly
                         2755                     2760                     2765

Leu  Ser  Arg  Asn  Ser  His  Ile  Ala  Ile  Ala  Phe  Asp  Asp  Thr  Lys  Val
                         2770                     2775                     2780

Lys  Asn  Arg  Leu  Thr  Ile  Glu  Leu  Glu  Val  Arg  Thr  Glu  Ala  Glu  Ser
2785                     2790                     2795                     2800

Gly  Leu  Leu  Phe  Tyr  Met  Ala  Ala  Ile  Asn  His  Ala  Asp  Phe  Ala  Thr
                         2805                     2810                     2815

Val  Gln  Leu  Arg  Asn  Gly  Leu  Pro  Tyr  Phe  Ser  Tyr  Asp  Leu  Gly  Ser
                         2820                     2825                     2830

Gly  Asp  Thr  His  Thr  Met  Ile  Pro  Thr  Lys  Ile  Asn  Asp  Gly  Gln  Trp
                         2835                     2840                     2845

His  Lys  Ile  Lys  Ile  Met  Arg  Ser  Lys  Gln  Glu  Gly  Ile  Leu  Tyr  Val
                         2850                     2855                     2860

Asp  Gly  Ala  Ser  Asn  Arg  Thr  Ile  Ser  Pro  Lys  Lys  Ala  Asp  Ile  Leu
2865                     2870                     2875                     2880

Asp  Val  Val  Gly  Met  Leu  Tyr  Val  Gly  Gly  Leu  Pro  Ile  Asn  Tyr  Thr
                         2885                     2890                     2895

Thr  Arg  Arg  Ile  Gly  Pro  Val  Thr  Tyr  Ser  Ile  Asp  Gly  Cys  Val  Arg
                         2900                     2905                     2910

Asn  Leu  His  Met  Ala  Glu  Ala  Pro  Ala  Asp  Leu  Glu  Gln  Pro  Thr  Ser
                         2915                     2920                     2925

Ser  Phe  His  Val  Gly  Thr  Cys  Phe  Asn  Ala  Gln  Arg  Gly  Thr  Tyr
                         2930                     2935                     2940

Phe  Asp  Gly  Thr  Gly  Phe  Ala  Lys  Ala  Val  Gly  Gly  Phe  Lys  Val  Gly
2945                     2950                     2955                     2960

Leu  Asp  Leu  Leu  Val  Glu  Phe  Glu  Phe  Ala  Thr  Thr  Thr  Thr  Thr  Gly
                         2965                     2970                     2975

Val  Leu  Leu  Gly  Ile  Ser  Ser  Gln  Lys  Met  Asp  Gly  Met  Gly  Ile  Glu
                         2980                     2985                     2990

Met  Ile  Asp  Glu  Lys  Leu  Met  Phe  His  Val  Asp  Asn  Gly  Ala  Gly  Arg
                         2995                     3000                     3005

Phe  Thr  Ala  Val  Tyr  Asp  Ala  Gly  Val  Pro  Gly  His  Leu  Cys  Asp  Gly
                         3010                     3015                     3020

Gln  Trp  His  Lys  Val  Thr  Ala  Asn  Lys  Ile  Lys  His  Arg  Ile  Glu  Leu
3025                     3030                     3035                     3040

Thr  Val  Asp  Gly  Asn  Gln  Val  Glu  Ala  Gln  Ser  Pro  Asn  Pro  Ala  Ser
                         3045                     3050                     3055

Thr  Ser  Ala  Asp  Thr  Asn  Asp  Pro  Val  Phe  Val  Gly  Gly  Phe  Pro  Asp
                         3060                     3065                     3070

Asp  Leu  Lys  Gln  Phe  Gly  Leu  Thr  Thr  Ser  Ile  Pro  Phe  Arg  Gly  Cys
                         3075                     3080                     3085

Ile  Arg  Ser  Leu  Lys  Leu  Thr  Lys  Gly  Thr  Ala  Ser  His  Trp  Arg  Leu
                         3090                     3095                     3100

Ile  Leu  Pro  Arg  Pro  Trp  Asn
3105                     3110
```

(2) INFORMATION FOR SEQ ID NO:5:

(i) SEQUENCE CHARACTERISTICS:
        (A) LENGTH: 3075 amino acids
        (B) TYPE: amino acid
        (D) TOPOLOGY: linear (xi) SEQUENCE DESCRIPTION: SEQ ID NO:5:

```
Met Arg Gly Gly Val Leu Leu Val Leu Leu Leu Cys Val Ala Ala Gln
 1               5                  10                  15

Cys Arg Gln Arg Gly Leu Phe Pro Ala Ile Leu Asn Leu Ala Ser Asn
                20                  25                  30

Ala His Ile Ser Thr Asn Ala Thr Cys Gly Glu Lys Gly Pro Glu Met
            35                  40                  45

Phe Cys Lys Leu Val Glu His Val Pro Gly Arg Pro Val Arg Asn Pro
     50                  55                  60

Gln Cys Arg Ile Cys Asp Gly Asn Ser Ala Asn Pro Arg Glu Arg His
 65                  70                  75                  80

Pro Ile Ser His Ala Ile Asp Gly Thr Asn Asn Trp Trp Gln Ser Pro
                85                  90                  95

Ser Ile Gln Asn Gly Arg Glu Tyr His Trp Val Thr Ile Thr Leu Asp
                100                 105                 110

Leu Arg Gln Val Phe Gln Val Ala Tyr Val Ile Ile Lys Ala Ala Asn
            115                 120                 125

Ala Pro Arg Pro Gly Asn Trp Ile Leu Glu Arg Ser Leu Asp Gly Thr
    130                 135                 140

Thr Phe Ser Pro Trp Gln Tyr Tyr Ala Val Ser Asp Ser Glu Cys Leu
145                 150                 155                 160

Ser Arg Tyr Asn Ile Thr Pro Arg Arg Gly Pro Pro Thr Tyr Arg Ala
                165                 170                 175

Asp Asp Glu Val Ile Cys Thr Ser Tyr Tyr Ser Arg Leu Val Pro Leu
            180                 185                 190

Glu His Gly Glu Ile His Thr Ser Leu Ile Asn Gly Arg Pro Ser Ala
        195                 200                 205

Asp Asp Leu Ser Pro Lys Leu Leu Glu Phe Thr Ser Ala Arg Tyr Ile
    210                 215                 220

Arg Leu Arg Phe Glu Arg Ile Arg Thr Leu Asn Ala Asp Leu Met Thr
225                 230                 235                 240

Leu Ser His Arg Glu Pro Lys Glu Leu Asp Pro Met Leu Pro Arg Arg
                245                 250                 255

Tyr Tyr Tyr Ser Ile Lys Asp Ile Ser Val Gly Gly Met Cys Ile Cys
                260                 265                 270

Tyr Gly His Ala Ser Ser Cys Pro Trp Asp Glu Thr Thr Lys Lys Leu
            275                 280                 285

Gln Cys Gln Cys Glu His Asn Thr Cys Gly Glu Ser Cys Asn Arg Cys
    290                 295                 300

Cys Pro Gly Tyr His Gln Gln Pro Trp Arg Pro Gly Thr Val Ser Ser
305                 310                 315                 320

Gly Asn Thr Cys Glu Ala Cys Asn Cys His Asn Lys Ala Lys Asp Cys
                325                 330                 335

Tyr Tyr Asp Glu Ser Val Ala Lys Gln Lys Lys Ser Leu Asn Thr Ala
            340                 345                 350

Gly Gln Phe Arg Gly Gly Gly Val Cys Ile Asn Cys Leu Gln Asn Thr
        355                 360                 365

Met Gly Ile Asn Cys Glu Thr Cys Ile Asp Gly Tyr Tyr Arg Pro His
```

|   |   |   |   |   | 370 |   |   |   |   | 375 |   |   |   |   | 380 |   |   |   |   |
|---|---|---|---|---|-----|---|---|---|---|-----|---|---|---|---|-----|---|---|---|---|
| Lys 385 | Val | Ser | Pro | Tyr | Glu 390 | Asp | Glu | Pro | Cys | Arg 395 | Pro | Cys | Asn | Cys | Asp 400 |
| Pro | Val | Gly | Ser | Leu 405 | Ser | Ser | Val | Cys | Ile 410 | Lys | Asp | Asp | Leu | His 415 | Ser |
| Asp | Leu | Glu | Asn 420 | Gly | Lys | Gln | Pro | Gly 425 | Gln | Cys | Pro | Cys | Lys 430 | Glu | Gly |
| Tyr | Thr | Gly 435 | Glu | Lys | Cys | Asp | Arg 440 | Cys | Gln | Leu | Gly | Tyr 445 | Lys | Asp | Tyr |
| Pro | Thr 450 | Cys | Val | Ser | Cys | Gly 455 | Cys | Asn | Pro | Val | Gly 460 | Ser | Ala | Ser | Asp |
| Glu 465 | Pro | Cys | Thr | Gly | Pro 470 | Cys | Val | Cys | Lys | Glu 475 | Asn | Val | Glu | Gly | Lys 480 |
| Ala | Cys | Asp | Arg | Cys 485 | Lys | Pro | Gly | Phe | Tyr 490 | Asn | Leu | Lys | Glu | Lys 495 | Asn |
| Pro | Arg | Gly | Cys 500 | Ser | Glu | Cys | Phe | Cys 505 | Phe | Gly | Val | Ser | Asp 510 | Val | Cys |
| Ser | Ser | Leu 515 | Ser | Trp | Pro | Leu | Gly 520 | Gln | Val | Asn | Ser | Met 525 | Ser | Gly | Trp |
| Leu | Val 530 | Thr | Asp | Leu | Ile | Ser 535 | Pro | Arg | Lys | Ile | Pro 540 | Ser | Gln | Gln | Asp |
| Ala 545 | Leu | Gly | Gly | Arg | His 550 | Gln | Val | Ser | Ile | Asn 555 | Asn | Thr | Ala | Val | Met 560 |
| Gln | Arg | Leu | Ala | Pro 565 | Lys | Tyr | Tyr | Trp | Ala 570 | Ala | Pro | Glu | Ala | Tyr 575 | Leu |
| Gly | Asn | Lys | Leu 580 | Thr | Ala | Phe | Gly | Gly 585 | Phe | Leu | Lys | Tyr | Thr 590 | Val | Ser |
| Tyr | Asp | Ile 595 | Pro | Val | Glu | Thr | Val 600 | Asp | Ser | Asn | Leu | Met 605 | Ser | His | Ala |
| Asp | Val 610 | Ile | Ile | Lys | Gly | Asn 615 | Gly | Leu | Thr | Leu | Ser 620 | Thr | Gln | Ala | Glu |
| Gly 625 | Leu | Ser | Leu | Gln | Pro 630 | Tyr | Glu | Glu | Tyr | Leu 635 | Asn | Val | Val | Arg | Leu 640 |
| Val | Pro | Glu | Asn | Phe 645 | Gln | Asp | Phe | His | Ser 650 | Lys | Arg | Gln | Ile | Asp 655 | Arg |
| Asp | Gln | Leu | Met 660 | Thr | Val | Leu | Ala | Asn 665 | Val | Thr | His | Leu | Leu 670 | Ile | Arg |
| Ala | Thr | Tyr 675 | Asn | Ser | Ala | Lys | Met 680 | Ala | Leu | Tyr | Arg | Leu 685 | Glu | Ser | Val |
| Ser | Leu 690 | Asp | Ile | Ala | Ser | Ser 695 | Asn | Ala | Ile | Asp | Leu 700 | Val | Val | Ala | Ala |
| Asp 705 | Val | Glu | His | Cys | Glu 710 | Cys | Pro | Gln | Gly | Tyr 715 | Thr | Gly | Thr | Ser | Cys 720 |
| Glu | Ser | Cys | Leu | Ser 725 | Gly | Tyr | Tyr | Arg | Val 730 | Asp | Gly | Ile | Leu | Phe 735 | Gly |
| Gly | Ile | Cys | Gln 740 | Pro | Cys | Glu | Cys | His 745 | Gly | His | Ala | Ala | Glu 750 | Cys | Asn |
| Val | His 755 | Gly | Val | Cys | Ile | Ala 760 | Cys | Ala | His | Asn | Thr 765 | Thr | Gly | Val | His |
| Cys | Glu 770 | Gln | Cys | Leu | Pro | Gly 775 | Phe | Tyr | Gly | Glu | Pro 780 | Ser | Arg | Gly | Thr |
| Pro 785 | Gly | Asp | Cys | Gln | Pro 790 | Cys | Ala | Cys | Pro | Leu 795 | Thr | Ile | Ala | Ser | Asn 800 |

```
Asn Phe Ser Pro Thr Cys His Leu Asn Asp Gly Asp Glu Val Val Cys
                805                 810                 815

Asp Trp Cys Ala Pro Gly Tyr Ser Gly Ala Trp Cys Glu Arg Cys Ala
                820                 825                 830

Asp Gly Tyr Tyr Gly Asn Pro Thr Val Pro Gly Glu Ser Cys Val Pro
            835                 840                 845

Cys Asp Cys Ser Gly Asn Val Asp Pro Ser Glu Ala Gly His Cys Asp
        850                 855                 860

Ser Val Thr Gly Glu Cys Leu Lys Cys Leu Gly Asn Thr Asp Gly Ala
865                 870                 875                 880

His Cys Glu Arg Cys Ala Asp Gly Phe Tyr Gly Asp Ala Val Thr Ala
                885                 890                 895

Lys Asn Cys Arg Ala Cys Glu Cys His Val Lys Gly Ser His Ser Ala
                900                 905                 910

Val Cys His Leu Glu Thr Gly Leu Cys Asp Cys Lys Pro Asn Val Thr
            915                 920                 925

Gly Gln Gln Cys Asp Gln Cys Leu His Gly Tyr Tyr Gly Leu Asp Ser
    930                 935                 940

Gly His Gly Cys Arg Pro Cys Asn Cys Ser Ala Gly Ser Val Ser
945                 950                 955                 960

Asp Gly Cys Thr Asp Glu Gly Gln Cys His Cys Val Pro Gly Val Ala
                965                 970                 975

Gly Lys Arg Cys Asp Arg Cys Ala His Gly Phe Tyr Ala Tyr Gln Asp
            980                 985                 990

Gly Ser Cys Thr Pro Cys Asp Cys Pro His Thr Gln Asn Thr Cys Asp
        995                 1000                1005

Pro Glu Thr Gly Glu Cys Val Cys Pro Pro His Thr Gln Gly Val Lys
    1010                1015                1020

Cys Glu Glu Cys Glu Asp Gly His Trp Gly Tyr Asp Ala Glu Val Gly
1025                1030                1035                1040

Cys Gln Ala Cys Asn Cys Ser Leu Val Gly Ser Thr His His Arg Cys
                1045                1050                1055

Asp Val Val Thr Gly His Cys Gln Cys Lys Ser Lys Phe Gly Gly Arg
            1060                1065                1070

Ala Cys Val Gln Cys Ser Leu Gly Tyr Arg Asp Phe Pro Asp Cys Val
    1075                1080                1085

Pro Cys Asp Cys Asp Leu Arg Gly Thr Ser Gly Asp Ala Cys Asn Leu
    1090                1095                1100

Glu Gln Gly Leu Cys Gly Cys Val Glu Thr Gly Ala Cys Pro Cys
1105                1110                1115                1120

Lys Glu Asn Val Phe Gly Pro Gln Cys Asn Glu Cys Arg Glu Gly Thr
                1125                1130                1135

Phe Ala Leu Arg Ala Asp Asn Pro Leu Gly Cys Ser Pro Cys Phe Cys
                1140                1145                1150

Ser Gly Leu Ser His Leu Cys Ser Glu Leu Glu Asp Tyr Val Arg Thr
                1155                1160                1165

Pro Val Thr Leu Gly Ser Asp Gln Pro Leu Leu Arg Val Val Ser Gln
            1170                1175                1180

Ser Asn Leu Arg Gly Thr Thr Glu Gly Val Tyr Tyr Gln Ala Pro Asp
1185                1190                1195                1200

Phe Leu Leu Asp Ala Ala Thr Val Arg Gln His Ile Arg Ala Glu Pro
                1205                1210                1215

Phe Tyr Trp Arg Leu Pro Gln Gln Phe Gln Gly Asp Gln Leu Met Ala
            1220                1225                1230
```

```
Tyr  Gly  Gly  Lys  Leu  Lys  Tyr  Ser  Val  Ala  Phe  Tyr  Ser  Leu  Asp  Gly
              1235                1240                     1245

Val  Gly  Thr  Ser  Asn  Phe  Glu  Pro  Gln  Val  Leu  Ile  Lys  Gly  Gly  Arg
              1250                1255                     1260

Ile  Arg  Lys  Gln  Val  Ile  Tyr  Met  Asp  Ala  Pro  Ala  Pro  Glu  Asn  Gly
1265                1270                     1275                          1280

Val  Arg  Gln  Glu  Gln  Glu  Val  Ala  Met  Arg  Glu  Asn  Phe  Trp  Lys  Tyr
              1285                1290                          1295

Phe  Asn  Ser  Val  Ser  Glu  Lys  Pro  Val  Thr  Arg  Glu  Asp  Phe  Met  Ser
              1300                1305                          1310

Val  Leu  Ser  Asp  Ile  Glu  Tyr  Ile  Leu  Ile  Lys  Ala  Ser  Tyr  Gly  Gln
              1315                1320                     1325

Gly  Leu  Gln  Gln  Ser  Arg  Ile  Ser  Asp  Ile  Ser  Met  Glu  Val  Gly  Arg
              1330                1335                     1340

Lys  Ala  Glu  Lys  Leu  His  Pro  Glu  Glu  Val  Ala  Ser  Leu  Leu  Glu
1345                1350                     1355                     1360

Asn  Cys  Val  Cys  Pro  Pro  Gly  Thr  Val  Gly  Phe  Ser  Cys  Gln  Asp  Cys
              1365                1370                     1375

Ala  Pro  Gly  Tyr  His  Arg  Gly  Lys  Leu  Pro  Ala  Gly  Ser  Asp  Arg  Gly
              1380                1385                     1390

Pro  Arg  Pro  Leu  Val  Ala  Pro  Cys  Val  Pro  Cys  Ser  Cys  Asn  Asn  His
              1395                1400                     1405

Ser  Asp  Thr  Cys  Asp  Pro  Asn  Thr  Gly  Lys  Cys  Leu  Asn  Cys  Gly  Asp
              1410                1415                     1420

Asn  Thr  Ala  Gly  Asp  His  Cys  Asp  Val  Cys  Thr  Ser  Gly  Tyr  Tyr  Gly
1425                1430                     1435                          1440

Lys  Val  Thr  Gly  Ser  Ala  Ser  Asp  Cys  Ala  Leu  Cys  Ala  Cys  Pro  His
              1445                1450                     1455

Ser  Pro  Pro  Ala  Ser  Phe  Ser  Pro  Thr  Cys  Val  Leu  Glu  Gly  Asp  His
              1460                1465                     1470

Asp  Phe  Arg  Cys  Asp  Ala  Cys  Leu  Leu  Gly  Tyr  Glu  Gly  Lys  His  Cys
              1475                1480                     1485

Glu  Arg  Cys  Ser  Ser  Ser  Tyr  Tyr  Gly  Asn  Pro  Gln  Thr  Pro  Gly  Gly
              1490                1495                     1500

Ser  Cys  Gln  Lys  Cys  Asp  Cys  Asn  Pro  His  Gly  Ser  Val  His  Gly  Asp
1505                1510                     1515                          1520

Cys  Asp  Arg  Thr  Ser  Gly  Gln  Cys  Val  Cys  Arg  Leu  Gly  Ala  Ser  Gly
              1525                1530                     1535

Leu  Arg  Cys  Asp  Glu  Cys  Glu  Pro  Arg  His  Ile  Leu  Met  Glu  Thr  Asp
              1540                1545                     1550

Cys  Val  Ser  Cys  Asp  Asp  Glu  Cys  Val  Gly  Val  Leu  Leu  Asn  Asp  Leu
              1555                1560                     1565

Asp  Glu  Ile  Gly  Asp  Ala  Val  Leu  Ser  Leu  Asn  Leu  Thr  Gly  Ile  Ile
              1570                1575                     1580

Pro  Val  Pro  Tyr  Gly  Ile  Leu  Ser  Asn  Leu  Glu  Asn  Thr  Thr  Lys  Tyr
1585                1590                     1595                          1600

Leu  Gln  Glu  Ser  Leu  Leu  Lys  Glu  Asn  Met  Gln  Lys  Asp  Leu  Gly  Lys
              1605                1610                     1615

Ile  Lys  Leu  Glu  Gly  Val  Ala  Glu  Glu  Thr  Asp  Asn  Leu  Gln  Lys  Lys
              1620                1625                     1630

Leu  Thr  Arg  Met  Leu  Ala  Ser  Thr  Gln  Lys  Val  Asn  Arg  Ala  Thr  Glu
              1635                1640                     1645

Arg  Ile  Phe  Lys  Glu  Ser  Gln  Asp  Leu  Ala  Val  Ala  Ile  Glu  Arg  Leu
```

```
                    1650                    1655                    1660
        Gln  Met  Ser  Ile  Thr  Glu  Ile  Met  Glu  Lys  Thr  Thr  Leu  Asn  Gln  Thr
   1665                    1670                    1675                    1680

Leu  Asp  Glu  Asp  Phe  Leu  Leu  Pro  Asn  Ser  Thr  Leu  Gln  Asn  Met  Gln
                            1685                    1690                    1695

Gln  Asn  Gly  Thr  Ser  Leu  Leu  Glu  Ile  Met  Gln  Ile  Arg  Asp  Phe  Thr
                            1700                    1705                    1710

Gln  Leu  His  Gln  Asn  Ala  Thr  Leu  Glu  Leu  Lys  Ala  Ala  Glu  Asp  Leu
                            1715                    1720                    1725

Leu  Ser  Gln  Ile  Gln  Glu  Asn  Tyr  Gln  Lys  Pro  Leu  Glu  Glu  Leu  Glu
                            1730                    1735                    1740

Val  Leu  Lys  Glu  Ala  Ala  Ser  His  Val  Leu  Ser  Lys  His  Asn  Asn  Glu
   1745                    1750                    1755                    1760

Leu  Lys  Ala  Ala  Glu  Ala  Leu  Val  Arg  Glu  Ala  Glu  Ala  Lys  Met  Gln
                            1765                    1770                    1775

Glu  Ser  Asn  His  Leu  Leu  Leu  Met  Val  Asn  Ala  Asn  Leu  Arg  Glu  Phe
                            1780                    1785                    1790

Ser  Asp  Lys  Lys  Leu  His  Val  Gln  Glu  Glu  Gln  Asn  Leu  Thr  Ser  Glu
                            1795                    1800                    1805

Leu  Ile  Val  Gln  Gly  Arg  Gly  Leu  Ile  Asp  Ala  Ala  Ala  Ala  Gln  Thr
                            1810                    1815                    1820

Asp  Ala  Val  Gln  Asp  Ala  Leu  Glu  His  Leu  Glu  Asp  His  Gln  Asp  Lys
   1825                    1830                    1835                    1840

Leu  Leu  Leu  Trp  Ser  Ala  Lys  Ile  Arg  His  His  Ile  Asp  Asp  Leu  Val
                            1845                    1850                    1855

Met  His  Met  Ser  Gln  Arg  Asn  Ala  Val  Asp  Leu  Val  Tyr  Arg  Ala  Glu
                            1860                    1865                    1870

Asp  His  Ala  Thr  Glu  Phe  Gln  Arg  Leu  Ala  Asp  Val  Leu  Tyr  Ser  Gly
                            1875                    1880                    1885

Leu  Glu  Asn  Ile  Arg  Asn  Val  Ser  Leu  Asn  Ala  Thr  Ser  Ala  Ala  Tyr
                            1890                    1895                    1900

Val  His  Tyr  Asn  Ile  Gln  Ser  Leu  Ile  Glu  Glu  Ser  Glu  Glu  Leu  Ala
   1905                    1910                    1915                    1920

Arg  Asp  Ala  His  Arg  Thr  Val  Thr  Glu  Thr  Ser  Leu  Leu  Ser  Glu  Ser
                            1925                    1930                    1935

Leu  Val  Ser  Asn  Gly  Lys  Ala  Ala  Val  Gln  Arg  Ser  Ser  Arg  Phe  Leu
                            1940                    1945                    1950

Lys  Glu  Gly  Asn  Asn  Leu  Ser  Arg  Lys  Leu  Pro  Gly  Ile  Ala  Leu  Glu
                            1955                    1960                    1965

Leu  Ser  Glu  Leu  Arg  Asn  Lys  Thr  Asn  Arg  Phe  Gln  Glu  Asn  Ala  Val
                            1970                    1975                    1980

Glu  Ile  Thr  Arg  Gln  Thr  Asn  Glu  Ser  Leu  Leu  Ile  Leu  Arg  Ala  Ile
                            1985                    1990                    1995                    2000

Pro  Glu  Gly  Ile  Arg  Asp  Lys  Gly  Ala  Lys  Thr  Lys  Glu  Leu  Ala  Thr
                            2005                    2010                    2015

Ser  Ala  Ser  Gln  Ser  Ala  Val  Ser  Thr  Leu  Arg  Asp  Val  Ala  Gly  Leu
                            2020                    2025                    2030

Ser  Gln  Glu  Leu  Leu  Asn  Thr  Ser  Ala  Ser  Leu  Ser  Arg  Val  Asn  Thr
                            2035                    2040                    2045

Thr  Leu  Arg  Glu  Thr  His  Gln  Leu  Leu  Gln  Asp  Ser  Thr  Met  Ala  Thr
                            2050                    2055                    2060

Leu  Leu  Ala  Gly  Arg  Lys  Val  Lys  Asp  Val  Glu  Ile  Gln  Ala  Lys  Val
                            2065                    2070                    2075                    2080
```

```
Leu Phe Asp Arg Leu Lys Pro Leu Lys Met Leu Glu Glu Asn Leu Ser
            2085                2090                2095
Arg Asn Leu Ser Glu Ile Lys Leu Leu Ile Ser Gln Ala Arg Lys Gln
        2100                2105                2110
Ala Ala Ser Ile Lys Val Ala Val Ser Ala Asp Arg Asp Cys Ile Arg
        2115                2120                2125
Ala Tyr Gln Pro Gln Ile Ser Ser Thr Asn Tyr Asn Thr Leu Thr Leu
        2130                2135                2140
Asn Val Lys Thr Gln Glu Pro Asp Asn Leu Leu Phe Tyr Leu Gly Ser
2145                2150                2155                2160
Ser Thr Ala Ser Asp Phe Leu Ala Val Glu Met Arg Arg Gly Arg Val
            2165                2170                2175
Ala Phe Leu Trp Asp Leu Gly Ser Gly Ser Thr Arg Leu Glu Phe Pro
            2180                2185                2190
Asp Phe Pro Ile Asp Asp Asn Arg Trp His Ser Ile His Val Ala Arg
            2195                2200                2205
Phe Gly Asn Ile Gly Ser Leu Ser Val Lys Glu Met Ser Ser Asn Gln
            2210                2215                2220
Lys Ser Pro Thr Lys Thr Ser Lys Ser Pro Gly Thr Ala Asn Val Leu
2225                2230                2235                2240
Asp Val Asn Asn Ser Thr Leu Met Phe Val Gly Gly Leu Gly Gly Gln
                2245                2250                2255
Ile Lys Lys Ser Pro Ala Val Lys Val Thr His Phe Lys Gly Cys Leu
            2260                2265                2270
Gly Glu Ala Phe Leu Asn Gly Lys Ser Ile Gly Leu Trp Asn Tyr Ile
            2275                2280                2285
Glu Arg Glu Gly Lys Cys Arg Gly Cys Phe Gly Ser Ser Gln Asn Glu
            2290                2295                2300
Asp Pro Ser Phe His Phe Asp Gly Ser Gly Tyr Ser Val Val Glu Lys
2305                2310                2315                2320
Ser Leu Pro Ala Thr Val Thr Gln Ile Ile Met Leu Phe Asn Thr Phe
            2325                2330                2335
Ser Pro Asn Gly Leu Leu Leu Tyr Leu Gly Ser Tyr Gly Thr Lys Asp
            2340                2345                2350
Phe Leu Ser Ile Glu Leu Phe Arg Gly Arg Val Lys Val Met Thr Asp
            2355                2360                2365
Leu Gly Ser Gly Pro Ile Thr Leu Leu Thr Asp Arg Arg Tyr Asn Asn
            2370                2375                2380
Gly Thr Trp Tyr Lys Ile Ala Phe Gln Arg Asn Arg Lys Gln Gly Val
2385                2390                2395                2400
Leu Ala Val Ile Asp Ala Tyr Asn Thr Ser Asn Lys Glu Thr Lys Gln
            2405                2410                2415
Gly Glu Thr Pro Gly Ala Ser Ser Asp Leu Asn Arg Leu Asp Lys Asp
            2420                2425                2430
Pro Ile Tyr Val Gly Gly Leu Pro Arg Ser Arg Val Val Arg Arg Gly
            2435                2440                2445
Val Thr Thr Lys Ser Phe Val Gly Cys Ile Lys Asn Leu Glu Ile Ser
            2450                2455                2460
Arg Ser Thr Phe Asp Leu Leu Arg Asn Ser Tyr Gly Val Arg Lys Gly
2465                2470                2475                2480
Cys Leu Leu Glu Pro Ile Arg Ser Val Ser Phe Leu Lys Gly Gly Tyr
                2485                2490                2495
Ile Glu Leu Pro Pro Lys Ser Leu Ser Pro Glu Ser Glu Trp Leu Val
            2500                2505                2510
```

```
Thr Phe Ala Thr Thr Asn Ser Ser Gly Ile Ile Leu Ala Ala Leu Gly
        2515                2520                2525
Gly Asp Val Glu Lys Arg Gly Asp Arg Glu Glu Ala His Val Pro Phe
        2530                2535                2540
Phe Ser Val Met Leu Ile Gly Gly Asn Ile Glu Val His Val Asn Pro
2545                2550                2555                2560
Gly Asp Gly Thr Gly Leu Arg Lys Ala Leu Leu His Ala Pro Thr Gly
                2565                2570                2575
Thr Cys Ser Asp Gly Gln Ala His Ser Ile Ser Leu Val Arg Asn Arg
                2580                2585                2590
Arg Ile Ile Thr Val Gln Leu Asp Glu Asn Asn Pro Val Glu Met Lys
                2595                2600                2605
Leu Gly Thr Leu Val Glu Ser Arg Thr Ile Asn Val Ser Asn Leu Tyr
                2610                2615                2620
Val Gly Gly Ile Pro Glu Gly Glu Gly Thr Ser Leu Leu Thr Met Arg
2625                2630                2635                2640
Arg Ser Phe His Gly Cys Ile Lys Asn Leu Ile Phe Asn Leu Glu Leu
                2645                2650                2655
Leu Asp Phe Asn Ser Ala Val Gly His Glu Gln Val Asp Leu Asp Thr
                2660                2665                2670
Cys Trp Leu Ser Glu Arg Pro Lys Leu Ala Pro Asp Ala Glu Asp Ser
                2675                2680                2685
Lys Leu Leu Arg Glu Pro Arg Ala Phe Pro Glu Gln Cys Val Val Asp
                2690                2695                2700
Ala Ala Leu Glu Tyr Val Pro Gly Ala His Gln Phe Gly Leu Thr Gln
2705                2710                2715                2720
Asn Ser His Phe Ile Leu Pro Phe Asn Gln Ser Ala Val Arg Lys Lys
                2725                2730                2735
Leu Ser Val Glu Leu Ser Ile Arg Thr Leu Ala Ser Ser Gly Leu Ile
                2740                2745                2750
Tyr Tyr Met Ala His Gln Asn Gln Ala Asp Tyr Ala Val Leu Gln Leu
                2755                2760                2765
His Gly Gly Arg Leu His Phe Met Phe Asp Leu Gly Lys Gly Arg Thr
        2770                2775                2780
Lys Val Ser His Pro Ala Leu Leu Ser Asp Gly Lys Trp His Thr Val
2785                2790                2795                2800
Lys Thr Asp Tyr Val Lys Arg Lys Gly Phe Ile Thr Val Asp Gly Arg
                2805                2810                2815
Glu Ser Pro Met Val Thr Val Val Gly Asp Gly Thr Met Leu Asp Val
                2820                2825                2830
Glu Gly Leu Phe Tyr Leu Gly Gly Leu Pro Ser Gln Tyr Gln Ala Arg
                2835                2840                2845
Lys Ile Gly Asn Ile Thr His Ser Ile Pro Ala Cys Ile Gly Asp Val
                2850                2855                2860
Thr Val Asn Ser Lys Gln Leu Asp Lys Asp Ser Pro Val Ser Ala Phe
2865                2870                2875                2880
Thr Val Asn Arg Cys Tyr Ala Val Ala Gln Glu Gly Thr Tyr Phe Asp
                2885                2890                2895
Gly Ser Gly Tyr Ala Ala Leu Val Lys Glu Gly Tyr Lys Val Gln Ser
                2900                2905                2910
Asp Val Asn Ile Thr Leu Glu Phe Arg Thr Ser Ser Gln Asn Gly Val
                2915                2920                2925
Leu Leu Gly Ile Ser Thr Ala Lys Val Asp Ala Ile Gly Leu Glu Leu
```

|     |     |     |     |     |     |     |     |     |     |     |     |     |     |
| --- | --- | --- | --- | --- | --- | --- | --- | --- | --- | --- | --- | --- | --- |
|     |     | 2930 |     |     |     | 2935 |     |     |     |     | 2940 |     |     |
| Val | Asp | Gly | Lys | Val | Leu | Phe | His | Val | Asn | Asn | Gly | Ala | Gly | Arg | Ile |
| 2945 |     |     |     |     | 2950 |     |     |     | 2955 |     |     |     | 2960 |
| Thr | Pro | Ala | Tyr | Glu | Pro | Lys | Thr | Ala | Thr | Val | Leu | Cys | Asp | Gly | Lys |
|     |     |     |     | 2965 |     |     |     | 2970 |     |     |     |     | 2975 |
| Trp | His | Thr | Leu | Gln | Ala | Asn | Lys | Ser | Lys | His | Arg | Ile | Thr | Leu | Ile |
|     |     |     | 2980 |     |     |     | 2985 |     |     |     |     | 2990 |
| Val | Asp | Gly | Asn | Ala | Val | Gly | Ala | Glu | Ser | Pro | His | Thr | Gln | Ser | Thr |
|     |     | 2995 |     |     |     | 3000 |     |     |     |     | 3005 |
| Ser | Val | Asp | Thr | Asn | Asn | Pro | Ile | Tyr | Val | Gly | Gly | Tyr | Pro | Ala | Gly |
|     |     | 3010 |     |     |     | 3015 |     |     |     |     | 3020 |
| Val | Lys | Gln | Lys | Cys | Leu | Arg | Ser | Gln | Thr | Ser | Phe | Arg | Gly | Cys | Leu |
| 3025 |     |     |     | 3030 |     |     |     | 3035 |     |     |     |     | 3040 |
| Arg | Lys | Leu | Ala | Leu | Ile | Lys | Ser | Pro | Gln | Val | Gln | Ser | Leu | Asp | Phe |
|     |     |     |     | 3045 |     |     |     | 3050 |     |     |     |     | 3055 |
| Ser | Arg | Ala | Phe | Glu | Leu | His | Gly | Val | Phe | Leu | His | Ser | Cys | Pro | Gly |
|     |     |     |     | 3060 |     |     |     | 3065 |     |     |     |     | 3070 |
| Pro | Ser | Pro |
|     |     | 3075 |

( 2 ) INFORMATION FOR SEQ ID NO:6:

( i ) SEQUENCE CHARACTERISTICS:
        ( A ) LENGTH: 249 amino acids
        ( B ) TYPE: amino acid
        ( D ) TOPOLOGY: linear ( x i ) SEQUENCE DESCRIPTION: SEQ ID NO:6:

|     |     |     |     |     |     |     |     |     |     |     |     |     |     |     |     |
| --- | --- | --- | --- | --- | --- | --- | --- | --- | --- | --- | --- | --- | --- | --- | --- |
| Gln | Glu | Pro | Glu | Phe | Ser | Tyr | Gly | Cys | Ala | Glu | Gly | Ser | Cys | Tyr | Pro |
| 1 |     |     |     | 5 |     |     |     |     | 10 |     |     |     |     | 15 |
| Ala | Thr | Gly | Asp | Leu | Leu | Ile | Gly | Arg | Ala | Gln | Lys | Leu | Ser | Val | Thr |
|     |     |     | 20 |     |     |     |     | 25 |     |     |     |     | 30 |
| Ser | Thr | Cys | Gly | Leu | His | Lys | Pro | Glu | Pro | Tyr | Cys | Ile | Val | Ser | His |
|     |     | 35 |     |     |     |     | 40 |     |     |     |     | 45 |
| Leu | Gln | Glu | Asp | Lys | Lys | Cys | Phe | Ile | Cys | Asn | Ser | Gln | Asp | Pro | Tyr |
|     | 50 |     |     |     |     | 55 |     |     |     |     | 60 |
| His | Glu | Thr | Leu | Asn | Pro | Asp | Ser | His | Leu | Ile | Glu | Asn | Val | Val | Thr |
| 65 |     |     |     |     | 70 |     |     |     |     | 75 |     |     |     |     | 80 |
| Thr | Phe | Ala | Pro | Asn | Arg | Leu | Lys | Ile | Trp | Trp | Gln | Ser | Glu | Asn | Gly |
|     |     |     |     | 85 |     |     |     |     | 90 |     |     |     |     | 95 |
| Val | Glu | Asn | Val | Thr | Ile | Gln | Leu | Asp | Leu | Glu | Ala | Glu | Phe | His | Phe |
|     |     |     |     | 100 |     |     |     | 105 |     |     |     |     | 110 |
| Thr | His | Leu | Ile | Met | Thr | Phe | Lys | Thr | Phe | Arg | Pro | Ala | Ala | Met | Leu |
|     |     |     | 115 |     |     |     |     | 120 |     |     |     |     | 125 |
| Ile | Glu | Arg | Ser | Ser | Asp | Phe | Gly | Lys | Thr | Trp | Gly | Val | Tyr | Arg | Tyr |
|     | 130 |     |     |     |     | 135 |     |     |     |     | 140 |
| Phe | Ala | Tyr | Asp | Cys | Glu | Ala | Ser | Phe | Pro | Gly | Ile | Ser | Thr | Gly | Pro |
| 145 |     |     |     |     | 150 |     |     |     |     | 155 |     |     |     |     | 160 |
| Met | Lys | Lys | Val | Asp | Asp | Ile | Ile | Cys | Asp | Ser | Arg | Tyr | Ser | Asp | Ile |
|     |     |     |     | 165 |     |     |     |     | 170 |     |     |     |     | 175 |
| Glu | Pro | Ser | Thr | Glu | Gly | Glu | Val | Ile | Phe | Arg | Ala | Leu | Asp | Pro | Ala |
|     |     |     | 180 |     |     |     |     | 185 |     |     |     |     | 190 |
| Phe | Lys | Ile | Glu | Asp | Pro | Tyr | Ser | Pro | Arg | Ile | Gln | Asn | Leu | Leu | Lys |
|     |     |     | 195 |     |     |     |     | 200 |     |     |     |     | 205 |
| Ile | Thr | Asn | Leu | Arg | Ile | Lys | Phe | Val | Lys | Leu | His | Thr | Leu | Gly | Asp |
|     | 210 |     |     |     |     | 215 |     |     |     |     | 220 |

| | | | | | | | | | | | | | | | |
|---|---|---|---|---|---|---|---|---|---|---|---|---|---|---|---|
| Asn | Leu | Leu | Asp | Ser | Arg | Met | Glu | Ile | Arg | Glu | Lys | Tyr | Tyr | Tyr | Ala |
| 225 | | | | | 230 | | | | | 235 | | | | | 240 |
| Val | Tyr | Asp | Met | Val | Val | Arg | Gly | Asn | | | | | | | |
| | | | | 245 | | | | | | | | | | | |

(2) INFORMATION FOR SEQ ID NO:7:

(i) SEQUENCE CHARACTERISTICS:
 (A) LENGTH: 250 amino acids
 (B) TYPE: amino acid
 (D) TOPOLOGY: linear (xi) SEQUENCE DESCRIPTION: SEQ ID NO:7:

| | | | | | | | | | | | | | | | |
|---|---|---|---|---|---|---|---|---|---|---|---|---|---|---|---|
| Gln | Val | Pro | Ser | Leu | Asp | Val | Pro | Gly | Cys | Ser | Arg | Gly | Ser | Cys | Tyr |
| 1 | | | | 5 | | | | | 10 | | | | | 15 | |
| Pro | Ala | Thr | Gly | Asp | Leu | Leu | Val | Gly | Arg | Ala | Asp | Arg | Leu | Thr | Ala |
| | | | 20 | | | | | 25 | | | | | 30 | | |
| Ser | Ser | Thr | Cys | Gly | Leu | His | Ser | Pro | Gln | Pro | Tyr | Cys | Ile | Val | Ser |
| | | | 35 | | | | | 40 | | | | | 45 | | |
| His | Leu | Gln | Asp | Glu | Lys | Lys | Cys | Phe | Leu | Cys | Asp | Ser | Arg | Arg | Pro |
| | | 50 | | | | | 55 | | | | | 60 | | | |
| Phe | Ser | Ala | Arg | Asp | Asn | Pro | Asn | Ser | His | Arg | Ile | Gln | Asn | Val | Val |
| 65 | | | | | 70 | | | | | 75 | | | | | 80 |
| Thr | Ser | Phe | Ala | Pro | Gln | Arg | Arg | Thr | Ala | Trp | Trp | Gln | Ser | Glu | Asn |
| | | | | 85 | | | | | 90 | | | | | 95 | |
| Gly | Val | Pro | Met | Val | Thr | Ile | Gln | Leu | Asp | Leu | Glu | Ala | Glu | Phe | His |
| | | | 100 | | | | | 105 | | | | | 110 | | |
| Phe | Thr | His | Leu | Ile | Met | Thr | Phe | Lys | Thr | Phe | Arg | Pro | Ala | Ala | Met |
| | | 115 | | | | | 120 | | | | | 125 | | | |
| Leu | Val | Glu | Arg | Ser | Ala | Asp | Phe | Gly | Arg | Thr | Trp | Arg | Val | Tyr | Arg |
| | 130 | | | | | 135 | | | | | 140 | | | | |
| Tyr | Phe | Ser | Tyr | Asp | Cys | Gly | Ala | Asp | Phe | Pro | Gly | Ile | Pro | Leu | Ala |
| 145 | | | | | 150 | | | | | 155 | | | | | 160 |
| Pro | Pro | Arg | Arg | Trp | Asp | Asp | Val | Val | Cys | Glu | Ser | Arg | Tyr | Ser | Glu |
| | | | | 165 | | | | | 170 | | | | | 175 | |
| Ile | Glu | Pro | Ser | Thr | Glu | Gly | Glu | Val | Ile | Tyr | Arg | Val | Leu | Asp | Pro |
| | | | 180 | | | | | 185 | | | | | 190 | | |
| Ala | Ile | Pro | Ile | Pro | Asp | Pro | Tyr | Ser | Ser | Arg | Ile | Gln | Asn | Leu | Leu |
| | | 195 | | | | | 200 | | | | | 205 | | | |
| Lys | Ile | Thr | Asn | Leu | Arg | Val | Asn | Leu | Thr | Arg | Leu | His | Thr | Leu | Gly |
| | 210 | | | | | 215 | | | | | 220 | | | | |
| Asp | Asn | Leu | Leu | Asp | Pro | Arg | Arg | Glu | Ile | Arg | Glu | Lys | Tyr | Tyr | Tyr |
| 225 | | | | | 230 | | | | | 235 | | | | | 240 |
| Ala | Leu | Tyr | Glu | Leu | Val | Ile | Arg | Gly | Asn | | | | | | |
| | | | | 245 | | | | | 250 | | | | | | |

(2) INFORMATION FOR SEQ ID NO:8:

(i) SEQUENCE CHARACTERISTICS:
 (A) LENGTH: 252 amino acids
 (B) TYPE: amino acid
 (D) TOPOLOGY: linear (xi) SEQUENCE DESCRIPTION: SEQ ID NO:8:

| | | | | | | | | | | | | | | | |
|---|---|---|---|---|---|---|---|---|---|---|---|---|---|---|---|
| Arg | Gln | Arg | Gly | Leu | Phe | Pro | Ala | Ile | Leu | Asn | Leu | Ala | Ser | Asn | Ala |
| 1 | | | | 5 | | | | | 10 | | | | | 15 | |
| His | Ile | Ser | Thr | Asn | Ala | Thr | Cys | Gly | Glu | Lys | Gly | Pro | Glu | Met | Phe |
| | | | 20 | | | | | 25 | | | | | 30 | | |

|     |     |     |     |     |     |     |     |     |     |     |     |     |     |     |
| --- | --- | --- | --- | --- | --- | --- | --- | --- | --- | --- | --- | --- | --- | --- |
| Cys | Lys | Leu 35 | Val | Glu | His | Val | Pro 40 | Gly | Arg | Pro | Val | Arg 45 | Asn | Pro | Gln |
| Cys | Arg 50 | Ile | Cys | Asp | Gly | Asn 55 | Ser | Ala | Asn | Pro | Arg 60 | Glu | Arg | His | Pro |
| Ile 65 | Ser | His | Ala | Ile | Asp 70 | Gly | Thr | Asn | Asn | Trp 75 | Trp | Gln | Ser | Pro | Ser 80 |
| Ile | Gln | Asn | Gly | Arg 85 | Glu | Tyr | His | Trp | Val 90 | Thr | Ile | Thr | Leu | Asp 95 | Leu |
| Arg | Gln | Val | Phe 100 | Gln | Val | Ala | Tyr | Val 105 | Ile | Ile | Lys | Ala | Ala 110 | Asn | Ala |
| Pro | Arg | Pro 115 | Gly | Asn | Trp | Ile | Leu 120 | Glu | Arg | Ser | Leu | Asp 125 | Gly | Thr | Thr |
| Phe | Ser 130 | Pro | Trp | Gln | Tyr | Tyr 135 | Ala | Val | Ser | Asp | Ser 140 | Glu | Cys | Leu | Ser |
| Arg 145 | Tyr | Asn | Ile | Thr | Pro 150 | Arg | Arg | Gly | Pro | Pro 155 | Thr | Tyr | Arg | Ala | Asp 160 |
| Asp | Glu | Val | Ile | Cys 165 | Thr | Ser | Tyr | Tyr | Ser 170 | Arg | Leu | Val | Pro | Leu 175 | Glu |
| His | Gly | Glu | Ile 180 | His | Thr | Ser | Leu | Ile 185 | Asn | Gly | Arg | Pro | Ser 190 | Ala | Asp |
| Asp | Leu | Ser 195 | Pro | Lys | Leu | Leu | Glu 200 | Phe | Thr | Ser | Ala | Arg 205 | Tyr | Ile | Arg |
| Leu | Arg 210 | Phe | Glu | Arg | Ile | Arg 215 | Thr | Leu | Asn | Ala | Asp 220 | Leu | Met | Thr | Leu |
| Ser | His 225 | Arg | Glu | Pro | Lys | Glu 230 | Leu | Asp | Pro | Met 235 | Leu | Pro | Arg | Arg | Tyr 240 |
| Tyr | Tyr | Ser | Ile | Lys 245 | Asp | Ile | Ser | Val | Gly 250 | Gly | Met |  |  |  |  |

( 2 ) INFORMATION FOR SEQ ID NO:9:

( i ) SEQUENCE CHARACTERISTICS:
        ( A ) LENGTH: 252 amino acids
        ( B ) TYPE: amino acid
        ( D ) TOPOLOGY: linear ( x i ) SEQUENCE DESCRIPTION: SEQ ID NO:9:

|     |     |     |     |     |     |     |     |     |     |     |     |     |     |     |
| --- | --- | --- | --- | --- | --- | --- | --- | --- | --- | --- | --- | --- | --- | --- |
| Gln 1 | Gln | Arg | Gly | Leu 5 | Phe | Pro | Ala | Ile | Leu 10 | Asn | Leu | Ala | Thr | Asn 15 | Ala |
| His | Ile | Ser | Ala 20 | Asn | Ala | Thr | Cys | Gly 25 | Glu | Lys | Gly | Pro | Glu 30 | Met | Phe |
| Cys | Lys | Leu 35 | Val | Glu | His | Val | Pro 40 | Gly | Arg | Pro | Val | Arg 45 | His | Ala | Gln |
| Cys | Arg 50 | Val | Cys | Asp | Gly | Asn 55 | Ser | Thr | Asn | Pro | Arg 60 | Glu | Arg | His | Pro |
| Ile 65 | Ser | His | Ala | Ile | Asp 70 | Gly | Thr | Asn | Asn | Trp 75 | Trp | Gln | Ser | Pro | Ser 80 |
| Ile | Gln | Asn | Gly | Arg 85 | Glu | Tyr | His | Trp | Val 90 | Thr | Val | Thr | Leu | Asp 95 | Leu |
| Arg | Gln | Val | Phe 100 | Gln | Val | Ala | Tyr | Ile 105 | Ile | Ile | Lys | Ala | Ala 110 | Asn | Ala |
| Pro | Arg | Pro 115 | Gly | Asn | Trp | Ile | Leu 120 | Glu | Arg | Ser | Val | Asp 125 | Gly | Val | Lys |
| Phe | Lys 130 | Pro | Trp | Gln | Tyr | Tyr 135 | Ala | Val | Ser | Asp | Thr 140 | Glu | Cys | Leu | Thr |

|       |       |       |       |       |       |       |       |       |       |       |       |       |       |       |       |
|-------|-------|-------|-------|-------|-------|-------|-------|-------|-------|-------|-------|-------|-------|-------|-------|
| Arg 145 | Tyr | Lys | Ile | Thr | Pro 150 | Arg | Arg | Gly | Pro | Pro 155 | Thr | Tyr | Arg | Ala | Asp 160 |
| Asn | Glu | Val | Ile | Cys 165 | Thr | Ser | Tyr | Tyr | Ser 170 | Lys | Leu | Val | Pro | Leu 175 | Glu |
| His | Gly | Glu | Ile 180 | His | Thr | Ser | Leu | Ile 185 | Asn | Gly | Arg | Pro | Ser 190 | Ala | Asp |
| Asp | Pro | Ser 195 | Pro | Gln | Leu | Leu | Glu 200 | Phe | Thr | Ser | Ala | Arg 205 | Tyr | Ile | Arg |
| Leu | Arg 210 | Leu | Gln | Arg | Ile | Arg 215 | Thr | Leu | Asn | Ala | Asp 220 | Leu | Met | Thr | Leu |
| Ser 225 | His | Arg | Asp | Leu | Arg 230 | Asp | Leu | Asp | Pro | Ile 235 | Val | Thr | Arg | Arg | Tyr 240 |
| Tyr | Tyr | Ser | Ile | Lys 245 | Asp | Ile | Ser | Val | Gly 250 | Gly | Met |       |       |       |       |

( 2 ) INFORMATION FOR SEQ ID NO:10:

( i ) SEQUENCE CHARACTERISTICS:
        ( A ) LENGTH: 264 amino acids
        ( B ) TYPE: amino acid
        ( D ) TOPOLOGY: linear ( x i ) SEQUENCE DESCRIPTION: SEQ ID NO:10:

|       |       |       |       |       |       |       |       |       |       |       |       |       |       |       |       |
|-------|-------|-------|-------|-------|-------|-------|-------|-------|-------|-------|-------|-------|-------|-------|-------|
| Gln 1 | Arg | Pro | Gln | Gln 5 | Gln | Arg | Gln | Ser | Gln 10 | Ala | His | Gln | Gln | Arg 15 | Gly |
| Leu | Phe | Pro | Ala 20 | Val | Leu | Asn | Leu | Ala 25 | Ser | Asn | Ala | Leu | Ile 30 | Thr | Thr |
| Asn | Ala | Thr 35 | Cys | Gly | Glu | Lys | Gly 40 | Pro | Glu | Met | Tyr | Cys 45 | Lys | Leu | Val |
| Glu | His 50 | Val | Pro | Gly | Gln | Pro 55 | Val | Arg | Asn | Pro | Gln 60 | Cys | Arg | Ile | Cys |
| Asn 65 | Gln | Asn | Ser | Ser | Asn 70 | Pro | Asn | Gln | Arg | His 75 | Pro | Ile | Thr | Asn | Ala 80 |
| Ile | Asp | Gly | Lys | Asn 85 | Thr | Trp | Trp | Gln | Ser 90 | Pro | Ser | Ile | Lys | Asn 95 | Gly |
| Ile | Glu | Tyr | His 100 | Tyr | Val | Thr | Ile | Thr 105 | Leu | Asp | Leu | Gln | Gln 110 | Val | Phe |
| Gln | Ile | Ala 115 | Tyr | Val | Ile | Val | Lys 120 | Ala | Ala | Asn | Ser | Pro 125 | Arg | Pro | Gly |
| Asn | Trp 130 | Ile | Leu | Glu | Arg | Ser 135 | Leu | Asp | Asp | Val | Glu 140 | Tyr | Lys | Pro | Trp |
| Gln 145 | Tyr | His | Ala | Val | Thr 150 | Asp | Thr | Glu | Cys | Leu 155 | Thr | Leu | Tyr | Asn | Ile 160 |
| Tyr | Pro | Arg | Thr | Gly 165 | Pro | Pro | Ser | Tyr | Ala 170 | Lys | Asp | Asp | Glu | Val 175 | Ile |
| Cys | Thr | Ser | Phe 180 | Tyr | Ser | Lys | Ile | His 185 | Pro | Leu | Glu | Asn | Gly 190 | Glu | Ile |
| His | Ile | Ser 195 | Leu | Ile | Asn | Gly | Arg 200 | Pro | Ser | Ala | Asp | Pro 205 | Ser | Pro |
| Glu | Leu 210 | Leu | Glu | Phe | Thr | Ser 215 | Ala | Arg | Tyr | Ile | Arg 220 | Leu | Arg | Phe | Gln |
| Arg 225 | Ile | Arg | Thr | Leu | Asn 230 | Ala | Asp | Leu | Met | Met 235 | Phe | Ala | His | Lys | Asp 240 |
| Pro | Arg | Glu | Ile | Asp 245 | Pro | Ile | Val | Thr | Arg 250 | Arg | Tyr | Tyr | Tyr | Ser 255 | Val |
| Lys | Asp | Ile | Ser | Val 260 | Gly | Gly | Met |       |       |       |       |       |       |       |       |

( 2 ) INFORMATION FOR SEQ ID NO:11:

( i ) SEQUENCE CHARACTERISTICS:
        ( A ) LENGTH: 250 amino acids
        ( B ) TYPE: amino acid
        ( D ) TOPOLOGY: linear ( x i ) SEQUENCE DESCRIPTION: SEQ ID NO:11:

```
Glu Leu Thr Pro Pro Tyr Phe Asn Leu Ala Thr Gly Arg Lys Ile Tyr
 1               5                  10                  15
Ala Thr Ala Thr Cys Gly Pro Asp Thr Asp Gly Pro Glu Leu Tyr Cys
            20                  25                  30
Lys Leu Val Gly Ala Asn Thr Glu His Asp His Ile Asp Tyr Ser Val
         35                  40                  45
Ile Gln Gly Gln Val Cys Asp Tyr Cys Asp Pro Thr Val Pro Glu Arg
     50                  55                  60
Asn His Pro Pro Glu Asn Ala Ile Asp Gly Thr Glu Ala Trp Trp Gln
 65                  70                  75                  80
Ser Pro Pro Leu Ser Arg Gly Met Lys Phe Asn Glu Val Asn Leu Thr
                85                  90                  95
Ile Asn Phe Glu Gln Glu Phe His Val Ala Tyr Leu Phe Ile Arg Met
            100                 105                 110
Gly Asn Ser Pro Arg Pro Gly Leu Trp Thr Leu Glu Lys Ser Thr Asp
        115                 120                 125
Tyr Gly Lys Thr Trp Thr Pro Trp Gln His Phe Ser Asp Thr Pro Ala
    130                 135                 140
Asp Cys Glu Thr Tyr Phe Gly Lys Asp Thr Tyr Lys Pro Ile Thr Arg
145                 150                 155                 160
Asp Asp Asp Val Ile Cys Thr Thr Glu Tyr Ser Lys Ile Val Pro Leu
                165                 170                 175
Glu Asn Gly Glu Ile Pro Val Met Leu Leu Asn Glu Arg Pro Ser Ser
            180                 185                 190
Thr Asn Tyr Phe Asn Ser Thr Val Leu Gln Glu Trp Thr Arg Ala Thr
        195                 200                 205
Asn Val Arg Ile Arg Leu Leu Arg Thr Lys Asn Leu Leu Gly His Leu
    210                 215                 220
Met Ser Val Ala Arg Gln Asp Pro Thr Val Thr Arg Arg Tyr Phe Tyr
225                 230                 235                 240
Ser Ile Lys Asp Ile Ser Ile Gly Gly Arg
                245                 250
```

( 2 ) INFORMATION FOR SEQ ID NO:12:

( i ) SEQUENCE CHARACTERISTICS:
        ( A ) LENGTH: 252 amino acids
        ( B ) TYPE: amino acid
        ( D ) TOPOLOGY: linear ( x i ) SEQUENCE DESCRIPTION: SEQ ID NO:12:

```
Gln Ala Ala Met Asp Glu Cys Thr Asp Glu Gly Gly Arg Pro Gln Arg
 1               5                  10                  15
Cys Met Pro Glu Phe Val Asn Ala Ala Phe Asn Val Thr Val Val Ala
            20                  25                  30
Thr Asn Thr Cys Gly Thr Pro Pro Glu Glu Tyr Cys Val Gln Thr Gly
         35                  40                  45
Val Thr Gly Val Thr Lys Ser Cys His Leu Cys Asp Ala Gly Gln Pro
```

|   |   |   |   |   | 50 |   |   |   |   | 55 |   |   |   |   | 60 |   |   |   |   |
|---|---|---|---|---|----|---|---|---|---|----|---|---|---|---|----|---|---|---|---|

His Leu Gln His Gly Ala Ala Phe Leu Thr Asp Tyr Asn Asn Gln Ala
65                  70                  75                  80

Asp Thr Thr Trp Trp Gln Ser Gln Thr Met Leu Ala Gly Val Gln Tyr
                85                  90                  95

Pro Ser Ser Ile Asn Leu Thr Leu His Leu Gly Lys Ala Phe Asp Ile
            100                 105                 110

Thr Tyr Val Arg Leu Lys Phe His Thr Ser Arg Pro Glu Ser Phe Ala
        115                 120                 125

Ile Tyr Lys Arg Thr Arg Glu Asp Gly Pro Trp Ile Pro Tyr Gln Tyr
    130                 135                 140

Tyr Ser Gly Ser Cys Glu Asn Thr Tyr Ser Lys Ala Asn Arg Gly Phe
145                 150                 155                 160

Ile Arg Thr Gly Gly Asp Glu Gln Gln Ala Leu Cys Thr Asp Glu Phe
                165                 170                 175

Ser Asp Ile Ser Pro Leu Thr Gly Gly Asn Val Ala Phe Ser Thr Leu
            180                 185                 190

Glu Gly Arg Pro Ser Ala Tyr Asn Phe Asp Asn Ser Pro Val Leu Gln
        195                 200                 205

Glu Trp Val Thr Ala Thr Asp Ile Arg Val Thr Leu Asn Arg Leu Asn
    210                 215                 220

Thr Phe Gly Asp Glu Val Phe Asn Asp Pro Lys Val Leu Lys Ser Tyr
225                 230                 235                 240

Tyr Tyr Ala Ile Ser Asp Phe Ala Val Gly Gly Arg
                245                 250

(2) INFORMATION FOR SEQ ID NO:13:

(i) SEQUENCE CHARACTERISTICS:
       (A) LENGTH: 278 amino acids
       (B) TYPE: amino acid
       (D) TOPOLOGY: linear (xi) SEQUENCE DESCRIPTION: SEQ ID NO:13:

Cys Phe Cys Tyr Gly His Ala Ser Glu Cys Ala Pro Val Asp Gly Phe
1               5                   10                  15

Asn Glu Glu Val Glu Gly Met Val His Gly His Cys Met Cys Arg His
            20                  25                  30

Asn Thr Lys Gly Leu Asn Cys Glu Leu Cys Met Asp Phe Tyr His Asp
        35                  40                  45

Leu Pro Trp Arg Pro Ala Glu Gly Arg Asn Ser Asn Ala Cys Lys Lys
    50                  55                  60

Cys Asn Cys Asn Glu His Ser Ile Ser Cys His Phe Asp Met Ala Val
65                  70                  75                  80

Tyr Leu Ala Thr Gly Asn Val Ser Gly Gly Val Cys Asp Asp Cys Gln
                85                  90                  95

His Asn Thr Met Gly Arg Asn Cys Glu Gln Cys Lys Pro Phe Tyr Tyr
            100                 105                 110

Gln His Pro Glu Arg Asp Ile Arg Asp Pro Asn Phe Cys Glu Arg Cys
        115                 120                 125

Thr Cys Asp Pro Ala Gly Ser Gln Asn Glu Gly Ile Cys Asp Ser Tyr
    130                 135                 140

Thr Asp Phe Ser Thr Gly Leu Ile Ala Gly Gln Cys Arg Cys Lys Leu
145                 150                 155                 160

Asn Val Glu Gly Glu His Cys Asp Val Cys Lys Glu Gly Phe Tyr Asp
                165                 170                 175

|     |     |     |     |     |     |     |     |     |     |     |     |     |     |     |
| --- | --- | --- | --- | --- | --- | --- | --- | --- | --- | --- | --- | --- | --- | --- |
| Leu | Ser | Ser | Glu | Asp | Pro | Phe | Gly | Cys | Lys | Ser | Cys | Ala | Cys | Asn | Pro |
|     |     |     | 180 |     |     |     |     | 185 |     |     |     |     | 190 |     |     |
| Leu | Gly | Thr | Ile | Pro | Gly | Gly | Asn | Pro | Cys | Asp | Ser | Glu | Thr | Gly | His |
|     |     | 195 |     |     |     |     | 200 |     |     |     |     | 205 |     |     |     |
| Cys | Tyr | Cys | Lys | Arg | Leu | Val | Thr | Gly | Gln | His | Cys | Asp | Gln | Cys | Leu |
|     | 210 |     |     |     |     | 215 |     |     |     |     | 220 |     |     |     |     |
| Pro | Glu | His | Trp | Gly | Leu | Ser | Asn | Asp | Leu | Asp | Gly | Cys | Arg | Pro | Cys |
| 225 |     |     |     |     | 230 |     |     |     |     | 235 |     |     |     |     | 240 |
| Asp | Cys | Asp | Leu | Gly | Gly | Ala | Leu | Asn | Asn | Ser | Cys | Phe | Ala | Glu | Ser |
|     |     |     |     | 245 |     |     |     |     | 250 |     |     |     |     | 255 |     |
| Gly | Gln | Cys | Ser | Cys | Arg | Pro | His | Met | Ile | Gly | Arg | Gln | Cys | Asn | Glu |
|     |     |     | 260 |     |     |     |     | 265 |     |     |     |     | 270 |     |     |
| Val | Glu | Pro | Gly | Tyr | Tyr |
|     |     | 275 |     |     |     |

( 2 ) INFORMATION FOR SEQ ID NO:14:

( i ) SEQUENCE CHARACTERISTICS:
        ( A ) LENGTH: 269 amino acids
        ( B ) TYPE: amino acid
        ( D ) TOPOLOGY: linear ( x i ) SEQUENCE DESCRIPTION: SEQ ID NO:14:

|     |     |     |     |     |     |     |     |     |     |     |     |     |     |     |     |
| --- | --- | --- | --- | --- | --- | --- | --- | --- | --- | --- | --- | --- | --- | --- | --- |
| Cys | Phe | Cys | Tyr | Gly | His | Ala | Ser | Gln | Cys | Ala | Pro | Ala | Pro | Gly | Ala |
| 1   |     |     |     | 5   |     |     |     |     | 10  |     |     |     |     | 15  |     |
| Pro | Ala | His | Ala | Glu | Gly | Met | Val | His | Gly | Ala | Cys | Ile | Cys | Lys | His |
|     |     |     | 20  |     |     |     |     | 25  |     |     |     |     | 30  |     |     |
| Asn | Thr | Arg | Gly | Leu | Asn | Cys | Glu | Gln | Cys | Gln | Asp | Phe | Tyr | Gln | Asp |
|     |     | 35  |     |     |     |     | 40  |     |     |     |     | 45  |     |     |     |
| Leu | Pro | Trp | His | Pro | Ala | Glu | Asp | Gly | His | Thr | His | Ala | Cys | Arg | Lys |
|     | 50  |     |     |     |     | 55  |     |     |     |     | 60  |     |     |     |     |
| Cys | Glu | Cys | Asn | Gly | His | Ser | His | Ser | Cys | His | Phe | Asp | Met | Ala | Val |
| 65  |     |     |     |     | 70  |     |     |     |     | 75  |     |     |     |     | 80  |
| Tyr | Leu | Ala | Ser | Gly | Asn | Val | Ser | Gly | Gly | Val | Cys | Asp | Gly | Cys | Gln |
|     |     |     |     | 85  |     |     |     |     | 90  |     |     |     |     | 95  |     |
| His | Asn | Thr | Ala | Gly | Arg | His | Cys | Glu | Leu | Cys | Arg | Pro | Phe | Phe | Tyr |
|     |     |     | 100 |     |     |     |     | 105 |     |     |     |     | 110 |     |     |
| Arg | Asp | Pro | Thr | Lys | Asp | Met | Arg | Asp | Pro | Ala | Ala | Cys | Arg | Pro | Cys |
|     |     |     | 115 |     |     |     |     | 120 |     |     |     |     | 125 |     |     |
| Asp | Cys | Asp | Pro | Met | Gly | Ser | Gln | Asp | Gly | Gly | Arg | Cys | Asp | Ser | His |
|     | 130 |     |     |     |     | 135 |     |     |     |     | 140 |     |     |     |     |
| Asp | Asp | Pro | Val | Leu | Gly | Leu | Val | Ser | Gly | Gln | Cys | Arg | Cys | Lys | Glu |
| 145 |     |     |     |     | 150 |     |     |     |     | 155 |     |     |     |     | 160 |
| His | Val | Val | Gly | Thr | Arg | Cys | Gln | Gln | Cys | Arg | Asp | Gly | Phe | Phe | Gly |
|     |     |     |     | 165 |     |     |     |     | 170 |     |     |     |     | 175 |     |
| Leu | Ser | Ala | Ser | Asn | Pro | Arg | Gly | Cys | Gln | Arg | Cys | Gln | Cys | Asn | Ser |
|     |     |     | 180 |     |     |     |     | 185 |     |     |     |     | 190 |     |     |
| Arg | Gly | Thr | Val | Pro | Gly | Gly | Thr | Pro | Cys | Asp | Ser | Ser | Ser | Gly | Thr |
|     |     | 195 |     |     |     |     | 200 |     |     |     |     | 205 |     |     |     |
| Cys | Phe | Cys | Lys | Arg | Leu | Val | Thr | Gly | Asp | Gly | Cys | Asp | Arg | Cys | Leu |
|     | 210 |     |     |     |     | 215 |     |     |     |     | 220 |     |     |     |     |
| Pro | Gly | His | Trp | Gly | Leu | Ser | His | Asp | Leu | Leu | Gly | Cys | Arg | Pro | Cys |
| 225 |     |     |     |     | 230 |     |     |     |     | 235 |     |     |     |     | 240 |
| Asp | Cys | Asp | Val | Gly | Gly | Ala | Leu | Asp | Pro | Gln | Cys | Asp | Glu | Ala | Thr |
|     |     |     |     | 245 |     |     |     |     | 250 |     |     |     |     | 255 |     |

```
            Gly Gln Cys Pro Cys Arg Pro His Met Ile Gly Arg Arg
                        260                 265
```

(2) INFORMATION FOR SEQ ID NO:15:

(i) SEQUENCE CHARACTERISTICS:
        (A) LENGTH: 243 amino acids
        (B) TYPE: amino acid
        (D) TOPOLOGY: linear (xi) SEQUENCE DESCRIPTION: SEQ ID NO:15:

```
Cys Ile Cys Tyr Gly His Ala Ser Ser Cys Pro Trp Asp Glu Thr Thr
1               5                   10                  15

Lys Lys Leu Gln Cys Gln Cys Glu His Asn Thr Cys Gly Glu Ser Cys
            20                  25                  30

Asn Arg Cys Cys Pro Gly Tyr His Gln Gln Pro Trp Arg Pro Gly Thr
        35                  40                  45

Val Ser Ser Gly Asn Thr Cys Glu Ala Cys Asn Cys His Asn Lys Ala
    50                  55                  60

Lys Asp Cys Tyr Tyr Asp Glu Ser Val Ala Lys Gln Lys Ser Leu
65              70                  75                  80

Asn Thr Ala Gly Gln Phe Arg Gly Gly Val Cys Ile Asn Cys Leu
                85                  90                  95

Gln Asn Thr Met Gly Ile Asn Cys Glu Thr Cys Ile Asp Gly Tyr Tyr
            100                 105                 110

Arg Pro His Lys Val Ser Pro Tyr Glu Asp Glu Pro Cys Arg Pro Cys
        115                 120                 125

Asn Cys Asp Pro Val Gly Ser Leu Ser Ser Val Cys Ile Lys Asp Asp
    130                 135                 140

Leu His Ser Asp Leu Glu Asn Gly Lys Gln Pro Gly Gln Cys Pro Cys
145                 150                 155                 160

Lys Glu Gly Tyr Thr Gly Glu Lys Cys Asp Arg Cys Gln Leu Gly Tyr
                165                 170                 175

Lys Asp Tyr Pro Thr Cys Val Ser Cys Gly Cys Asn Pro Val Gly Ser
            180                 185                 190

Ala Ser Asp Glu Pro Cys Thr Gly Pro Cys Val Cys Lys Glu Asn Val
        195                 200                 205

Glu Gly Lys Ala Cys Asp Arg Cys Lys Pro Gly Phe Tyr Asn Leu Lys
    210                 215                 220

Glu Lys Asn Pro Arg Gly Cys Ser Glu Cys Phe Cys Phe Gly Val Ser
225                 230                 235                 240

Asp Val Cys
```

(2) INFORMATION FOR SEQ ID NO:16:

(i) SEQUENCE CHARACTERISTICS:
        (A) LENGTH: 243 amino acids
        (B) TYPE: amino acid
        (D) TOPOLOGY: linear (xi) SEQUENCE DESCRIPTION: SEQ ID NO:16:

```
Cys Ile Cys Tyr Gly His Ala Ser Ser Cys Pro Trp Asp Glu Glu Ala
1               5                   10                  15

Lys Gln Leu Gln Cys Gln Cys Glu His Asn Thr Cys Gly Glu Ser Cys
            20                  25                  30

Asp Arg Cys Cys Pro Gly Tyr His Gln Gln Pro Trp Arg Pro Gly Thr
        35                  40                  45

Ile Ser Ser Gly Asn Glu Cys Glu Glu Cys Asn Cys His Asn Lys Ala
```

|      |      |      |      |      |      |      |      |      |      |      |      |      |      |      |      |
|------|------|------|------|------|------|------|------|------|------|------|------|------|------|------|------|
|      |      |      |      |      | 50   |      |      |      |      | 55   |      |      |      |      | 60   |
| Lys  | Asp  | Cys  | Tyr  | Tyr  | Asp  | Ser  | Ser  | Val  | Ala  | Lys  | Glu  | Arg  | Arg  | Ser  | Leu  |
| 65   |      |      |      |      | 70   |      |      |      |      | 75   |      |      |      |      | 80   |
| Asn  | Thr  | Ala  | Gly  | Gln  | Tyr  | Ser  | Gly  | Gly  | Val  | Cys  | Val  | Asn  | Cys  | Ser  |      |
|      |      |      |      | 85   |      |      |      | 90   |      |      |      |      | 95   |      |      |
| Gln  | Asn  | Thr  | Thr  | Gly  | Ile  | Asn  | Cys  | Glu  | Thr  | Cys  | Ile  | Asp  | Gln  | Tyr  | Tyr  |
|      |      |      | 100  |      |      |      |      | 105  |      |      |      |      | 110  |      |      |
| Arg  | Pro  | His  | Lys  | Val  | Ser  | Pro  | Tyr  | Asp  | His  | Pro  | Cys  | Arg  | Pro  | Cys  |      |
|      |      | 115  |      |      |      |      | 120  |      |      |      | 125  |      |      |      |      |
| Asn  | Cys  | Asp  | Pro  | Val  | Gly  | Ser  | Leu  | Ser  | Ser  | Val  | Cys  | Ile  | Lys  | Asp  | Asp  |
|      | 130  |      |      |      |      | 135  |      |      |      |      | 140  |      |      |      |      |
| Arg  | His  | Ala  | Asp  | Leu  | Ala  | Asn  | Gly  | Lys  | Trp  | Pro  | Gly  | Gln  | Cys  | Pro  | Cys  |
| 145  |      |      |      |      | 150  |      |      |      |      | 155  |      |      |      |      | 160  |
| Arg  | Lys  | Gly  | Tyr  | Ala  | Gly  | Asp  | Lys  | Cys  | Asp  | Arg  | Cys  | Gln  | Phe  | Gly  | Tyr  |
|      |      |      |      | 165  |      |      |      |      | 170  |      |      |      |      | 175  |      |
| Arg  | Gly  | Phe  | Pro  | Asn  | Cys  | Ile  | Pro  | Cys  | Asp  | Cys  | Arg  | Thr  | Val  | Gly  | Ser  |
|      |      |      | 180  |      |      |      |      | 185  |      |      |      |      | 190  |      |      |
| Leu  | Asn  | Glu  | Asp  | Pro  | Cys  | Ile  | Glu  | Pro  | Cys  | Leu  | Cys  | Lys  | Lys  | Asn  | Val  |
|      |      | 195  |      |      |      |      | 200  |      |      |      | 205  |      |      |      |      |
| Glu  | Gly  | Lys  | Asn  | Cys  | Asp  | Arg  | Cys  | Lys  | Pro  | Gly  | Phe  | Tyr  | Asn  | Leu  | Lys  |
|      | 210  |      |      |      |      | 215  |      |      |      |      | 220  |      |      |      |      |
| Glu  | Arg  | Asn  | Pro  | Glu  | Gly  | Cys  | Ser  | Glu  | Cys  | Phe  | Cys  | Phe  | Gly  | Val  | Ser  |
| 225  |      |      |      |      | 230  |      |      |      |      | 235  |      |      |      |      | 240  |
| Gly  | Val  | Cys  |      |      |      |      |      |      |      |      |      |      |      |      |      |

( 2 ) INFORMATION FOR SEQ ID NO:17:

( i ) SEQUENCE CHARACTERISTICS:
        ( A ) LENGTH: 241 amino acids
        ( B ) TYPE: amino acid
        ( D ) TOPOLOGY: linear ( x i ) SEQUENCE DESCRIPTION: SEQ ID NO:17:

|      |      |      |      |      |      |      |      |      |      |      |      |      |      |      |      |
|------|------|------|------|------|------|------|------|------|------|------|------|------|------|------|------|
| Cys  | Ile  | Cys  | Tyr  | Gly  | His  | Ala  | Arg  | Ala  | Cys  | Pro  | Leu  | Asp  | Pro  | Ala  | Thr  |
| 1    |      |      |      | 5    |      |      |      |      | 10   |      |      |      |      | 15   |      |
| Asn  | Lys  | Ser  | Arg  | Cys  | Glu  | Cys  | Glu  | His  | Asn  | Thr  | Cys  | Gly  | Asp  | Ser  | Cys  |
|      |      |      | 20   |      |      |      |      | 25   |      |      |      |      | 30   |      |      |
| Asp  | Gln  | Cys  | Cys  | Pro  | Gly  | Phe  | His  | Gln  | Lys  | Pro  | Trp  | Arg  | Ala  | Gly  | Thr  |
|      |      | 35   |      |      |      |      | 40   |      |      |      |      | 45   |      |      |      |
| Phe  | Leu  | Thr  | Lys  | Thr  | Glu  | Cys  | Glu  | Ala  | Cys  | Asn  | Cys  | His  | Gly  | Lys  | Ala  |
|      |      |      | 50   |      |      |      |      | 55   |      |      |      |      | 60   |      |      |
| Glu  | Glu  | Cys  | Tyr  | Tyr  | Asp  | Glu  | Asn  | Val  | Ala  | Arg  | Arg  | Asn  | Leu  | Ser  | Leu  |
| 65   |      |      |      |      | 70   |      |      |      |      | 75   |      |      |      |      | 80   |
| Asn  | Ile  | Arg  | Gly  | Lys  | Tyr  | Ile  | Gly  | Gly  | Val  | Cys  | Ile  | Asn  | Cys  | Thr  |      |
|      |      |      |      | 85   |      |      |      | 90   |      |      |      |      | 95   |      |      |
| Gln  | Asn  | Thr  | Ala  | Gly  | Ile  | Asn  | Cys  | Glu  | Thr  | Cys  | Thr  | Asp  | Gly  | Phe  | Phe  |
|      |      |      | 100  |      |      |      |      | 105  |      |      |      |      | 110  |      |      |
| Arg  | Pro  | Lys  | Gly  | Val  | Ser  | Pro  | Asn  | Tyr  | Pro  | Arg  | Pro  | Cys  | Gln  | Pro  | Cys  |
|      |      | 115  |      |      |      |      | 120  |      |      |      | 125  |      |      |      |      |
| His  | Cys  | Asp  | Pro  | Ile  | Gly  | Ser  | Leu  | Asn  | Glu  | Val  | Cys  | Val  | Lys  | Asp  | Glu  |
|      | 130  |      |      |      |      | 135  |      |      |      |      | 140  |      |      |      |      |
| Lys  | His  | Ala  | Arg  | Arg  | Gly  | Leu  | Ala  | Pro  | Gly  | Ser  | Cys  | His  | Cys  | Lys  | Thr  |
| 145  |      |      |      |      | 150  |      |      |      |      | 155  |      |      |      |      | 160  |
| Gly  | Phe  | Gly  | Gly  | Val  | Ser  | Cys  | Asp  | Arg  | Cys  | Ala  | Arg  | Gly  | Tyr  | Thr  | Gly  |
|      |      |      |      | 165  |      |      |      |      | 170  |      |      |      |      | 175  |      |

|     |     |     |     |     |     |     |     |     |     |     |     |     |     |     |
| --- | --- | --- | --- | --- | --- | --- | --- | --- | --- | --- | --- | --- | --- | --- |
| Tyr | Pro | Asp | Cys | Lys | Ala | Cys | Asn | Cys | Ser | Gly | Leu | Gly | Ser | Lys | Asn |
|     |     |     | 180 |     |     |     | 185 |     |     |     |     |     | 190 |     |     |
| Glu | Asp | Pro | Cys | Phe | Gly | Pro | Cys | Ile | Cys | Lys | Glu | Asn | Val | Glu | Gly |
|     |     | 195 |     |     |     |     | 200 |     |     |     |     | 205 |     |     |     |
| Gly | Asp | Cys | Ser | Arg | Cys | Lys | Ser | Gly | Phe | Phe | Asn | Leu | Gln | Glu | Asp |
|     |     | 210 |     |     |     |     | 215 |     |     |     | 220 |     |     |     |     |
| Asn | Trp | Lys | Gly | Cys | Asp | Glu | Cys | Phe | Cys | Ser | Gly | Val | Ser | Asn | Arg |
| 225 |     |     |     |     | 230 |     |     |     |     | 235 |     |     |     |     | 240 |
| Cys |     |     |     |     |     |     |     |     |     |     |     |     |     |     |     |

( 2 ) INFORMATION FOR SEQ ID NO:18:

( i ) SEQUENCE CHARACTERISTICS:
        ( A ) LENGTH: 219 amino acids
        ( B ) TYPE: amino acid
        ( D ) TOPOLOGY: linear ( x i ) SEQUENCE DESCRIPTION: SEQ ID NO:18:

|     |     |     |     |     |     |     |     |     |     |     |     |     |     |     |     |
| --- | --- | --- | --- | --- | --- | --- | --- | --- | --- | --- | --- | --- | --- | --- | --- |
| Cys | Lys | Cys | Asn | Gly | His | Ala | Ser | Glu | Cys | Met | Lys | Asn | Glu | Phe | Asp |
| 1   |     |     |     | 5   |     |     |     |     | 10  |     |     |     |     | 15  |     |
| Lys | Leu | Val | Cys | Asn | Cys | Lys | His | Asn | Thr | Tyr | Gly | Val | Asp | Cys | Glu |
|     |     |     | 20  |     |     |     |     | 25  |     |     |     |     | 30  |     |     |
| Lys | Cys | Leu | Pro | Phe | Phe | Asn | Asp | Arg | Pro | Trp | Arg | Arg | Ala | Thr | Ala |
|     |     | 35  |     |     |     |     | 40  |     |     |     |     | 45  |     |     |     |
| Glu | Ser | Ala | Ser | Glu | Cys | Leu | Pro | Cys | Asp | Cys | Asn | Gly | Arg | Ser | Gln |
|     | 50  |     |     |     |     | 55  |     |     |     |     | 60  |     |     |     |     |
| Glu | Cys | Tyr | Phe | Asp | Pro | Glu | Leu | Tyr | Arg | Ser | Thr | Gly | His | Gly | Gly |
| 65  |     |     |     |     | 70  |     |     |     |     | 75  |     |     |     |     | 80  |
| His | Cys | Thr | Asn | Cys | Gln | Asp | Asn | Thr | Asp | Gly | Ala | His | Cys | Glu | Arg |
|     |     |     |     | 85  |     |     |     |     | 90  |     |     |     |     | 95  |     |
| Cys | Arg | Glu | Asn | Phe | Phe | Arg | Leu | Gly | Asn | Asn | Glu | Ala | Cys | Ser | Ser |
|     |     |     | 100 |     |     |     |     | 105 |     |     |     |     | 110 |     |     |
| Cys | His | Cys | Ser | Pro | Val | Gly | Ser | Leu | Ser | Thr | Gln | Cys | Asp | Ser | Tyr |
|     |     | 115 |     |     |     |     | 120 |     |     |     |     | 125 |     |     |     |
| Gly | Arg | Cys | Ser | Cys | Lys | Pro | Gly | Val | Met | Gly | Asp | Lys | Cys | Asp | Arg |
|     | 130 |     |     |     |     | 135 |     |     |     |     | 140 |     |     |     |     |
| Cys | Gln | Pro | Gly | Phe | His | Ser | Leu | Thr | Glu | Ala | Gly | Cys | Arg | Pro | Cys |
| 145 |     |     |     |     | 150 |     |     |     |     | 155 |     |     |     |     | 160 |
| Ser | Cys | Asp | Pro | Ser | Gly | Ser | Ile | Asp | Glu | Cys | Asn | Val | Glu | Thr | Gly |
|     |     |     |     | 165 |     |     |     |     | 170 |     |     |     |     | 175 |     |
| Arg | Cys | Val | Cys | Lys | Asp | Asn | Val | Glu | Gly | Phe | Asn | Cys | Glu | Arg | Cys |
|     |     |     | 180 |     |     |     |     | 185 |     |     |     |     | 190 |     |     |
| Lys | Pro | Gly | Phe | Phe | Asn | Leu | Glu | Ser | Ser | Asn | Pro | Arg | Gly | Cys | Thr |
|     |     | 195 |     |     |     |     | 200 |     |     |     |     | 205 |     |     |     |
| Pro | Cys | Phe | Cys | Phe | Gly | His | Ser | Ser | Val | Cys |     |     |     |     |     |
|     | 210 |     |     |     |     | 215 |     |     |     |     |     |     |     |     |     |

( 2 ) INFORMATION FOR SEQ ID NO:19:

( i ) SEQUENCE CHARACTERISTICS:
        ( A ) LENGTH: 314 amino acids
        ( B ) TYPE: amino acid
        ( D ) TOPOLOGY: linear ( x i ) SEQUENCE DESCRIPTION: SEQ ID NO:19:

|     |     |     |     |     |     |     |     |     |     |     |     |     |     |     |     |
| --- | --- | --- | --- | --- | --- | --- | --- | --- | --- | --- | --- | --- | --- | --- | --- |
| Cys | Met | Cys | Asn | Gly | His | Ala | Asp | Thr | Cys | Asp | Val | Lys | Asp | Pro | Lys |
| 1   |     |     |     | 5   |     |     |     |     | 10  |     |     |     |     | 15  |     |
| Ser | Pro | Val | Arg | Ile | Leu | Ala | Cys | Arg | Cys | Gln | His | His | Thr | Cys | Gly |

|     |     |     | 20  |     |     | 25  |     |     |     | 30  |     |     |     |
| --- | --- | --- | --- | --- | --- | --- | --- | --- | --- | --- | --- | --- | --- |
| Ile | Gln | Cys<br>35 | Asn | Glu | Cys | Cys | Pro<br>40 | Gly | Phe | Glu | Gln | Lys<br>45 | Trp | Arg |
| Gln | Asn | Thr | Asn | Ala | Arg | Pro<br>55 | Phe | Asn | Cys | Glu | Pro<br>60 | Cys | Asn | Cys | His |
| Gly<br>65 | His | Ser | Asn | Glu | Cys<br>70 | Lys | Tyr | Asp | Glu | Val<br>75 | Asn | Arg | Lys | Gly<br>80 |
| Leu | Ser | Leu | Asp | Ile<br>85 | His | Gly | His | Tyr | Asp<br>90 | Gly | Gly | Gly | Val | Cys<br>95 | Gln |
| Asn | Cys | Gln | His<br>100 | Asn | Thr | Val | Gly | Ile<br>105 | Asn | Cys | Asn | Lys | Cys<br>110 | Lys | Pro |
| Lys | Tyr | Tyr<br>115 | Arg | Pro | Lys | Gly | Lys<br>120 | His | Trp | Asn | Glu | Thr<br>125 | Asp | Val | Cys |
| Ser | Pro<br>130 | Cys | Gln | Cys | Asp | Tyr<br>135 | Phe | Phe | Ser | Thr | Gly<br>140 | His | Cys | Glu | Glu |
| Glu<br>145 | Thr | Gly | Asn | Cys | Glu<br>150 | Cys | Arg | Ala | Ala | Phe<br>155 | Gln | Pro | Pro | Ser | Cys<br>160 |
| Asp | Ser | Cys | Ala | Tyr<br>165 | Gly | Tyr | Tyr | Gly<br>170 | Tyr | Pro | Asn | Cys | Arg | Glu<br>175 | Cys |
| Glu | Cys | Asn | Leu<br>180 | Asn | Gly | Thr | Asn | Gly<br>185 | Tyr | His | Cys | Glu | Ala<br>190 | Glu | Ser |
| Gly | Gln | Gln<br>195 | Cys | Pro | Cys | Lys | Ile<br>200 | Asn | Phe | Ala | Phe<br>205 | Ala | Tyr | Cys | Lys |
| Gln | Cys<br>210 | Ala | Glu | Gly | Tyr | Tyr<br>215 | Gly | Phe | Pro | Glu | Cys<br>220 | Lys | Ala | Cys | Glu |
| Cys<br>225 | Asn | Lys | Ile | Gly | Ser<br>230 | Ile | Thr | Asn | Asp | Cys<br>235 | Asn | Val | Thr | Thr | Gly<br>240 |
| Glu | Cys | Lys | Cys | Leu<br>245 | Thr | Asn | Phe | Gly | Gly<br>250 | Asp | Asn | Cys | Glu | Arg<br>255 | Cys |
| Lys | His | Gly | Tyr<br>260 | Phe | Asn | Tyr | Pro | Thr<br>265 | Cys | Ser | Tyr | Cys<br>270 | Asp | Cys | Asp |
| Asn | Gln | Gly<br>275 | Thr | Glu | Ser | Glu | Ile<br>280 | Cys | Asn | Lys | Gln | Ser<br>285 | Gly | Gln | Cys |
| Ile | Cys<br>290 | Arg | Glu | Gly | Phe | Gly<br>295 | Gly | Pro | Arg | Cys | Asp<br>300 | Gln | Cys | Leu | Pro |
| Gly<br>305 | Phe | Tyr | Asn | Tyr | Pro<br>310 | Asp | Cys | Lys | Pro |     |     |     |     |     |     |

( 2 ) INFORMATION FOR SEQ ID NO:20:

( i ) SEQUENCE CHARACTERISTICS:
        ( A ) LENGTH: 169 amino acids
        ( B ) TYPE: amino acid
        ( D ) TOPOLOGY: linear ( x i ) SEQUENCE DESCRIPTION: SEQ ID NO:20:

| Cys<br>1 | Asp | Cys | Asn | Gly<br>5 | Lys | Ser | Arg | Gln | Cys<br>10 | Ile | Phe | Asp | Arg | Glu<br>15 | Leu |
| --- | --- | --- | --- | --- | --- | --- | --- | --- | --- | --- | --- | --- | --- | --- | --- |
| His | Arg | Gln | Thr<br>20 | Gly | Asn | Gly | Phe | Arg<br>25 | Cys | Leu | Asn | Cys | Asn<br>30 | Asp | Asn |
| Thr | Asp | Gly<br>35 | Ile | His | Cys | Glu | Lys<br>40 | Cys | Lys | Asn | Gly | Phe<br>45 | Tyr | Arg | His |
| Arg | Glu<br>50 | Arg | Asp | Arg | Cys | Leu<br>55 | Pro | Cys | Asn | Cys | Asn<br>60 | Ser | Lys | Gly | Ser |
| Leu<br>65 | Ser | Ala | Arg | Cys | Asp<br>70 | Asn | Ser | Gly | Arg | Cys<br>75 | Ser | Cys | Lys | Pro | Gly<br>80 |

```
Val  Thr  Gly  Ala  Arg  Cys  Asp  Arg  Cys  Leu  Pro  Gly  Phe  His  Met  Leu
               85                      90                      95

Thr  Asp  Ala  Gly  Cys  Thr  Gln  Asp  Gln  Arg  Leu  Leu  Asp  Ser  Lys  Cys
               100                     105                     110

Asp  Cys  Asp  Pro  Ala  Gly  Ile  Ala  Gly  Pro  Cys  Asp  Ala  Gly  Arg  Cys
          115                      120                     125

Val  Cys  Lys  Pro  Ala  Val  Thr  Gly  Glu  Arg  Cys  Asp  Arg  Cys  Arg  Ser
     130                      135                     140

Gly  Tyr  Tyr  Asn  Leu  Asp  Gly  Gly  Asn  Pro  Glu  Gly  Cys  Thr  Gln  Cys
145                      150                     155                          160

Phe  Cys  Tyr  Gly  His  Ser  Ala  Ser  Cys
               165
```

( 2 ) INFORMATION FOR SEQ ID NO:21:

( i ) SEQUENCE CHARACTERISTICS:
( A ) LENGTH: 7 amino acids
( B ) TYPE: amino acid
( D ) TOPOLOGY: linear ( x i ) SEQUENCE DESCRIPTION: SEQ ID NO:21:

```
Leu  Phe  Val  Gly  Gly  Leu  Pro
1                5
```

( 2 ) INFORMATION FOR SEQ ID NO:22:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO:22:

```
Cys  Asn  Asn  Phe  Gly  Leu  Asp  Leu  Lys  Ala  Asp  Asp  Lys  Ile
1                5                        10
```

( 2 ) INFORMATION FOR SEQ ID NO:23:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO:23:

```
Cys  Ser  Ile  Val  Asp  Ile  Asp  Thr  Asn  Gln  Glu  Glu  Asn  Ile
1               5                        10
```